(12) United States Patent
Yang et al.

(10) Patent No.: US 9,849,125 B1
(45) Date of Patent: Dec. 26, 2017

(54) ANTI-OVERINGESTION DOSAGE FORMS

(71) Applicant: BANNER LIFE SCIENCES LLC, High Point, NC (US)

(72) Inventors: Chue Hue Yang, Greensboro, NC (US); Tatyana Dyakonov, Greensboro, NC (US); Nashwa El-Gendy, Greensboro, NC (US); Jason M Vaughn, Browns Summit, NC (US); Justin R Hughey, Asheboro, NC (US)

(73) Assignee: Banner Life Sciences LLC, High Point, NC (US)

( * ) Notice: Subject to any disclaimer, the term of this patent is extended or adjusted under 35 U.S.C. 154(b) by 0 days.

(21) Appl. No.: 15/341,143

(22) Filed: Nov. 2, 2016

Related U.S. Application Data

(60) Provisional application No. 62/250,284, filed on Nov. 3, 2015.

(51) Int. Cl.
| | | |
|---|---|---|
| *A61K 31/485* | (2006.01) | |
| *A61K 9/20* | (2006.01) | |
| *A61K 9/00* | (2006.01) | |

(52) U.S. Cl.
CPC .......... *A61K 31/485* (2013.01); *A61K 9/0053* (2013.01); *A61K 9/2027* (2013.01)

(58) Field of Classification Search
CPC .............. A61K 31/485; A61K 51/1241; A61K 47/48184
See application file for complete search history.

(56) References Cited

U.S. PATENT DOCUMENTS

| | | | |
|---|---|---|---|
| 4,459,278 | A | 7/1984 | Porter |
| 4,529,583 | A | 7/1985 | Porter |
| 6,383,736 | B1 | 5/2002 | Titmas |
| 6,514,531 | B1 | 2/2003 | Alaux |
| 7,141,250 | B2 | 11/2006 | Wright |
| 7,144,587 | B2 | 12/2006 | Wright |
| 7,157,100 | B2 | 1/2007 | Joshi |
| 7,157,103 | B2 | 1/2007 | Sackler |
| 7,160,559 | B1 | 1/2007 | De Bruijn |
| 7,201,920 | B2 | 4/2007 | Wadgaonkar |
| 7,332,182 | B2 | 2/2008 | Sackler |
| 7,384,653 | B2 | 6/2008 | Carpanzano |
| 7,476,402 | B2 | 1/2009 | Wadgaonkar |
| 7,510,726 | B2 | 3/2009 | Wadgaonkar |
| 7,632,921 | B2 | 12/2009 | Mei |
| 7,682,633 | B2 | 3/2010 | Boehm |
| 7,682,634 | B2 | 3/2010 | Boehm |
| 7,727,557 | B2 | 6/2010 | Sackler |
| 7,749,954 | B2 | 7/2010 | Christiansen |
| 7,842,307 | B2 | 11/2010 | Wright |

(Continued)

OTHER PUBLICATIONS

SenGupta (Ion Exchange and Solvent Extraction: A series of Advances 2007, vol. 18 CRC Press pp. 127-130 7 pages total).*

(Continued)

*Primary Examiner* — Ernst V Arnold
(74) *Attorney, Agent, or Firm* — Brinks Gilson & Lione

(57) ABSTRACT

Described herein are abuse deterrent oral pharmaceutical compositions, methods for making the same, and methods of treatment using such compositions. In particular, oral pharmaceutical compositions that mitigate the risk of overingestion of one or more active pharmaceutical ingredients are described.

20 Claims, 20 Drawing Sheets

(56) References Cited

U.S. PATENT DOCUMENTS

| | | |
|---|---|---|
| 7,858,609 B2 | 12/2010 | Zhang |
| 7,914,818 B2 | 3/2011 | Wright |
| 7,955,619 B2 | 6/2011 | Difalco |
| 7,981,439 B2 | 7/2011 | Wadgaonkar |
| 8,017,148 B2 | 9/2011 | Sackler |
| 8,022,054 B2 | 9/2011 | Zhang |
| 8,062,667 B2 | 11/2011 | Tu |
| 8,101,630 B2 | 1/2012 | Wadgaonkar |
| 8,124,126 B2 | 2/2012 | Bosse |
| 8,153,590 B2 | 4/2012 | Sinha |
| 8,158,156 B2 | 4/2012 | Boehm |
| 8,182,836 B2 | 5/2012 | Mehta |
| 8,202,537 B2 | 6/2012 | Tu |
| 8,202,542 B1 | 6/2012 | Perumal |
| 8,231,901 B2 | 7/2012 | Wright |
| 8,236,353 B2 | 8/2012 | Breyne |
| 8,267,452 B2 | 9/2012 | Weber |
| 8,268,783 B2 | 9/2012 | Conley |
| 8,318,714 B2 | 11/2012 | Zhang |
| 8,337,888 B2 | 12/2012 | Wright |
| 8,337,890 B2 | 12/2012 | Tu |
| 8,367,651 B2 | 2/2013 | Zhang |
| 8,389,007 B2 | 3/2013 | Wright |
| 8,409,616 B2 | 4/2013 | Wadgaonkar |
| 8,425,933 B2 | 4/2013 | Mehta |
| 8,455,439 B2 | 6/2013 | Sinha |
| 8,455,441 B2 | 6/2013 | Sinha |
| 8,486,448 B2 | 7/2013 | Ferrada |
| 8,486,449 B2 | 7/2013 | Rahmouni |
| 8,491,935 B2 | 7/2013 | Tu |
| 8,518,443 B2 | 8/2013 | Wright |
| 8,524,275 B2 | 9/2013 | Oshlack |
| 8,529,948 B1 | 9/2013 | Wright |
| 8,597,684 B2 | 12/2013 | Tu |
| 8,603,526 B2 | 12/2013 | Olsen |
| 8,609,683 B2 | 12/2013 | Wright |
| 8,618,087 B2 | 12/2013 | Zhang |
| 8,637,540 B2 | 1/2014 | Wadgaonkar |
| 8,652,497 B2 | 2/2014 | Sackler |
| 8,652,515 B2 | 2/2014 | Sackler |
| 8,685,447 B2 | 4/2014 | Sant |
| 8,691,270 B2 | 4/2014 | Sant |
| 8,703,186 B2 | 4/2014 | Mehta |
| 8,747,902 B2 | 6/2014 | Tu |
| 8,765,675 B2 | 7/2014 | Christiansen |
| 8,771,730 B2 | 7/2014 | Navon |
| 8,790,700 B2 | 7/2014 | Tu |
| 8,815,287 B2 | 8/2014 | Wright |
| 8,822,489 B2 | 9/2014 | Wadgaonkar |
| 8,846,104 B2 | 9/2014 | Boehm |
| 8,871,265 B2 | 10/2014 | Wright |
| 8,877,247 B2 | 11/2014 | Boehm |
| 8,883,217 B2 | 11/2014 | Tu |
| 8,889,129 B2 | 11/2014 | Sinha |
| 8,916,588 B2 | 12/2014 | Lickrish |
| 8,920,833 B2 | 12/2014 | Sant |
| 8,920,834 B2 | 12/2014 | Sant |
| 8,927,010 B2 | 1/2015 | Lickrish |
| 8,927,013 B2 | 1/2015 | Sant |
| 8,927,014 B2 | 1/2015 | Sant |
| 8,999,961 B2 | 4/2015 | Wright |
| 9,005,660 B2 | 4/2015 | Oestman |
| 9,023,389 B1 | 5/2015 | Lickrish |
| 9,028,868 B2 | 5/2015 | Lickrish |
| 9,029,355 B2 | 5/2015 | Zhang |
| 9,034,376 B2 | 5/2015 | Wright |
| 9,034,902 B2 | 5/2015 | Lickrish |
| 9,040,084 B2 | 5/2015 | Wright |
| 9,044,435 B2 | 6/2015 | Wright |
| 9,056,054 B2 | 6/2015 | Dick |
| 9,056,116 B2 | 6/2015 | Zhang |
| 9,060,976 B2 | 6/2015 | Wright |
| 9,062,298 B2 | 6/2015 | Sinha |
| 9,072,663 B2 | 7/2015 | Navon |
| 9,096,656 B2 | 8/2015 | Mei |
| 9,101,636 B2 | 8/2015 | Hollenbeck |
| 9,101,668 B2 | 8/2015 | Oshlack |
| 9,109,046 B2 | 8/2015 | Conley |
| 9,119,809 B2 | 9/2015 | Lickrish |
| 9,155,717 B2 | 10/2015 | Sackler |
| 9,168,228 B2 | 10/2015 | Olsen |
| RE45,822 E | 12/2015 | Carpanzano |
| 9,198,864 B2 | 12/2015 | Tu |
| 9,198,867 B2 | 12/2015 | Bosse |
| 9,211,292 B2 | 12/2015 | Kavesh |
| 9,226,901 B2 | 1/2016 | Bosse |
| 9,259,387 B2 | 2/2016 | Navon |
| 9,283,214 B2 | 3/2016 | Lickrish |
| 9,289,394 B2 | 3/2016 | Lickrish |
| 9,301,918 B2 | 4/2016 | Raman |
| 9,308,170 B2 | 4/2016 | Wright |
| 9,308,171 B2 | 4/2016 | Wright |
| 9,320,796 B2 | 4/2016 | Hollenbeck |
| 9,326,954 B2 | 5/2016 | Sackler |
| 9,358,295 B2 | 6/2016 | Oestman |
| 9,364,520 B2 | 6/2016 | Mei |
| 9,387,173 B2 | 7/2016 | Wright |
| 9,387,174 B2 | 7/2016 | Wright |
| 9,387,177 B2 | 7/2016 | Bosse |
| 9,388,401 B2 | 7/2016 | Lu |
| 2003/0044458 A1 | 3/2003 | Carpanzano |
| 2003/0064099 A1 | 4/2003 | Wright |
| 2003/0068370 A1 | 4/2003 | Sackler |
| 2003/0068371 A1 | 4/2003 | Wright |
| 2003/0068375 A1 | 4/2003 | Wright |
| 2003/0068392 A1 | 4/2003 | Sackler |
| 2003/0073714 A1 | 4/2003 | Wright |
| 2003/0124185 A1 | 7/2003 | Wright |
| 2003/0232081 A1 | 12/2003 | Joshi |
| 2004/0202717 A1 | 10/2004 | Mehta |
| 2005/0063909 A1 | 3/2005 | Carpanzano |
| 2005/0112067 A1 | 5/2005 | Wadgaonkar |
| 2005/0163856 A1* | 7/2005 | Maloney ............... A61K 9/2054 424/486 |
| 2005/0265955 A1* | 12/2005 | Raman ................. A61K 9/0095 424/78.12 |
| 2006/0062856 A1 | 3/2006 | McGee |
| 2006/0093671 A1 | 5/2006 | McGee |
| 2006/0115876 A1 | 6/2006 | Mei |
| 2006/0194722 A1 | 8/2006 | Christiansen |
| 2007/0014732 A1 | 1/2007 | Sackler |
| 2007/0020188 A1 | 1/2007 | Sackler |
| 2007/0141161 A1 | 6/2007 | Zhang |
| 2007/0148252 A1 | 6/2007 | Zhang |
| 2007/0166234 A1 | 7/2007 | Wadgaonkar |
| 2007/0202049 A1* | 8/2007 | Guimberteau ....... A61K 9/5047 424/10.2 |
| 2007/0215511 A1 | 9/2007 | Tu |
| 2007/0264327 A1 | 11/2007 | Wadgaonkar |
| 2008/0166405 A1 | 7/2008 | Mehta |
| 2008/0233197 A1 | 9/2008 | Garth |
| 2009/0004292 A1 | 1/2009 | Wadgaonkar |
| 2009/0011028 A1 | 1/2009 | Checot |
| 2009/0081287 A1 | 3/2009 | Wright |
| 2009/0098119 A1 | 4/2009 | Phillips |
| 2009/0162450 A1 | 6/2009 | Boehm |
| 2009/0162451 A1 | 6/2009 | Boehm |
| 2009/0175937 A1 | 7/2009 | Sant |
| 2009/0175939 A1 | 7/2009 | Bosse |
| 2009/0238868 A1 | 9/2009 | Mehta |
| 2009/0253730 A1 | 10/2009 | Wadgaonkar |
| 2010/0081615 A1 | 4/2010 | Mei |
| 2010/0098771 A1 | 4/2010 | Mehta |
| 2010/0125052 A1 | 5/2010 | Sinha |
| 2010/0143483 A1 | 6/2010 | Boehm |
| 2010/0166858 A1 | 7/2010 | Tu |
| 2010/0168148 A1 | 7/2010 | Wright |
| 2010/0203130 A1 | 8/2010 | Olsen |
| 2010/0204259 A1 | 8/2010 | Oestman |
| 2010/0216829 A2 | 8/2010 | Tewari |
| 2010/0225131 A1 | 9/2010 | Weber |
| 2010/0239662 A1 | 9/2010 | Sant |
| 2010/0255000 A1 | 10/2010 | Conley |
| 2010/0261713 A1 | 10/2010 | Sackler |

(56) References Cited

U.S. PATENT DOCUMENTS

| | | |
|---|---|---|
| 2010/0278881 A1 | 11/2010 | Christiansen |
| 2011/0002985 A1 | 1/2011 | Shah |
| 2011/0076325 A1 | 3/2011 | Shah |
| 2011/0091542 A1 | 4/2011 | Kluev |
| 2011/0117192 A1 | 5/2011 | Navon |
| 2011/0150969 A1 | 6/2011 | Shah |
| 2011/0150970 A1 | 6/2011 | Shah |
| 2011/0150971 A1 | 6/2011 | Shah |
| 2011/0150990 A1 | 6/2011 | Shah |
| 2011/0150991 A1 | 6/2011 | Shah |
| 2011/0159089 A1 | 6/2011 | Shah |
| 2011/0159090 A1 | 6/2011 | Shah |
| 2011/0184007 A1 | 7/2011 | Difalco |
| 2011/0230510 A1 | 9/2011 | Wright |
| 2011/0236487 A1 | 9/2011 | Zhang |
| 2011/0256226 A1 | 10/2011 | Wright |
| 2012/0015030 A1 | 1/2012 | Tu |
| 2012/0021051 A1 | 1/2012 | Kirmayer |
| 2012/0052098 A1 | 3/2012 | Zhang |
| 2012/0087982 A1 | 4/2012 | Wadgaonkar |
| 2012/0108622 A1 | 5/2012 | Wright |
| 2012/0135077 A1 | 5/2012 | Perumal |
| 2012/0148672 A1 | 6/2012 | Perumal |
| 2012/0156277 A1 | 6/2012 | Difalco |
| 2012/0164209 A1 | 6/2012 | Shah |
| 2012/0189705 A1 | 7/2012 | Boehm |
| 2012/0201761 A1 | 8/2012 | Sackler |
| 2012/0201888 A1 | 8/2012 | Bosse |
| 2012/0201895 A1 | 8/2012 | Matthews |
| 2012/0269788 A1 | 10/2012 | Sinha |
| 2012/0276017 A1 | 11/2012 | Lickrish |
| 2012/0288567 A1 | 11/2012 | Wright |
| 2013/0034503 A1 | 2/2013 | Kavesh |
| 2013/0059007 A1 | 3/2013 | Tu |
| 2013/0084333 A1 | 4/2013 | Dick |
| 2013/0129693 A1 | 5/2013 | Conley |
| 2013/0136797 A1 | 5/2013 | Tu |
| 2013/0156821 A1 | 6/2013 | Zhang |
| 2013/0171257 A1 | 7/2013 | Tewari |
| 2013/0217716 A1 | 8/2013 | Wright |
| 2013/0230596 A1 | 9/2013 | Mehta |
| 2013/0245055 A1 | 9/2013 | Wright |
| 2013/0261143 A1 | 10/2013 | Wright |
| 2013/0261144 A1 | 10/2013 | Wright |
| 2013/0261145 A1 | 10/2013 | Wright |
| 2013/0274445 A1 | 10/2013 | Pan |
| 2013/0287851 A1 | 10/2013 | Zhang |
| 2013/0289062 A1 | 10/2013 | Wadgaonkar |
| 2013/0303494 A1 | 11/2013 | Wright |
| 2013/0309303 A1 | 11/2013 | Wright |
| 2013/0317051 A1 | 11/2013 | Oshlack |
| 2013/0344142 A1 | 12/2013 | Sant |
| 2014/0004191 A1 | 1/2014 | Sant |
| 2014/0030322 A1 | 1/2014 | Bosse |
| 2014/0030334 A1 | 1/2014 | Tu |
| 2014/0044773 A1 | 2/2014 | Sinha |
| 2014/0050787 A1 | 2/2014 | Hoeilund Jensen |
| 2014/0056984 A1 | 2/2014 | Tu |
| 2014/0079684 A1 | 3/2014 | Sinha |
| 2014/0127306 A1 | 5/2014 | Tu |
| 2014/0134151 A1 | 5/2014 | Sinha |
| 2014/0154309 A1 | 6/2014 | Zhang |
| 2014/0155388 A1 | 6/2014 | Hollenbeck |
| 2014/0155425 A1 | 6/2014 | Sackler |
| 2014/0155426 A1 | 6/2014 | Sackler |
| 2014/0193494 A1 | 7/2014 | Sant |
| 2014/0212461 A1 | 7/2014 | Lickrish |
| 2014/0212483 A1 | 7/2014 | Lickrish |
| 2014/0213606 A1 | 7/2014 | Wright |
| 2014/0227197 A1 | 8/2014 | Lickrish |
| 2014/0228390 A1 | 8/2014 | Wright |
| 2014/0248343 A1 | 9/2014 | Difalco |
| 2014/0248344 A1 | 9/2014 | Difalco |
| 2014/0248346 A1 | 9/2014 | Sant |
| 2014/0271735 A1 | 9/2014 | Christiansen |
| 2014/0271849 A1 | 9/2014 | Raman |
| 2014/0294954 A1 | 10/2014 | Sant |
| 2014/0294955 A1 | 10/2014 | Sant |
| 2014/0314842 A1 | 10/2014 | Navon |
| 2014/0336213 A1 | 11/2014 | Wadgaonkar |
| 2014/0357657 A1 | 12/2014 | Wright |
| 2014/0371257 A1 | 12/2014 | Wright |
| 2014/0377352 A1 | 12/2014 | Difalco |
| 2015/0005331 A1 | 1/2015 | Wright |
| 2015/0005333 A1 | 1/2015 | Wright |
| 2015/0010624 A1 | 1/2015 | Navon |
| 2015/0024058 A1 | 1/2015 | Boehm |
| 2015/0024059 A1 | 1/2015 | Tu |
| 2015/0031718 A1 | 1/2015 | Wright |
| 2015/0044282 A1 | 2/2015 | Difalco |
| 2015/0057228 A1 | 2/2015 | Lu |
| 2015/0064245 A1 | 3/2015 | Difalco |
| 2015/0064246 A1 | 3/2015 | Difalco |
| 2015/0064247 A1 | 3/2015 | Difalco |
| 2015/0064248 A1 | 3/2015 | Difalco |
| 2015/0071995 A1 | 3/2015 | Difalco |
| 2015/0071998 A1 | 3/2015 | Difalco |
| 2015/0110868 A1 | 4/2015 | Lickrish |
| 2015/0110879 A1 | 4/2015 | Wright |
| 2015/0125521 A1 | 5/2015 | Lickrish |
| 2015/0140083 A1 | 5/2015 | Wright |
| 2015/0147391 A1 | 5/2015 | Wright |
| 2015/0148319 A1 | 5/2015 | Wright |
| 2015/0182628 A1 | 7/2015 | Wright |
| 2015/0231125 A1 | 8/2015 | Lickrish |
| 2015/0238443 A1 | 8/2015 | Lickrish |
| 2015/0238481 A1 | 8/2015 | Wright |
| 2015/0250732 A1 | 9/2015 | Dick |
| 2015/0265602 A1 | 9/2015 | Wright |
| 2015/0265603 A1 | 9/2015 | Wright |
| 2015/0265604 A1 | 9/2015 | Wright |
| 2015/0265605 A1 | 9/2015 | Wright |
| 2015/0265606 A1 | 9/2015 | Wright |
| 2015/0265607 A1 | 9/2015 | Wright |
| 2015/0272888 A1 | 10/2015 | Rahmouni |
| 2015/0272890 A1 | 10/2015 | Rahmouni |
| 2015/0272893 A1 | 10/2015 | Mehta |
| 2015/0273064 A1 | 10/2015 | Wright |
| 2015/0273065 A1 | 10/2015 | Wright |
| 2015/0283128 A1 | 10/2015 | Wright |
| 2015/0283129 A1 | 10/2015 | Wright |
| 2015/0283130 A1 | 10/2015 | Wright |
| 2015/0283250 A1 | 10/2015 | Wright |
| 2015/0297525 A1 | 10/2015 | Bosse |
| 2015/0306040 A1 | 10/2015 | Bosse |
| 2015/0313843 A1 | 11/2015 | Zhang |
| 2015/0313849 A1 | 11/2015 | Lickrish |
| 2015/0313997 A1 | 11/2015 | Oestman |
| 2015/0320685 A1 | 11/2015 | Bosse |
| 2015/0366816 A1 | 12/2015 | Lickrish |
| 2015/0366832 A1 | 12/2015 | Navon |
| 2015/0366861 A1 | 12/2015 | Sackler |
| 2015/0374628 A1 | 12/2015 | Wright |
| 2015/0374631 A1 | 12/2015 | Wright |
| 2015/0374821 A1 | 12/2015 | Hollenbeck |
| 2016/0000712 A1 | 1/2016 | Wright |
| 2016/0000717 A1 | 1/2016 | Wright |
| 2016/0000718 A1 | 1/2016 | Wright |
| 2016/0000719 A1 | 1/2016 | Wright |
| 2016/0000723 A1 | 1/2016 | Wright |
| 2016/0000776 A1 | 1/2016 | Wright |
| 2016/0002617 A1 | 1/2016 | Lu |
| 2016/0008350 A1 | 1/2016 | Oshlack |
| 2016/0051474 A1 | 2/2016 | Bosse |
| 2016/0051633 A1 | 2/2016 | Mei |
| 2016/0058716 A1 | 3/2016 | Wright |
| 2016/0074332 A1 | 3/2016 | Heilund Jensen |
| 2016/0106755 A1 | 4/2016 | Bosse |
| 2016/0151277 A1 | 6/2016 | Wright |
| 2016/0151289 A1 | 6/2016 | Wright |
| 2016/0151290 A1 | 6/2016 | Wright |
| 2016/0151291 A1 | 6/2016 | Wright |
| 2016/0151297 A1 | 6/2016 | Wright |
| 2016/0151355 A1 | 6/2016 | Wright |

(56) References Cited

U.S. PATENT DOCUMENTS

| | | |
|---|---|---|
| 2016/0151356 A1 | 6/2016 | Wright |
| 2016/0151357 A1 | 6/2016 | Wright |
| 2016/0151358 A1 | 6/2016 | Wright |
| 2016/0151360 A1 | 6/2016 | Wright |
| 2016/0151499 A1 | 6/2016 | Wright |
| 2016/0151502 A1 | 6/2016 | Wright |
| 2016/0158373 A1 | 6/2016 | Tu |
| 2016/0193156 A1 | 7/2016 | Lickrish |
| 2016/0199300 A1 | 7/2016 | Navon |
| 2016/0199312 A1 | 7/2016 | Lickrish |
| 2016/0199388 A1 | 7/2016 | Hollenbeck |

OTHER PUBLICATIONS

Shah et al. "Complexation between risperidone and amberlite resin by various methods of preparation and binding study," Drug Development and Industrial Pharmacy 35(12): 1409-1418 (2009).

Dow Amberlite™ and Duolite™ Ion Exchange Resin Excipients Handling and Use Guide, Form No. 177-03500-0413, Mar. 2013; Dow Chemical Company.

* cited by examiner

A

B

A

B

ANTI-OVERINGESTION DOSAGE FORMS

CROSS REFERENCE TO RELATED APPLICATIONS

This application claims priority to U.S. Provisional Patent Application No. 62/250,284, filed on Nov. 3, 2015, which is incorporated by reference herein in its entirety.

TECHNICAL FIELD

Described herein are abuse deterrent oral pharmaceutical compositions, methods for making the same, and methods of treatment using such compositions. In particular, oral pharmaceutical compositions that mitigate the risk of overingestion of one or more active pharmaceutical ingredients are described.

BACKGROUND

Increased attention has been drawn to the recreational use and abuse of prescription pharmaceutical compositions. The abuse, or non-medicinal use, of prescription pharmaceutical compositions is an increasing problem. Accordingly, preventing the abuse of prescription pharmaceuticals through the development of abuse deterrent pharmaceutical compositions has become a high public health priority for the U.S. Food and Drug Administration (FDA). Prescription pharmaceutical compositions that are typically misused or abused fall, primarily, into three groups: (1) opioids prescribed for pain; (2) Central Nervous System (CNS) depressants prescribed for anxiety or sleep problems; and (3) stimulants, prescribed, for example, for attention deficit hyperactivity, narcolepsy, or obesity.

Methods for abusing prescription pharmaceutical compositions are varied and can include, for example, extraction, boiling, melting, volatilization, physical tampering (e.g., grinding, grating, crushing, etc.), or direct administration. For purposes of abuse, methods of administering active drug substances obtained from prescription pharmaceutical compositions or of the pharmaceutical compositions themselves are similarly diverse and include, for example, injection, smoking, snorting, swallowing, sublingual or buccal administration, chewing, or administration as an anal or vaginal suppository. Alcohol-induced "dose dumping," i.e., the rapid release of active pharmaceutical ingredients in the presence of a solvent such as ethanol, is also an abuse concern and safety issue. Other methods include rapid extraction under aqueous boiling conditions.

There are a number of strategies for preventing the abuse of pharmaceuticals. Physical and chemical barriers can prevent the extraction of the drug or change the form of the drug making it less likely to be abused. Combinations of agonists and antagonists can be used, wherein the antagonist is only released upon product manipulation or tampering. Another strategy is to use aversive compounds that produce an unpleasant effect when the dosage form is tampered with. In addition, prodrugs can be used, which are only changed into the active form of the drug in the gastrointestinal tract. The pharmaceutical industry is utilizing these strategies to develop abuse-deterrent pharmaceutical compositions in order to reduce the potential for misuse of prescription pharmaceutical compositions.

There remains a need for abuse deterrent pharmaceutical compositions that comprise properties that mitigate the risk of accidental or intentional overingestion. In particular, there is a need for formulations that are resistant to active pharmaceutical ingredient extraction and that inhibit the risk of overingestion.

SUMMARY

One embodiment described herein is an oral immediate release pharmaceutical composition comprising a dry mixture comprising one or more active pharmaceutical ingredients (API), one or more sequestering agents, and optionally, one or more pharmaceutically acceptable excipients, where less than about 1% of the API is bound to the sequestering agent. In one aspect, upon ingestion of at least one dose by a subject, the sequestering agent adsorbs a quantity of the API and impedes its absorption into the subject's systemic circulation. In another aspect, the quantity of the API adsorbed by the sequestering agent is about 0.5% to about 15%. In another aspect, a greater quantity of API is adsorbed by the sequestering agent when a plurality of doses of the composition are simultaneously ingested or successively ingested over about a 4-hour period. In another aspect, the quantity of the API adsorbed by the sequestering agent is about 15% to about 70%. In another aspect, the plurality of doses is 2 or greater. In another aspect, the plurality of doses is from 2 to 30. In another aspect, the composition is capable of achieving one or more of the following pharmacokinetic parameters: (a) a lower $C_{max}$ for the API as compared to an equivalent API dose lacking a sequestering agent; (b) a delayed $T_{max}$ for the API as compared to an equivalent API dose lacking a sequestering agent; (c) a similar plasma AUC for the API as compared to an equivalent API dose lacking a sequestering agent; (d) an extended absorption time for the API as compared to an equivalent API dose lacking a sequestering agent; or (e) an extended clearance time for the API as compared to an equivalent API dose lacking a sequestering agent. In another aspect, the API to sequestering agent comprises a mass ratio of about 1:2 to about 1:8. In another aspect, the API to sequestering agent comprises a mass ratio of about 1:3 to about 1:5. In another aspect, the API to sequestering agent comprises a mass ratio of about 1:4. In another aspect, the API comprises an opioid. In another aspect, the API comprises hydrocodone, oxycodone, oxymorphone, hydromorphone, morphine, codeine, salts thereof, or combinations thereof. In another aspect, the API comprises hydrocodone bitartrate. In another aspect, the sequestering agent comprises one or more ion exchange polymers. In another aspect, the sequestering agent comprises one or more cation exchange polymers or salts thereof. In another aspect, the sequestering agent comprises a sulfonated styrene and divinylbenzene copolymer or a salt thereof. In another aspect, the sequestering agent comprises polystyrene sulfonate or a salt thereof. In another aspect, the composition comprises a dry admixture of hydrocodone bitartrate and sodium polystyrene sulfonate at a mass ratio of about 1:4. In another aspect, the composition is non-layered. In another aspect, the composition comprises: about 10% to about 30% API; and about 70% to 90% sequestering agent. In another aspect, the composition comprises about 20% API; and about 80% sequestering agent. In another aspect, the composition comprises about 20% hydrocodone bitartrate; and about 80% polystyrene sulfonate or a salt thereof. In another aspect, the composition is encapsulated in a capsule or formed as a tablet. In another aspect, the composition exhibits an in vitro disintegration or dissolution rate comprising about 50% disintegration or dissolution after about 1 minute to about 15 minutes at pH 1.2.

Another embodiment described herein is an oral immediate release pharmaceutical composition comprising a dry mixture of hydrocodone or a salt thereof and polystyrene sulfonate or a salt thereof in a mass ratio of about 1:2 to about 1:8, where less than about 1% of the hydrocodone is bound to the polystyrene sulfonate. In one aspect, upon ingestion of at least one dose by a subject, the polystyrene sulfonate adsorbs a quantity of the hydrocodone and impedes its absorption into the subject's systemic circulation. In another aspect, the quantity of hydrocodone adsorbed by the polystyrene sulfonate is about 0.5% to about 15%. In another aspect, a greater quantity of hydrocodone is adsorbed by the polystyrene sulfonate when a plurality of doses of the composition are simultaneously ingested or successively ingested over about a 4-hour period. In another aspect, the quantity of hydrocodone adsorbed by the polystyrene sulfonate is about 15% to about 70%. In another aspect, the plurality of doses is 2 or greater. In another aspect, the plurality of doses is from 2 to 30. In another aspect, the composition is capable of achieving one or more of the following pharmacokinetic parameters: (a) a lower $C_{max}$ for the hydrocodone as compared to an equivalent hydrocodone dose lacking polystyrene sulfonate t; (b) a delayed $T_{max}$ for hydrocodone as compared to an equivalent hydrocodone dose lacking polystyrene sulfonate; (c) a similar plasma AUC for hydrocodone as compared to an equivalent hydrocodone dose lacking polystyrene sulfonate; (d) an extended absorption time for hydrocodone as compared to an equivalent hydrocodone dose lacking polystyrene sulfonate; or (e) an extended clearance time for hydrocodone as compared to an equivalent hydrocodone dose lacking polystyrene sulfonate. In another aspect, the composition comprises a non-layered powder suspension. In another aspect, the mass ratio of hydrocodone to polystyrene sulfonate is about 1:4. In another aspect, the composition exhibits an in vitro disintegration or dissolution rate comprising about 50% disintegration or dissolution after about 1 minute to about 15 minutes at pH 1.2. Another aspect is a dosage form comprising the foregoing composition described herein encapsulated in a capsule or formed as a tablet.

Another embodiment described herein is a method for treating pain while mitigating the risk of overingestion, the method comprising administering to a subject in need thereof an oral immediate release pharmaceutical composition comprising a dry mixture of one or more active pharmaceutical ingredients (API), one or more sequestering agents, and optionally, one or more pharmaceutically acceptable excipients, where less than 1% of the API is bound to the sequestering agent, and following ingestion of at least one dose by a subject, the sequestering agent adsorbs a quantity of the API and impedes its release into the subject's systemic circulation. In one aspect, the API to sequestering agent mass ratio is about 1:2 to about 1:8. In another aspect, the quantity of the API adsorbed by the sequestering agent is about 0.5% to about 15%. In another aspect, a greater quantity of API is adsorbed by the sequestering agent when a plurality of doses of the composition are simultaneously ingested or successively ingested over about a 4-hour period. In another aspect, the quantity of the API adsorbed by the sequestering agent is about 15% to about 70%. In another aspect, the plurality of doses is 2 or greater. In another aspect, the plurality of doses is from 2 to 30. In another aspect, the composition is capable of achieving one or more of the following pharmacokinetic parameters: (a) a lower $C_{max}$ for the API as compared to an equivalent API dose lacking a sequestering agent; (b) a delayed $T_{max}$ for the API as compared to an equivalent API dose lacking a sequestering agent; (c) a similar plasma AUC for the API as compared to an equivalent API dose lacking a sequestering agent; or (d) an extended clearance time for the API as compared to an equivalent API dose lacking a sequestering agent. In another aspect, the API comprises hydrocodone, oxycodone, oxymorphone, hydromorphone, morphine, codeine, salts thereof, or combinations thereof. In another aspect, the sequestering agent comprises one or more ion exchange polymers. In another aspect, the composition comprises a dry powder suspension of hydrocodone bitartrate and sodium polystyrene sulfonate at a mass ratio of about 1:4. In another aspect, the composition is a non-layered. In another aspect, the composition comprises about 10% to about 30% API; and about 70% to 90% sequestering agent. In another aspect, the composition comprises about 20% API; and about 80% sequestering agent. In another aspect, the composition comprises about 20% hydrocodone bitartrate; and about 80% polystyrene sulfonate or a salt thereof. In another aspect, the composition is encapsulated in a capsule or formed as a tablet. In another aspect, the composition exhibits an in vitro disintegration or dissolution rate comprising about 50% disintegration or dissolution after about 1 minute to about 15 minutes at pH 1.2. In another aspect, the pain arises from one or more of diabetic neuropathy, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica, granuloma annulare, trauma, cancer, or a combination thereof.

Another embodiment described herein is method for mitigating the risk of overingestion, the method comprising administering to a subject in need thereof one or more oral immediate release pharmaceutical compositions comprising one or more active pharmaceutical ingredients (API), one or more sequestering agents, and optionally, one or more pharmaceutically acceptable excipients, where less than about 1% of the API is bound to the sequestering agent, and following ingestion of at least one dose by a subject, the sequestering agent adsorbs a quantity of the API and impedes its release into the subject's systemic circulation. In one aspect, the API to sequestering agent mass ratio is about 1:2 to about 1:8. In another aspect, the quantity of the API adsorbed by the sequestering agent is about 0.5% to about 15%. In another aspect, a greater quantity of API is adsorbed by the sequestering agent when a plurality of doses of the composition are simultaneously ingested or successively ingested over about a 4-hour period. In another aspect, the quantity of the API adsorbed by the sequestering agent is about 15% to about 70%. In another aspect, the plurality of doses is 2 or greater. In another aspect, the plurality of doses is from 2 to 30. In another aspect, the composition is capable of achieving one or more of the following pharmacokinetic parameters: (a) a lower $C_{max}$ for the API as compared to an equivalent API dose lacking a sequestering agent; (b) a delayed $T_{max}$ for the API as compared to an equivalent API dose lacking a sequestering agent; (c) a similar plasma AUC for the API as compared to an equivalent API dose lacking a sequestering agent; or (d) an extended clearance time for the API as compared to an equivalent API dose lacking a sequestering agent. In another aspect, the API comprises hydrocodone, oxycodone, oxymorphone, hydromorphone, morphine, codeine, salts thereof, or combinations thereof. In another aspect, the sequestering agent comprises one or more ion exchange polymers. In another aspect, the composition comprises a dry powder suspension of hydrocodone bitartrate and sodium polystyrene sulfonate at a mass ratio of about 1:4. In another aspect, the composition is a non-layered. In another aspect, the composition comprises about 10% to about 30% API; and about 70% to 90% sequestering agent. In another aspect, the composition comprises about 20% API; and about 80% sequestering agent. In another aspect, the composition comprises about 20% hydrocodone bitartrate; and about 80% polystyrene sulfonate or a salt thereof. In another aspect, the composition is encapsulated in a capsule or formed as a tablet. In another aspect, the composition exhibits an in vitro disintegration or dissolution rate comprising about 50% disintegration or dissolution after about 1 minute to about 15 minutes at pH 1.2.

Another embodiment described herein is a method for manufacturing an overingestion-inhibiting pharmaceutical dosage form, the method comprising (i) combining one or more active pharmaceutical ingredients (API) with one or more sequestering agents, and optionally one or more pharmaceutically acceptable excipients to form a powder suspension; and (ii) forming a dosage form from the powder suspension. In one aspect, less than about 1% of the API is bound to the sequestering agent. In another aspect, the API to sequestering agent mass ratio is about 1:2 to about 1:8. Another aspect is a dosage form produced by the manufacturing method described herein. In another aspect, the dosage form comprises an API comprising an opioid or a salt thereof and the sequestering agent comprises an ion exchange resin or a salt thereof. In another aspect, the dosage form is a capsule or a tablet. In another aspect, the dosage form exhibits an in vitro disintegration or dissolution rate comprising about 50% disintegration or dissolution after about 1 minute to about 15 minutes at pH 1.2.

Another embodiment described herein is a kit comprising one or more dosage forms comprising one or more oral immediate release pharmaceutical composition comprising one or more active pharmaceutical ingredients (API), one or more sequestering agents, and optionally, one or more pharmaceutically acceptable excipients, wherein less than about 1% of the API is bound to the sequestering agent, and following ingestion of at least one dose by a subject, the sequestering agent adsorbs a quantity of the API and impedes its release into systemic circulation; (b) one or more moisture proof dispensing receptacles; and optionally (c) an insert comprising instructions, prescribing information, contraindications, or warnings.

Another embodiment described herein is a method for regulating the concentration of an active pharmaceutical ingredient in a subject's systemic circulation, the method comprising administering to a subject one or more oral immediate release pharmaceutical compositions comprising one or more active pharmaceutical ingredients (API), one or more sequestering agents, and optionally, one or more pharmaceutically acceptable excipients, where less than about 1% of the API is bound to the sequestering agent, and following ingestion of at least one dose by a subject, the sequestering agent adsorbs a quantity of the API and impedes its release into the subject's systemic circulation. In another aspect, the API to sequestering agent mass ratio is about 1:2 to about 1:8. In another aspect, the quantity of the API adsorbed by the sequestering agent is about 0.5% to about 15%. In another aspect, a greater quantity of API is adsorbed by the sequestering agent when a plurality of doses of the composition are simultaneously ingested or successively ingested over about a 4-hour period. In another aspect, the quantity of the API adsorbed by the sequestering agent is about 15% to about 70%. In another aspect, the plurality of doses is 2 or greater. In another aspect, the plurality of doses is from 2 to 30. In another aspect, the composition is capable of achieving one or more of the following pharmacokinetic parameters: (a) a lower $C_{max}$ for the API as compared to an equivalent API dose lacking a sequestering agent; (b) a delayed $T_{max}$ for the API as compared to an equivalent API dose lacking a sequestering agent; (c) a similar plasma AUC for the API as compared to an equivalent API dose lacking a sequestering agent; or (d) an extended clearance time for the API as compared to an equivalent API dose lacking a sequestering agent. In another aspect, the sequestering agent comprises one or more ion exchange polymers. In another aspect, the composition is a non-layered. In another aspect, the composition comprises about 10% to about 30% API; and about 70% to 90% sequestering agent. In another aspect, the composition comprises about 20% API; and about 80% sequestering agent. In another aspect, the composition is encapsulated in a capsule or formed as a tablet. In another aspect, the composition exhibits an in vitro disintegration or dissolution rate comprising about 50% disintegration or dissolution after about 1 minute to about 15 minutes at pH 1.2. In another aspect, the method further comprises: (a) acquiring a bodily fluid from the subject; (b) measuring the concentration of the API in the subject's circulation; and (c) according to the measured API concentration and a desired optimal API therapeutic concentration, either: (i) administering one or more doses of the composition comprising the API and a sequestering agent; (ii) administering an equivalent dose of the API comprising a composition lacking a sequestering agent; or (iii) administering either one or more doses of the composition comprising the API and a sequestering agent or administering an equivalent dose of the API comprising a composition lacking a sequestering agent after a period of about 30 min to about 12 hours.

Another embodiment described herein is a pharmaceutical composition comprising an abuse deterrent controlled release composition comprising one or more active pharmaceutical ingredients that prevent over ingestion of abuse prone drugs. The composition is structured to prevent extraction of the active pharmaceutical ingredients. The composition formulations described herein minimize the likelihood of tampering, "dose dumping," or the extraction of active pharmaceutical ingredients from the composition. Further, the composition is structured to reduce the release of one or more active pharmaceutical ingredients when multiple pharmaceutical compositions are ingested.

One embodiment described herein is an abuse deterrent oral pharmaceutical composition comprising a tamper resistant controlled release composition, wherein the tamper resistant controlled release composition comprises a means for preventing the crushing, grating, grinding, cutting, solvating, or dissolving of the tamper resistant controlled release composition comprising one or more active pharmaceutical ingredients. In one aspect, the abuse deterrent oral pharmaceutical composition comprises a means for preventing the over ingestion of one or more active pharmaceutical ingredients when more than the recommended dosage is taken.

Another embodiment described herein is an anti-overingestion abuse deterrent pharmaceutical composition comprising a soft capsule shell composition comprising a first one or more ionically charged polymers, wherein the soft capsule shell encapsulates a composition comprising one or more active pharmaceutical ingredients and a second one or more ionically charged polymers, wherein the one or more active pharmaceutical ingredients is in a pH responsive resinate complex with the second one or more ionically charged polymers. In one aspect described herein, the soft capsule shells described herein comprise two or more soft capsule shell sub compositions that comprise a total soft capsule shell composition, wherein the two or more soft capsule shell sub compositions are spatially separated. In another aspect, the one or more ionically charged polymers comprises at least two ionically charged polymers. In another aspect, the total soft capsule shell composition comprises a first soft capsule shell sub composition and a second soft capsule shell sub composition. In another aspect, the at least two ionically charged polymers comprise at least one positively charged polymer and at least one negatively charged polymer. In another aspect, each one of the at least two ionically charged polymers are each in the at least two or more of the soft capsule shell sub compositions. In another aspect, the first soft capsule shell sub composition comprises about 1% to about 90% of the total soft capsule shell composition. In another aspect, the second soft capsule shell sub composition comprises about 1% to about 90% of the total soft capsule shell composition. In another aspect, the first soft capsule shell sub composition comprises a positively charged polymer. In another aspect, the second soft capsule shell sub composition comprises a negatively charged polymer. In another aspect, the positively charged polymer comprises a dimethylaminoethyl methacrylate copolymer. In another aspect, the negatively charged polymer comprises a methacrylic acid copolymer. In another aspect, the positively charged polymer comprises about 1% to about 25% of at least one of the soft capsule shell sub compositions. In another aspect, the negatively charged polymer comprises about 1% to about 25% of at least one of the soft capsule shell sub compositions. In another aspect, the soft capsule shell further comprises one or more adhesive polymers. In another aspect, the one or more adhesive polymers comprises polycarbophil, xanthan gum, Carbopol® 1342P, Carbopol® 974P, chitosan, Carbopol® 971P, hydroxypropylmethyl cellulose (e.g., Methocel K100M or Methocel K15M), sodium carboxymethyl cellulose, hydroxypropylmethyl cellulose (Methocel K15M), gelatin, or acacia gum, or a combination thereof. In another aspect, the one or more adhesive polymers comprises about 0.5%-20% of the soft capsule shell. In another aspect, the soft capsule shell further comprises one or more thermoresponsive polymers. In another aspect, the one or more thermoresponsive polymers comprises poly(N-isopropylacrylamide), amine terminated poly(N-isopropylacrylamide), carboxylic acid terminated poly(N-isopropylacrylamide), poly(N-isopropylacrylamide-co-methacrylic acid), or poly(N-isopropylacrylamide-co-methacrylic acid-co-octadecyl acrylate), or a combination thereof. In another aspect, the soft capsule shell composition further comprises one or more film forming polymers, one or more plasticizers, a solvent, and optionally, an alkaline neutralizing agent, an acidic neutralizing agent, a coloring agent, a flavoring or a pharmaceutical excipient. In another aspect, each of the soft capsule shell sub compositions comprises: (a) about 20% to about 36% by weight of at least one film-forming polymer; (b) about 1% to about 25% by weight of one or more ionically charged polymers; (c) about 1% to about 20% by weight of at least one plasticizer; (d) about 10% to about 40% by weight of a solvent; (e) optionally about 1% to about 5% by weight of at least one alkali-neutralizing agent; (f) optionally about 1% to about 5% by weight of at least one acidic neutralizing agent; (g) optionally about 1% to about 5% by weight of an opacifying agent; and (h) optionally about 0.05% to about 1% by weight of at least one coloring agent. In another aspect, at least one of the soft capsule shell sub compositions comprises: (a) about 30% by weight of at least one film-forming polymer; (b) about 10% by weight of at least one negatively charged polymer; (c) about 20% by weight of at least one plasticizer; (d) about 1% by weight of at least one alkali-neutralizing agent; (e) about 37% by weight of a solvent; and (f) optionally about 1.5% by weight of an opacifying agent; and (g) optionally about 0.05% to about 1% by weight of at least one coloring agent. In another aspect, at least one of the soft capsule shell sub compositions comprises: (a) about 25% by weight of at least one film-forming polymer; (b) about 12% by weight of at least one positively charged polymer; (c) about 17% by weight of at least one plasticizer; (d) about 1% by weight of at least one acidic neutralizing agent; (e) about 44% by weight of a solvent; and (f) optionally about 1.5% by weight of an opacifying agent; and (g) optionally about 0.05% to about 1% by weight of at least one coloring agent. In another aspect, the at least one soft capsule shell sub composition comprises gelatin, acrylic methacrylate copolymers, glycerol, triethyl citrate, ammonia, water, and optionally titanium dioxide. In another aspect, the at least one soft capsule shell sub composition comprises gelatin, dimethylaminoethyl methacrylate copolymer, glycerol, hydrochloric acid, water, and optionally titanium dioxide. In another aspect, the composition comprises one or more active pharmaceutical ingredients and one or more ionically charged polymers, wherein the one or more active pharmaceutical ingredients is in a pH responsive resinate complex with the one or more ionically charged polymers. In another aspect, the pH responsive resinate complex comprises one or more positively charged polymers or one or more negatively charged polymers or a combination of positively or negatively charged polymers thereof. In another aspect, the pH responsive resinate complex comprises a cation exchange resin or an anion exchange resin or a combination thereof. In another aspect, the cation exchange resin or anion exchange resin comprises an average particle size of about 1 µm to about 500 µm. In another aspect, the cation exchange resin or anion exchange resin comprises an ion exchange capacity of about 1 meq/g to about 6 meq/g. In another aspect, the cation exchange resin comprises a weak cation exchange resin or a strong cation exchange resin. In another aspect, the cation exchange resin comprises a polymer based on repeating alkyl or heteroalkyl units that may be optionally crosslinked and comprise functional groups comprising a sodium polystyrene sulfonate or a carboxylic acid group. In another aspect, the cation exchange resin comprises Amberlite™ IRP 69 or Amberlite™ IRP 88 or a combination thereof. In another aspect, the anion exchange resin comprises a polymer based on repeating branched or unbranched alkyl or heteroalkyl units that may be optionally crosslinked comprising functional groups comprising a primary amine or a quaternary ammonium. In another aspect, the one or more active pharmaceutical ingredients is positively charged or negatively charged and forms a complex with the cation exchange resin or anion exchange resin based upon an intermolecular ionic interaction with the one or more ionically charged polymers. In another aspect, the one or more active pharmaceutical ingredients is in complex with the resinate complex at a normal pH and disassociates from the resinate complex at a pH range found in the stomach. In another aspect, the composition further comprises one or more adhesive polymers. In another aspect, the one or more adhesive polymers comprises polycarbophil, xanthan gum, Carbopol® 1342P, Carbopol® 974P, chitosan, Carbopol® 971P, hydroxypropylmethyl cellulose (e.g., Methocel K100M or Methocel K15M), sodium carboxymethyl cellulose, hydroxypropylmethyl cellulose (Methocel K15M), gelatin, or acacia gum, or a combination thereof. In another aspect, the one or more adhesive polymers comprises polycarbophil. In another aspect, the composition further comprises: (a) a liquid lipid vehicle; (b) a semi solid lipid or lipophilic vehicle; (c) at least one ionic hydrophilic polymer; (d) at least one hydroscopic polymer; and (e) a suspension agent; and (f) optionally a non-ionic surfactant; and (g) optionally a pH-buffering agent In another aspect, the composition comprises: (a) soybean oil; (b) polyethylene glycol glyceride ester; (c) bee's wax; (d) polyvinylpyrrolidone or polyethylene oxide; (e) carbomer polymer; (g) dimethylaminoethyl methacrylate copolymer; (g) fumed silica; and (h) optionally a poloxamer non-ionic surfactant; and (I) optionally N-methyl-D-glucamine. In another aspect, the composition comprises: (a) about 45% to about 52% soybean oil; (b) about 1.5% to about 5% Gelucire® 43/01; (c) about 1.8% to about 4% bee's wax; (d) about 2% to about 8% Kollidon® 90 F; (e) about 0.5% to about 4% Carbopol® 971 A; (f) about 2% to about 8% EUDRAGIT® EPO; (g) about 0.5% to about 5% Aerosil 200; and (h) optionally about 1% to about 10% Pluronic® F127; and (i) optionally about 0.5% to about 6% N-methyl-D-glucamine. In another aspect, the composition further comprises: (a) one or more hydrophilic vehicles; (b) at least one carbomer polymers; (c) at least one hydroscopic polymer; (c) at least one hydrophilic polymer; (d) at least one ion exchange resin. In another aspect, the composition comprises: (a) polyethylene glycol 600 (b) polyethylene glycol 1000; (b) Carbopol® 974P; (c) polyvinylpyrrolidone; (c) hydroxypropylmethyl cellulose; and (d) at least one cation exchange resin. In another aspect, the composition comprises: (a) about 40% to about 70% polyethylene glycol 600 (b) about 2% to about 15% polyethylene glycol 1000; (b) about 0.25% to about 3% Carbopol® 974P; (c) about 2% to about 20% polyvinylpyrrolidone K90; (c) about 2% to about 20% hydroxypropylmethyl cellulose K100M; and (d) about 1% to about 20% of at least one cation exchange resins in complex with one or more active pharmaceutical ingredients. In another aspect, the at least one cation exchange resin comprises Amberlite™ IRP 69 or Amberlite™ IRP 88 or a combination thereof. In another aspect, the pharmaceutical composition further comprises a means for having gastro-retentive properties. In another aspect, the means for having gastro-retentive properties comprises a means for floating the pharmaceutical composition in a gastric compartment. In another aspect, the means for floating the pharmaceutical composition in a gastric compartment comprises the inclusion of one or more of an effervescent gas generating system, a colloidal gel barrier, porous beads, a microporous membrane, or the inclusion of one or more low-density excipients to the pharmaceutical composition.

DETAILED DESCRIPTION

Figure 1:
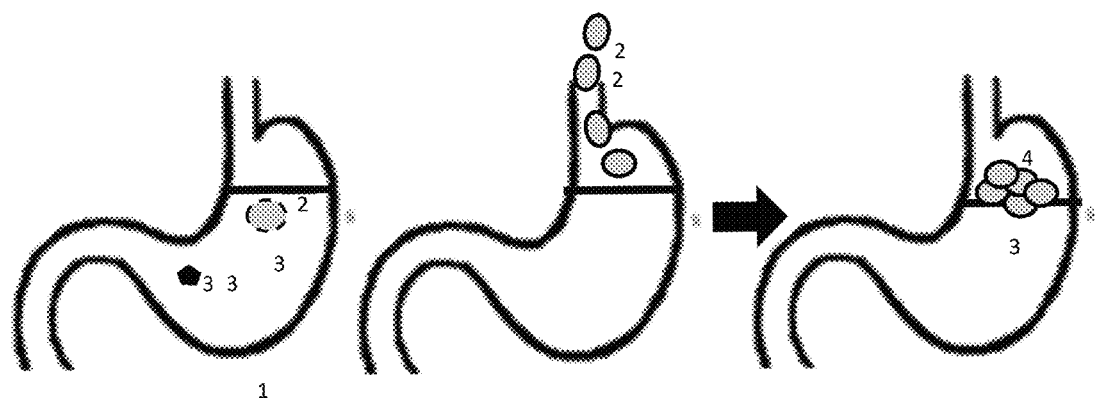
FIG. 1. Illustration of the anti-overingestion properties of the pharmaceutical compositions.

Described herein are abuse deterrent pharmaceutical compositions that can abrogate oral overingestion of large quantities of active pharmaceutical ingredients accidentally or purposely imbibed by a subject. The pharmaceutical compositions described herein provide abuse deterrent compositions and methods for preparation thereof. The compositions can be solids or liquids and delivered as tablets, hard capsules, soft capsules, or enteric dosage forms.

The term "abuse deterrent," or "tamper resistant" as used herein, refers to a pharmaceutical composition that is resistant to tampering or accessing the active pharmaceutical ingredient for recreational drug use or drug abuse. The term abuse deterrent further encompasses the term "anti-overingestion."

The term "anti-overingestion" refers to the prevention or mitigation of oral over ingesting greater than one dose of an active pharmaceutical ingredient when multiple dosage forms are taken simultaneously or in succession prior to gastric emptying, so that high levels of the drug are systemically absorbed. As used herein, anti-overingestion can mitigate both oral abuse of an active pharmaceutical agent for its euphoric or dissociative effects, or alternatively mitigate intentional or accidental overdose that could lead to adverse health effects such as depressed respiration, comma, cardiac arrest, or death.

The phrase "recreational drug use," as used herein, refers to the voluntary use of an active pharmaceutical agent or drug for a non-medical purpose to induce an effect, such as pleasure, satisfaction, euphoria, dissociation, or to enhance an experience.

The term "drug abuse," as use herein, refers to the habitual, compulsive, or recurrent use of an active pharmaceutical agent or drug, often despite negative consequences.

The phrases "oral abuse" or "oral drug abuse" refer to the intentional or accidental oral ingestion of greater than the prescribed or recommended dose of an active pharmaceutical agent by ingesting multiple dosage forms simultaneously or successively over a period of time. Oral abuse as used herein is distinguished from other abusive administration routes such as insufflation, injection, or ingestion of an extracted or tampered active pharmaceutical ingredient. Oral abuse is difficult to counteract or prevent because abuse is predicated on multiple dosage forms being ingested through the normal or appropriate route of administration.

The term "tampering," as used herein, refers to any kind of actual or attempted physical manipulation or interference that may result in particle size reduction of a pharmaceutical composition. Tampering, as used herein also includes any actual or attempted dissolution or extraction of active pharmaceutical ingredients using solvents. Compositions that are resistant to physical tampering are formulated in such a way that the composition cannot readily reduced to a form that is suitable for abuse, such as, for example, injection or snorting, because the tablet cannot easily be ground, grated, dissolved, extracted, and the like at any temperature. Examples of physical tampering include, but are not limited to, crushing, grinding, grating, cutting, crisping, and other methods of particle size reduction. Dissolution tampering includes actual or attempted actions to dissolve or extract active pharmaceutical ingredients using aqueous or organic solvents such as water, ethanol, isopropanol, ethyl acetate, acetone, ether, or the like, at any temperature including boiling. Tampering, as used herein, includes "dose dumping."

The term "dose dumping" or "dumping" as used herein refers to the rapid release of the entire amount or a significant fraction of an active pharmaceutical ingredient or drug. Drug abusers often intentionally pursue dumping of a drug from the dosage form.

The terms "drug", "active ingredient," "active pharmaceutical ingredient," or "active pharmaceutical agent" as used herein refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

The terms "dosage" or "dose" denote any form of the active ingredient formulation that contains an amount sufficient to produce a therapeutic effect with a single administration. The dosage form used herein is for oral administration. The preferred oral dosage forms are soft capsules or enteric soft capsules.

The terms "active pharmaceutical ingredient load" or "drug load" as used herein refers to the quantity (mass) of the active pharmaceutical ingredient comprised in a single soft capsule fill.

The term "formulation" or "composition" as used herein refers to the active pharmaceutical ingredient or drug in combination with pharmaceutically acceptable excipients. This includes orally administrable formulations as well as formulations administrable by other means.

The term "titration" as used herein refers to the incremental increase in drug dosage to a level that provides the optimal therapeutic effect.

The term "controlled release" as used herein refers to a composition that does not immediately releases an active ingredient. "Controlled release" as used herein encompasses the terms "modified release," "sustained release," "extended release," and "delayed release."

The term "immediate release" as used herein refers to a composition that releases an active ingredient over a short period under physiological conditions or in an in vitro test.

The term "delayed" release" as used herein refers to a composition that releases an active ingredient after a period of time, for example minutes or hours, such that the active ingredient is not released initially. A delayed release composition may provide, for example, the release of a drug or active ingredient from a dosage form, after a certain period, under physiological conditions or in an in vitro test.

The term "modified release" as used herein refers to a composition that releases an active ingredient at a slower rate than does an immediate release formulation under physiological conditions or in an in vitro test.

The terms "extended release" or "sustained release" as used herein refers to a composition that releases an active ingredient according to a desired profile over an extended period under physiological conditions or in an in vitro test. By "extended period" it is meant a continuous period of time of at least about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically, over a period of about 18 hours under physiological conditions or in an in vitro assay.

As used herein, the phrase "abuse deterrent controlled release" refers to a pharmaceutical composition comprising components or a formulation that prevents liberation of the active pharmaceutical ingredient(s) from the composition for potential abuse or dose dumping and the composition provides controlled release delivery of the active pharmaceutical ingredient upon ingestion of the composition by a subject.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUG_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{overall}$" as used herein refers to the combined area under the blood (plasma, serum, or whole blood) concentration versus time curve, and is expressed in units of h·mg/L (or h·ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

As used herein, all percentages (%) refer to weight (mass) percent unless noted otherwise.

The term "about" as used herein refers to any values, including both integers and fractional components that are within a variation of up to ±10% of the value modified by the term "about."

As used herein, "a" or "an" means one or more unless otherwise specified. Terms such as "include," "including," "contain," "containing," "has," or "having," and the like, mean "comprising."

The term "or" can be conjunctive or disjunctive.

Described herein are pharmaceutical compositions comprising abuse deterrent controlled release matrices comprising active pharmaceutical ingredients. The capsule shell and matrix is structured to prevent extraction and over ingestion of the active pharmaceutical ingredients.

In one embodiment, the pharmaceutical composition described herein comprises a soft capsule comprising an abuse deterrent controlled release matrix comprising an active pharmaceutical ingredient. In one embodiment, the active pharmaceutical ingredient is an analgesic. In another embodiment, the active pharmaceutical ingredient is an opioid analgesic.

In another embodiment, the soft capsule comprising a matrix can provide controlled release properties. Such controlled release matrix fills are described in International Patent Application Publication No. WO 2005/009409 and WO 2006/096580, U.S. Patent Application Publication Nos. US 2006/0115527 and US 2007/0053868, and U.S. Pat. Nos. 8,293,270 and 8,333,989, each of which are incorporated by reference herein for such teachings. In one aspect, the soft capsule and matrix can be configured to provide controlled release, extended release, sustained release, delayed release, or combinations thereof.

In other embodiments, the pharmaceutical composition described herein comprises abuse deterrent properties. These abuse deterrent properties reduce the likelihood that the active pharmaceutical ingredient can be extracted from the composition through mechanisms, including but not limited to crushing, grating, grinding, or cutting of the capsule to expose the matrix thereby facilitating solvation or extraction of the active pharmaceutical ingredient. Exemplary and non-limiting abuse deterrent matrices useful in the pharmaceutical composition described herein may be those found in PCT International Application No. PCT/US2015/024464 and in U.S. patent application Ser. No. 14/679,233, each of which is incorporated by reference herein in their entirety. In addition, the abuse deterrent properties reduce the likelihood that the active pharmaceutical ingredient can be extracted from the composition by dissolving or extracting in ethanol solutions of about 1% to about 50%, dissolving in solutions having pH values from about 1 to about 12, or dissolving in household chemical compositions, including water, coffee, vinegar, cola, milk, ethanol, isopropanol, acetone, ethyl acetate, or other common solvents. In addition, the abuse deterrent properties further reduce the likelihood that the active pharmaceutical ingredient can be extracted by boiling in water or ethanol solutions.

In other embodiments described herein, the composition comprises a lipid or lipophilic vehicle that provides a suspension or a solution of the active pharmaceutical ingredient. In one aspect, a soft capsule comprising an active pharmaceutical ingredient provides controlled release of the active pharmaceutical ingredient.

In other embodiments described herein, the pharmaceutical composition provides matrix fills for the active pharmaceutical ingredient, or derivatives thereof, based on lipids or lipophilic materials. The matrices described herein have a hydrophobic (lipophilic) surface in contact with a hydrophilic soft capsule shell to minimize any potential shell-fill interactions, such as when the soft capsules are filled with hydrophilic materials. In one embodiment described herein are methods for manufacturing matrix fills comprising an abuse deterrent controlled release composition comprising an active pharmaceutical ingredient in a soft capsule in the form of a suspension, where part or all of the active pharmaceutical ingredient is suspended within the matrix. In one embodiment described herein is a soft capsule having a shell and an abuse deterrent controlled release matrix fill, wherein the matrix includes an active pharmaceutical ingredient suspended as solid particles within the lipophilic vehicle.

In one embodiment described herein is a soft or hard capsule having one or more active pharmaceutical ingredients in a resinate complex with one or more ion exchange resins described herein. In one aspect described herein, the one or more active pharmaceutical ingredients may be blended with one or more ion exchange resins described herein.

In one embodiment described herein, an exemplary abuse deterrent controlled release matrix has the composition of Table 1 and Table 2, including all possible iterations of the specified ranges that provide 100% for the total weight percentage, including or excluding the optional colorings, flavorings, or pharmaceutically acceptable excipients.

TABLE 1

Exemplary Abuse Deterrent Controlled Release Composition

| Component | Exemplary Components | Composition Range (%) |
|---|---|---|
| Lipid or lipophilic vehicle(s) | Liquid lipid vehicle (LLV) and/ or Semisolid lipid vehicle (SLV): soybean oil, bee's wax | 31-92 (LLV: 25-60/ SLV: 6-32) |
| Non-ionic surfactant(s) | Pluronic® F127, poloxamer, Tween® 80, Triton™ X | 1-15 |
| Hygroscopic polymer(s) | Polyvinylpyrrolidone (copovidone), ethyl cellulose, hydroxyproply methylcellulose, polyethylene oxide | 1-10 |
| Hydrophilic ionic polymer(s) | Carbopol, Eudragit®, Ethylenediamine | 2-20 |
| Suspension agent(s) | Fumed silica, Aerosil® | 0.5-5 |
| pH buffering agent(s) | Triethanolamine, N-methyl-D-glucamine, Tromethamine | 1-8 |
| Active pharmaceutical ingredient with Resin | Oxycodone, Tapentadol, Amytal, Dextromethorphan | 5-50 |
| Exchange Resin | Amberlite™ IRP 69, Amberlite™ IRP 88, | |

TABLE 2

Exemplary Abuse Deterrent Controlled Release Composition

| Component | Exemplary Components | Composition Range (%) |
|---|---|---|
| Hydrophilic vehicle | Polyethylene glycol 400-1000 | 40-80 |
| Hygroscopic polymer | Polyvinylpyrrolidone (copovidone), polyethylene oxide | 0.5-10 |
| Hydrophilic polymer(s) | Polyvinylpyrrolidone (copovidone), ethyl cellulose, hydroxypropyl methylcellulose (Methocel™ K100M), polyethylene oxide | 1-10 |
| Active pharmaceutical ingredient(s) | Oxycodone, Tapentadol, Amytal | 5-50 |
| Exchange Resin | Amberlite™ IRP 69, Amberlite™ IRP 88, | |

In another embodiment, the lipid or lipophilic vehicle can be a liquid lipophilic vehicle, a semisolid lipophilic vehicle, or combinations thereof. Suitable lipid or lipophilic vehicles include mineral oil; light mineral oil; natural oils (e.g., vegetable, corn, canola, sunflower, soybean, olive, coconut, cocoa, peanut, almond, cottonseed, persic, sesame, squalane, castor, cod liver, etc) hydrogenated vegetable oil; partially hydrogenated oils; bee's wax (beeswax); polyethoxylated bee's wax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, stearyl alcohol, and others known in the art.

In one embodiment, the lipid or lipophilic vehicle comprises both a liquid lipophilic vehicle and a semisolid lipophilic vehicle. In one embodiment, the liquid lipid or lipophilic vehicle can be olive oil, soybean oil, sunflower oil, canola oil, palmitoleic acid, oleic acid, myristoleic acid, linoleic acid, arachidonic acid, paraffin oil, or mineral oil. In another embodiment, the semi-solid lipophilic vehicle can be a polyethylene glycol glyceride ester, paraffin wax, carnauba wax, or bee's wax. In another embodiment, the semi-solid lipophilic vehicle can be Gelucire® 33/01, Gelucire® 37/02, Gelucire® 39/01, Gelucire® 43/01, Gelucire® 44/14, Gelucire® 50/02, Gelucire® 50/13, Gelucire® 53/10, or Gelucire® 62/02. In another embodiment, the Gelucire® semisolid lipid vehicle has a HLB value of about 1 and a melting point of about 43. In one aspect, the liquid lipid or lipophilic vehicle is soybean oil. In another aspect, the semisolid lipid or lipophilic vehicle comprises a wax. In another aspect, the semisolid lipid or lipophilic vehicle comprises bee's wax. In another aspect, the semisolid lipid or lipophilic vehicle comprises carnauba wax. In another aspect, the semisolid lipid or lipophilic vehicle comprises a mixture of bee's wax and carnauba wax.

In one embodiment, the composition comprises a surfactant. The surfactant can have a hydrophilic/lipophilic balance (HLB) value between about 1 and about 25 and a melting point between about 25° C. and about 70° C. The HLB characteristic of surfactants can be determined in accordance with "Physical Pharmacy: Physical Chemical Principles in the Pharmaceutical Sciences," Fourth Edition, pp. 371-373, A. Martin, Ed., Lippincott Williams & Wilkins, Philadelphia (1993). Suitable surfactants include: glyceryl monocaprylate (e.g., Capmul® MCM), Pluronic® 10R5, Pluronic® 17R2, Pluronic® 17R4, Pluronic® 25R2, Pluronic® 25R4, Pluronic® 31R1, Pluronic® F. 108, Pluronic® F. 108 NF, Pluronic® F. 108, Pluronic® F. 108NF, Poloxamer 338, Pluronic® F. 127, Pluronic® F. 127 NF, Pluronic® F. 127 NF 500 BHT Prill, Pluronic® F. 127 NF Prill, Poloxamer 407, Pluronic® F. 38, Pluronic® F. 38 Pastille, Pluronic® F. 68, Pluronic® F. 68 LF Pastille, Pluronic® F. 68 NF, Pluronic® F. 68 NF Prill, Poloxamer 188, Pluronic® F. 68 Pastille, Pluronic® F. 77, Pluronic® F. 77 Micropastille, Pluronic® F. 87, Pluronic® F. 87 NF, Pluronic® F. 87 NF Prill, Poloxamer 237, Pluronic® F. 88, Pluronic® F. 88 Pastille, Pluronic® F. 98, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® N 3, Pluronic® P 103, Pluronic® P 104, Pluronic® P 105, Pluronic® P 123 Surfactant, Pluronic® P 65, Pluronic® P 84, Pluronic® P 85, Adogen 464, Alkanol 6112, Brij® 52, Brij® 93, Brij® S2, Brij® S, Brij® 58, Brij® C10, Brij® L4, Brij® O10, Brij® O10, BRIJ® O20, Brij® S10, Brij® S20, ethylenediamine tetrakis(ethoxylate-block-propoxylate) tetrol, ethylenediamine tetrakis(ethoxylate-block-propoxylate) tetrol, ethylenediamine tetrakis(propoxylate-block-ethoxylate) tetrol, IGEPAL® CA-210, IGEPAL® CA-520, IGEPAL® CA-720, IGEPAL® CO-520, IGEPAL® CO-630, IGEPAL® CO-720, IGEPAL® CO-890, IGEPAL® DM-970, MERPOL® DA, MERPOL® HCS, MERPOL® OJ, MERPOL® SE, MERPOL® SH, MERPOL® A, Poly(ethylene glycol) sorbitan tetraoleate, poly(ethylene glycol) sorbitol hexaoleate, poly(ethylene glycol) (12), poly(ethylene glycol) (18), polyethylene-block-poly(ethylene glycol), sorbitan monopalmitate, 2,4,7,9-tetramethyl-5-decyne-4,7-diol ethoxylate, Nonidet™ P-40, Triton™ N-101, Triton™ X-100, Triton™ X-114, Triton™ X-405, TWEEN® 20, TWEEN® 40, TWEEN® 60, TWEEN® 85, Zonyl® FS-300, or Zonyl® FSN. In one embodiment, the surfactant comprises Pluronic® F127, Tween® 80, Span® 80, IGEPAL®, Triton™ X-100, or Capmul® MCM.

In another embodiment, the abuse deterrent composition comprises one or more hydrophilic polymers. Suitable, non-limiting hydrophilic polymers comprise methylcellulose, hydroxypropylmethyl cellulose, hydroxypropyl cellulose, hydroxypropyl methylcellulose, hydroxyethyl cellulose, hydroxymethyl cellulose, polymethylmethacrylate, polyhydroxyethylmethacrylate, polyvinyl pyrrolidone, polyvinylpyrrolidone, copovidone, polyethylene oxide such as POLYOX™ 100,000-8,000,000 MW, polyvinyl alcohol, a copolymer of polyvinylpyrrolidone and polyvinyl acetate, or combinations thereof. In one aspect, the hydrophilic polymers comprise one or more of Methocel™ K100 Premium LV CR, K4M Premium CR, K15M Premium CR, K100 Premium CR, E4M Premium CR, E10M Premium CR, or E4M Premium (Dow Chemical Co.); POLYOX™, CELLOSIZE™, or WALOCEL™ CRT. Without being bound by any theory, it is thought that water coming into contact with the hydrophilic polymer, such as methylcellulose or hydroxypropylmethylcellulose, causes it to expand or swell and further impede the release of active pharmaceutical ingredients from the composition. In one aspect, the hydrophilic polymer comprises methylcellulose. In one aspect, the hydrophilic polymer comprises hydroxypropylmethylcellulose. In another aspect, the hydrophilic polymer comprises a viscosity of about 10 cP to about 100,000 cP. In another aspect, hydrophilic polymer comprises a viscosity of about 50 cP, about 100 cP, about 200 cP, about 300 cP, about 400 cP, about 500 cP, about 750 cP, about 1,000 cP, about 1,500 cP, about 2,000 cP, about 2,500 cP, about 3,000 cP, about 3,500 cP, about 4,000 cP, about 4,500 cP, about 5,000 cP, about 6,000 cP, about 7,000 cP, about 8,000 cP, about 9,000 cP, or about 10,000 cP, about 15,000 cP, about 20,000 cP, about 30,000 cP, about 40,000 cP, about 50,000 cP, about 60,000 cP, about 70,000 cP, about 80,000 cP, about 90,000 cP, about 100,000 cP, greater than 100,000 cP, or even greater. In one aspect, methylcellulose has a viscosity of about 4,000 cP (e.g., Methocel™ A4M). In another aspect, hydroxypropylmethylcellulose has a viscosity of about 100,000 cP (e.g., Methocel™ K100M).

In one embodiment, the composition comprises a hydrophilic ionic polymer. In one embodiment, the hydrophilic polymers comprise polyhydroxylalkylenediamine, dimethylaminoethyl methacrylate copolymer, Poly(butyl methacrylate-co-(2-dimethylaminoethyl) methacrylate-co-(2-dimethylaminoethyl) 1:2:1 (Eudragit® EPO); sodium carboxy methylcellulose, carboxymethyl cellulose ethylenediamine, sodium alginate, alginic acid, pectin, carbomers, Carbopol® copolymers (polyacrylic acid polymers), such as Carbopol® 934, Carbopol® 940, Carbopol® 941 or Carbopol® 974P; a Pemulen® polymer; polycarbophil poly galacturonic acid, polyglucoronic acid, chondroitic sulfate, carrageenan, and acrylic methacrylate copolymers. In one aspect, the hydrophilic polymer swells in aqueous media. In another aspect, the hydrophilic polymers swell at a pH of about 4 to about 6. In another embodiment, one or more hydrophilic ionic polymers form ionic interactions. In another embodiment, the composition comprises anionic polymers, cationic polymers, or mixtures thereof. In another embodiment, a hydrophilic cationic polymer and a hydrophilic anionic polymer are combined to form an ionic polymer complex or network. In one aspect, the hydrophilic ionic polymer is Carbopol® 971A. In another aspect, the hydrophilic ionic polymer is Eudragit® EPO.

In another embodiment, the composition comprises a hygroscopic polymer. In one embodiment, the hygroscopic polymers include polyvinylpyrrolidone, copovidone, hydroxypropylmethylcellulose, hydroxypropylcellulose, ethyl cellulose, methylcellulose, and polyethylene oxide. Suitable hygroscopic polymers include polyvinyl alcohol, a copolymer of polyvinylpyrrolidone and polyvinyl acetate, hydroxypropyl cellulose, hydroxypropyl methylcellulose, hydroxyethyl cellulose, hydroxymethyl cellulose, gelatin, polyethylene oxide, such as POLYOX™ 100,000-600,000 MW, acacia, dextrin, starch, polyhydroxyethylmethacrylate, a water-soluble non-ionic polymethacrylate or copolymer thereof, a modified cellulose, a modified polysaccharide, a non-ionic gum, or a non-ionic polysaccharide. In one aspect, the hygroscopic polymer is polyvinylpyrrolidone. In one aspect, the hygroscopic polymer comprises Kollidon® 90 F. In one aspect, the hygroscopic polymer comprises a cellulose polymer. In one aspect, the hygroscopic polymer comprises hydroxypropylmethylcellulose (e.g., HPMC 4M). In another aspect, the hygroscopic polymer is a polyethylene oxide polymer (e.g., POLYOX™ 100,000).

In another embodiment, the abuse deterrent composition comprises one or more hydrophilic vehicles. Suitable, non-limiting hydrophilic vehicles comprise hydro-alcohols including propylene glycol, or polyethylene glycols of a molecular weight ranging from about 200 to about 8,000 (MN, number average molecular weight) or a mixture or combination thereof. In one aspect, the hydrophilic vehicle comprises polyethylene glycol. In another aspect, the hydrophilic vehicle comprises polyethylene glycol 600. In another aspect, the hydrophilic vehicle comprises polyethylene glycol 1000. In another aspect, the hydrophilic vehicle comprises polyethylene glycol 600 and polyethylene glycol 1000.

In one embodiment described herein, the composition comprises: (a) about 35% to about 70% by mass of one or more flowability enhancers; (b) about 20% to about 50% by mass of one or more release modifiers; and (c) about 1% to about 30% by mass of one or more active pharmaceutical ingredients. In one aspect, the composition further comprises: (d) about 0.05% to about 0.5% of one or more antioxidants. In one aspect, the composition comprises: (a) glyceryl monolinoleate; (b) polyethylene oxide; and (c) an opiod such as oxycodone, hydrocodone, or salts thereof. In another aspect, the composition further comprises: (d) butylated hydroxytoluene (BHT); and (e) butylated hydroxyanisole (BHA). In another aspect, the composition comprises: (a) about 50% to about 70% by mass of glyceryl monolinoleate; (b) about 25% to about 40% by mass of polyethylene oxide; and (c) about 1% to about 20% by mass of an opiod such as oxycodone, hydrocodone, or salts thereof. In another aspect, the composition further comprises: (d) about 0.05% to about 0.4% by mass of BHA; and (e) about 0.05% to about 0.2% by mass of BHT. In another aspect, the composition comprises: (a) about 55% to about 65% by mass of glyceryl monolinoleate; (b) about 30% to about 35% by mass of polyethylene oxide; and (c) about 1% to about 15% by mass of an opiod such as oxycodone, hydrocodone, or salts thereof. In another aspect, the composition further comprises: (d) about 0.1% to about 0.4% by mass of BHA; and (e) about 0.05% to about 0.1% by mass of BHT. In another aspect, the composition comprises: (a) about 50% to about 70% by mass of glyceryl monolinoleate; (b) about 25% to about 40% by mass of polyethylene oxide; (c) about 0.1% to about 0.4% by mass of BHA; (d) about 0.05% to about 0.1% by mass of BHT; and (e) about 1% to about 20% of by mass of an opiod such as oxycodone, hydrocodone, or salts thereof A common method for extracting abuse prone drugs is by boiling the composition. Thus, in some embodiments, the abuse deterrent matrices described herein reduce the percentage of released active pharmaceutical ingredient released during boiling conditions.

In another embodiment, the abuse-deterrent composition comprises one or more antioxidants. Suitable antioxidants comprise tocopherols (e.g., alpha-tocopherol, beta-tocopherol, gamma-tocopherol, or delta-tocopherol), butylated hydroxytoluene (BHT), butylated hydroxyanisole (BHA), citric acid, ascorbic acid, phenolic diterpenes (e.g., carnosic acid, carnosol, rosmanol, epirosmanol, isorosmanol, or methyl carnosate), rosmarinic acid, eugenol, eugenyl acetate, clove bud extract, methanolic extract, tea catechins (e.g., epigallocatechin gallate, epicatechin gallate, epigallocatechin, or epicatechin), or combinations thereof.

In another embodiment, the abuse deterrent composition can include a hydrophilic internal phase and a lipid or lipophilic external phase (water in oil) or a lipid or lipophilic internal phase and a hydrophilic external phase (oil in water). The internal phase can also be structured. A "structured" phase, as used herein, means a solid, semisolid, or a gel whose shape is relatively stable and does not usually aggregate to form a large globule. One or more structured phases provide controlled drug release and stabilize the physical state of the matrix. Without being bound to any theory, it is believed that a structured matrix impedes solvation and/or diffusion of the active pharmaceutical ingredient out of the matrix after the capsule shell dissolves.

In another embodiment, the active pharmaceutical ingredient can be dispersed in the internal phase as a suspension form. A suspension as used herein means the API does not dissolve in one of the phases and remains as a solid. In one embodiment, the active pharmaceutical ingredient is dispersed or suspended in the internal phase as a solid form.

In one embodiment, the pharmaceutical composition may comprise an active pharmaceutical ingredient in complex with an ion-exchange resin. Suitable ion exchange resins described herein are water-insoluble and comprise a pharmacologically inert organic and/or inorganic matrix containing covalently bound functional groups that are ionic or capable of being ionized under appropriate pH conditions. The organic composition may be synthetic (e.g., polymers or copolymers of acrylic acid, methacrylic acid, sulfonated styrene, sulfonated divinylbenzene), or partially synthetic (e.g., modified cellulose and dextrans). The inorganic composition preferably comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In one aspect, the ion exchange resin is a sulfonated styrene and divinylbenzene copolymer such as polystyrene sulfonate or a salt thereof (e.g., Amberlite IRP-69).

Exemplary ion-exchangers suitable for use in ion-exchange chromatography and for such applications as deionization of water are suitable for use in the compositions described herein. Suitable ion exchange resins are also sold under the trade names Amberlite™ and Dowex™ Both regularly and irregularly shaped particles may be used as resins. Regularly shaped particles are those particles that substantially conform to geometric shapes, such as spherical, elliptical, cylindrical and the like. Irregularly shaped ion-exchange resins of this type are exemplified by Amberlite™ IRP-69, which consists of irregularly-shaped particles with a size range of 47 microns to 149 microns. Such ion-exchangers are described by H. F. Walton in "Principles of Ion Exchange" (pp. 312-343) and "Techniques and Applications of Ion-Exchange Chromatography" (pp. 344-361) in Chromatography. (E. Heftmann, editor), Van Nostrand Reinhold Company, New York (1975) and in U.S. Patent Application Publication No 2014/0127300, each of which is incorporated herein by reference for its teachings of ion exchange resins thereof. Further non-limiting ion-exchangers are shown in Table 3.

TABLE 3

Exemplary Cation and Anion Exchange Resins

| Polymer | Exchanger type |
| --- | --- |
| Amberlite IRP 69 | Strong Cation |
| Amberlite 200/200C | Strong Cation |
| DOWEX ™ 50WX8H | Strong Cation |
| DOWEX ™ 88 | Strong Cation |
| Purolite ® C100HMR | Strong Cation |
| Purolite ® C100NaMR | Strong Cation |
| Purolite ® C100CaMR | Strong Cation |
| Lewatit K ® 1481 | Strong Cation |
| Lewasorb ® SW 12 | Strong Cation |
| Amberlite ™ IRP 64 | Weak Cation |
| Amberlite ™ IRP 88 | Weak Cation |
| Purolite ® C 115 K MR | Weak Cation |
| Purolite ® C 115 H MR | Weak Cation |
| Purolite ® C 108DR | Weak Cation |
| Lewatit ® CNP 105 | Weak Cation |
| PolyAMPs | Other |
| Polyvinylsulfonic acid (+derivatives) | Other |
| Polyvinylphosphonic acid (+derivatives) | Other |
| Poly acrylic acid (+derivatives) | Other |

Binding of the active pharmaceutical ingredients to the resins described herein may be accomplished using methods known in the art. For example, the general reactions may be used for a basic drug these are: (a) resin (e.g., Natform) and an ionic salt form of the drug being bound; (b) resin (e.g., $Na^+$-form) plus free base form of drug.

Analogous binding reactions can be carried out for binding an acidic drug an anion exchange resin. These are: (a)

resin (e.g., Cl⁻ form) plus the salt form of acidic drug to be bound; (b) resin (e.g., Cl⁻ form) plus the free acid form of the drug to be bound; (c) resin (e.g., OH⁻-form) plus salt form of drug to be bound; and (d) resin (e.g., OH⁻-form) plus free acid form of drug to be bound.

This binding may be performed, for example, as a batch or column process, as is known in the art. The drug-resin complexes described herein may be prepared by a batch process that is based on reaction the exemplary reactions described herein. The drug to be loaded on the ion exchange resin may be dissolved in an aqueous medium or in a solvent miscible with water to make a solution. The drug-containing solution is then placed in a slurry of the resin or a column loaded with resin. The drug-resin resinate complex thus formed is collected by filtration and washed with deionized or purified water to ensure removal of any unbound drug.

In one embodiment described herein, the amount of drug loaded onto the resin to form a resinate ranges from about 1% to about 80%, including each integer within the specified range. In one aspect, the amount of drug loaded onto the resin ranges from about 10% to about 60%, including each integer within the specified range. In another aspect, the amount of drug loaded onto the resin ranges from about 30% to about 50%, including each integer within the specified range. In another aspect, the amount of drug loaded onto the resin comprises about 50%. In another aspect, the amount of drug loaded onto the resin comprises about 33%. In another aspect, the amount of drug loaded onto the resin comprises about 25%. In another aspect, the amount of drug loaded onto the resin comprises about 20%. In another aspect, the amount of drug loaded onto the resin comprises about 17%. In another aspect, the amount of drug loaded onto the resin comprises about 14%. In another aspect, the amount of drug loaded onto the resin comprises about 12.5%. In another aspect, the amount of drug loaded onto the resin comprises about 10%.

Another embodiment described herein is oral immediate release pharmaceutical composition comprising one or more active pharmaceutical ingredients, one or more sequestering agents, and optionally, one or more pharmaceutically acceptable excipients, wherein the active pharmaceutical ingredients is not pre-bound to the sequestering agent in the dosage form. In one aspect, the quantity of active pharmaceutical ingredients (API) bound to the sequestering agent in the composition prior to ingestion and solvation is about 0.001% to about 1% including each integer within the specified range. In one aspect the amount of API pre-bound to the sequestering agent prior to ingestion is less than about: 0.001%, about 0.005%, about 0.01%, about 0.05%, about 0.1%, about 0.5%, or about 1%. In one aspect the amount of API bound to the sequestering agent in the composition prior to ingestion is less than about 1%. In one aspect, the pharmaceutical composition is a dry powder admixture of one or more sequestering agents and one or more APIs and optionally one or more pharmaceutically acceptable excipients. In another aspect, the composition is a tablet, compressed tablet, or capsule. In these compositions effectively none of the API is boud to the sequestering agent. Dry powers of the API and sequestering agent and any excipients are merely combined, homogenized, and the dosage form produced. The particles of the sequestering agent are incapable of effectively interacting with the molecules of API in the solid state of the composition (as compared to a solution-state binding interaction). Upon ingestion of the composition by a subject, both the sequestering agent and API rapidly dissolve in the gastric fluid and ingested liquid(s) in the stomach. The sequestering agent is then capable of adsorbing a quantity of the API in situ (in the stomach) and impedes or delays absorption of the bound API into systemic circulation.

In one embodiment, the quantity of the API adsorbed by the sequestering agent after ingestion of a single dose of the composition is about 0.5% to about 15%, including each integer within the specified range. In one aspect, the quantity of the API adsorbed by the sequestering agent after ingestion of a single dose of the composition is about 0.5%, about 1%, about 2.5%, about 5%, about 7.5%, about 10%, about 12%, about 15%, about 20%, about 25%, or about 30%. In aspect, the quantity of the API adsorbed by the sequestering agent after ingestion of a single dose of the composition is about 0.5% to about 15%.

In another embodiment, when a plurality of doses of the composition are simultaneously ingested or successively ingested over about a 4-hour period, the greater quantities of sequestering agent adsorb greater quantities of the API in situ and impede or delay absorption of the bound API into systemic circulation. Typical gastric emptying for a human is about 4 hours. As additional doses of the composition are ingested and solvated in the stomach, greater quantities of sequestering agent are available to adsorb the API. The principles of mass action and equilibrium binding dictate the adsorption and subsequent release of the API from the sequestering agent. The quantity of the API adsorbed by the sequestering agent when one or more doses of the composition is about 0.5% to about 80%, including each integer within the specified range. In one aspect the quantity of the API adsorbed by the sequestering agent is about 1%, about 2%, about 5%, about 10%, about 15%, about 20%, about 25%, about 30%, about 35%, about 40%, about 45%, about 50%, about 55%, about 60%, about 65%, about 70%, about 75%, or about 80%. In one aspect the quantity of the API adsorbed by the sequestering agent is about 15% to about 70%.

In one embodiment, the sequestering agent is capable of adsorbing API when a single dose of the composition is administered and the extent bound depends on the molar ratio of the sequestering agent's binding sites to API. In another aspect, when a plurality of doses of the composition is ingested simultaneously, nearly simultaneously, or in succession over a period of time prior to the onset of gastric emptying (ca. 4 hours), the greater quantities of sequestering agent present in the stomach are capable of binding greater quantities of the API and consequently delay or retard absorption of the API into the systemic circulation. A plurality of doses can comprise 2 or more dosage forms. In one aspect a plurality of doses comprises 2, 3, 4, 5, 6, 7, 8, 9, 10, 11, 12, 13, 14, 15, 16, 17, 18, 19, 20, or greater than 20 doses. Without being bound by any theory, the composition described herein reduces the $C_{max}$ observed by delaying, retarding, or impeding the absorption of the API into systemic circulation and can also delay $T_{max}$. The AUC observed is proportional to the total dose of API, but the absorption time is extended because the API is more slowly absorbed into systemic circulation as the equilibrium shifts from sequestering agent-bound API to free API that can be absorbed. Clearance time is also extended because the absorption rate constant and elimination rate constant are both reduced. The composition mitigates accidental or intentional overingestion by precluding a bolus concentration of API available for absorption that can lead to toxic $C_{max}$ levels and consequent physiological effects such as depressed respiration, coma, cardiac arrest, or death.

Another embodiment described herein is a composition or a method for reducing the $C_{max}$ of an API. In one aspect the composition comprises an oral immediate release pharmaceutical composition comprising one or more active pharmaceutical ingredients, one or more sequestering agents, and optionally, one or more pharmaceutically acceptable excipients, wherein the active pharmaceutical ingredient is not bound to the sequestering agent in the dosage form. Another aspect is a method for maintaining a specific $C_{max}$ of an API within a therapeutic concentration window or below a maximum concentration comprising administering to a subject one or more oral immediate release pharmaceutical compositions comprising one or more active pharmaceutical ingredients (API), optionally, one or more sequestering agents, and optionally, one or more pharmaceutically acceptable excipients, where less than about 1% of the API is bound to the sequestering agent, and following ingestion of at least one dose by a subject, the sequestering agent adsorbs a quantity of the API and impedes its release into the subject's systemic circulation. In one aspect, the $C_{max}$ of an API in a composition comprising a sequestering agent is about 10% to about 50% less than an equivalent dose of the API in a composition lacking a sequestering agent including each integer within the specified percentage range. In one aspect, the API's $C_{max}$ is about 30% less; about 25% less, or about 50% less when a composition comprising a sequestering agent is administered than an equivalent dose of the API in a composition lacking a sequestering agent.

Another embodiment described herein is a composition or a method for maintaining a specific concentration of an API within a therapeutic concentration window. In one aspect the composition comprises an oral immediate release pharmaceutical composition comprising one or more active pharmaceutical ingredients, one or more sequestering agents, and optionally, one or more pharmaceutically acceptable excipients, wherein the active pharmaceutical ingredient is not bound to the sequestering agent in the dosage form. Another aspect is a method for maintaining a specific concentration of an API within a therapeutic concentration window comprising administering to a subject one or more oral immediate release pharmaceutical compositions comprising one or more active pharmaceutical ingredients (API), optionally, one or more sequestering agents, and optionally, one or more pharmaceutically acceptable excipients, where less than about 1% of the API is bound to the sequestering agent, and following ingestion of at least one dose by a subject, the sequestering agent adsorbs a quantity of the API and impedes its release into the subject's systemic circulation. In another aspect, the method comprises acquiring a bodily fluid from the subject; measuring the concentration of the API in the subject's circulation; and according to the measured API concentration and a desired optimal API therapeutic concentration, either administering one or more doses of the composition comprising the API and a sequestering agent; administering an equivalent dose of the API comprising a composition lacking a sequestering agent; or administering either one or more doses of the composition comprising the API and a sequestering agent or administering an equivalent dose of the API comprising a composition lacking a sequestering agent after a period of about 30 min to about 12 hours, including all integers within the specified time range. In one aspect, doses of the API with a sequestering agent can be titrated against equivalent does of the same API without a sequestering agent to achieve the optimum API therapeutic plasma concentration window.

In another embodiment described herein, the drug and a sequestering agent, such as a resin, are combined with each other in the dry state (a dry admixture) so that the drug is not bound to the resin. Upon ingestion, the resin and drug are solvated and the solvated resin is capable of binding a portion of the solvated drug. In one embodiment the quantity (mass) of resin is a multiple of the quantity (mass) of drug comprising a range from 1:1 to 20:1, including all ratios within the specified range. In some embodiments the quantity (mass) of resin is a multiple of the quantity (mass) of drug, such as: 2:1, 3:1, 4:1, 5:1, 6:1, 7:1, 8:1, 9:1, or 10:1. In another embodiment, the quantity (mass) of resin is equal to the quantity (mass) of drug (1:1). An equal quantity of resin and drug by mass does not necessarily saturate the resin because the polymeric resin has many binding sites per polymer. The moles of binding sites or milliequivalents per gram of sequestering agent can be determined by the capacity of the resin.

In another embodiment described herein, the abuse deterrent compositions described herein can prevent extraction of an active pharmaceutical ingredient through the additional means of crushing, grating, grinding, or cutting dosage forms comprising the pharmaceutical compositions described herein. In another embodiment described herein, the abuse deterrent composition also prevents the overingestion of one or more active pharmaceutical ingredients described herein.

In one embodiment, the composition comprises any one of the compositions of Tables 13-17 or 19.

In another embodiment, the one or more active pharmaceutical ingredient comprises from about 1% to about 50% of the total composition mass, including all integers within the specified range. In another embodiment, the one or more active pharmaceutical ingredient comprises from about 1% to about 25% of the total composition mass, including all integers within the specified range. In one aspect, the active pharmaceutical ingredient comprises about 5% of the total composition mass. In one aspect, the active pharmaceutical ingredient comprises about 7% of the total composition mass. In one aspect, the active pharmaceutical ingredient comprises about 10.5% of the total composition mass. In one aspect, the active pharmaceutical ingredient comprises about 20% of the total composition mass. In one aspect, the active pharmaceutical ingredient comprises about 25% of the total composition mass.

In another embodiment, the ratio of active pharmaceutical ingredient to the total composition ranges from about 1:100 to about 1:2, including all iterations of ratios within the specified range. In another embodiment, the ratio of active pharmaceutical ingredient to the total composition ranges from about 1:15 to about 1:2, including all iterations of ratios within the specified range. In one aspect, the ratio of active pharmaceutical ingredient to the total composition is about 1:100. In another aspect, the ratio of active pharmaceutical ingredient to the total composition is about 1:10. In another aspect, the ratio of active pharmaceutical ingredient to the total composition is about 1:7.5. In another aspect, the ratio of active pharmaceutical ingredient to the total composition is about 1:5. In another aspect, the ratio of active pharmaceutical ingredient to the total composition is about 1:3. In another aspect, the ratio of active pharmaceutical ingredient to the total composition is about 1:2.

In another embodiment, the ratio of active pharmaceutical ingredient to the resin or resinate ranges from about 1:50 to about 10:1, including all iterations of ratios within the specified range. In another embodiment, the ratio of active pharmaceutical ingredient to the resin or resinate ranges from about 1:5 to about 1:1, including all iterations of ratios within the specified range. In one aspect, the ratio of active pharmaceutical ingredient to the resin or resinate is about 1:50. In another aspect, the ratio of active pharmaceutical ingredient to the resin or resinate is about 1:10. In another aspect, the ratio of active pharmaceutical ingredient to the resin or resinate is about 1:5. In another aspect, the ratio of active pharmaceutical ingredient to the resin or resinate is about 1:2. In another aspect, the ratio of active pharmaceutical ingredient to the resin or resinate is about 1:1. In another aspect, the ratio of active pharmaceutical ingredient to the resin or resinate is about 2:1. In another aspect, the ratio of active pharmaceutical ingredient to the resin or resinate is about 3:1. In another aspect, the ratio of active pharmaceutical ingredient to the resin or resinate is about 4:1.

In one embodiment, the composition contains an active pharmaceutical ingredient in a suspended, form, soluble form, insoluble form, or combinations thereof. In another embodiment, the composition contains an active pharmaceutical ingredient useful for the treatment of pain. In one embodiment, the active pharmaceutical ingredient includes tapentadol, oxycodone, morphine, morphine analogues, or morphine antagonists, codeine, morphine, methadone, fentanyl and analogs, opioid pain relievers: oxycodone hydrochloride, hydrocodone bitartrate hydromorphone, oxymorphone, meperidine, propoxyphene, flunitrazepam, barbiturates, amytal, nembutal, seconal, phenobarbital; benzodiazepines, zolpidem, zaleplon, eszopiclone, amphetamines, or methylphenidate.

In one embodiment, the composition comprises one or more active pharmaceutical ingredients (API). In one aspect, the active pharmaceutical ingredient is useful in treating pain. In one aspect, the active pharmaceutical ingredient is tapentadol, oxycodone, hydrocodone, or codeine. In one aspect, the active pharmaceutical ingredient is oxycodone or hydrocodone.

Examples of specific active drug substances suitable for use in the pharmaceutical compositions provided herein include: anti-inflammatory and antirheumatic active drug substances, such as, for example: butylpyrazolidine, phenylbutazone, mofebutazone, oxyphenbutazone, clofezone, kebuzone, acetic acid derivatives and related substances, indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, oxicam, piroxicam, tenoxicam, droxicam, lornoxicam, meloxicam, methotrexate, propionic acid derivatives, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, fenamates, mefenamic acid, tolfenamic acid, flufenamic acid, meclofenamic acid, coxibs, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, feprazone, dipyrocetyl, acetylsalicylic acid, quinolines, oxycinchophen, gold preparations, sodium aurothiomalate, sodium aurotiosulfate, auranofin, aurothioglucose, aurotioprol, penicillamine or bucillamine.

In another embodiment, suitable active pharmaceutical ingredients can comprise analgesics, such as, for example: opioids, natural opium alkaloids, morphine, opium, hydromorphone, nicomorphine, oxycodone, dihydrocodone, diamorphine, tapentadol, papaveretum, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics, such as, for example: rimazolium, glafenine, floctafenine, viminol, nefopam, flupirtine, or ziconotide.

In another embodiment, suitable active pharmaceutical ingredients can comprise anaesthetics, such as, for example: ethers, diethyl ether, vinyl ether, halogenated hydrocarbons, halothane, chloroform, methoxyflurane, enflurane, trichloroethylene, isoflurane, desflurane, sevoflurane, barbiturates, methohexital, hexobarbital, thiopental, narcobarbital, opioid anaesthetics, fentanyl, alfentanil, sufentanil, phenoperidine, anileridine, remifentanil, other general anaesthetics, such as, for example: droperidol, ketamine, propanidid, alfaxalone, etomidate, propofol, hydroxybutyric acid, nitrous oxide, esketamine, xenon, esters of aminobenzoic acid, metabutethamine, procaine, tetracaine, chloroprocaine, benzocaine, amides, bupivacaine, lidocaine, mepivacaine, prilocaine, butanilicaine, cinchocaine, etidocaine, articaine, ropivacaine, levobupivacaine, esters of benzoic acid, cocaine, other local anaesthetics, such as, for example: ethyl chloride, dyclonine, phenol, or capsaicin.

In another embodiment, suitable active pharmaceutical ingredients can comprise antimigraine active drug substances, such as, for example: ergot alkaloids, dihydroergotamine, ergotamine, methysergide, lisuride, corticosteroid derivatives, flumedroxone, selective serotonin ($5HT^1$) agonists, sumatriptan, naratriptan, zolmitriptan, rizatriptan, almotriptan, eletriptan, frovatriptan, other antimigraine preparations, pizotifen, clonidine, iprazochrome, dimetotiazine, or oxetorone.

In another embodiment, suitable active pharmaceutical ingredients can comprise antiepileptic active drug substances, such as, for example: barbiturates and derivatives, methylphenobarbital, phenobarbital, primidone, barbexaclone, metharbital, hydantoin derivatives, ethotoin, phenytoin, amino(diphenylhydantoin) valeric acid, mephenytoin, fosphenytoin, oxazolidine derivatives, paramethadione, trimethadione, ethadione, succinimide derivatives, ethosuximide, phensuximide, mesuximide, benzodiazepine derivatives, clonazepam, carboxamide derivatives, carbamazepine, oxcarbazepine, rufinamide, fatty acid derivatives, valproic acid, valpromide, aminobutyric acid, vigabatrin, progabide, tiagabine, other antiepileptics, such as, for example: sultiame, phenacemide, lamotrigine, felbamate, topiramate, gabapentin, pheneturide, levetiracetam, zonisamide, pregabalin, stiripentol, lacosamide, or beclamide.

In another embodiment, suitable active pharmaceutical ingredients can comprise anticholinergic active drug substances, such as, for example: tertiary amines, trihexyphenidyl, biperiden, metixene, procyclidine, profenamine, dexetimide, phenglutarimide, mazaticol, bornaprine, tropatepine, ethers chemically close to antihistamines, etanautine, orphenadrine (chloride), ethers of tropine or tropine derivatives, benzatropine, or etybenzatropine.

In another embodiment, suitable active pharmaceutical ingredients can comprise dopaminergic active drug substances, such as, for example: dopa and dopa derivatives, levodopa, melevodopa, etilevodopa, adamantane derivatives, amantadine, dopamine agonists, bromocriptine, pergolide, dihydroergocryptine mesylate, ropinirole, pramipexole, cabergoline, apomorphine, piribedil, rotigotine, monoamine, oxidase B inhibitors, selegiline, rasagiline, other dopaminergic agents, such as, for example: tolcapone, entacapone, or budipine.

In another embodiment, suitable active pharmaceutical ingredients can comprise antipsychotic active drug substances, such as, for example: phenothiazines with aliphatic side-chain, chlorpromazine, levomepromazine, promazine, acepromazine, triflupromazine, cyamemazine, chlorproethazine, phenothiazines with piperazine structure, dixyrazine, fluphenazine, perphenazine, prochlorperazine, thiopropazate, trifluoperazine, acetophenazine, thioproperazine, butaperazine, perazine, phenothiazines with piperidine structure, periciazine, thioridazine, mesoridazine, pipotiazine, butyrophenone derivatives, haloperidol, trifluperidol, melperone, moperone, pipamperone, bromperidol, benperidol, droperidol, fluanisone, indole derivatives, oxypertine, molindone, sertindole, ziprasidone, thioxanthene derivatives, flupentixol, clopentixol, chlorprothixene, tiotixene, zuclopenthixol, diphenylbutylpiperidine derivatives, fluspirilene, pimozide, penfluridol, diazepines, oxazepines, thiazepines, loxapine, clozapine, olanzapine, quetiapine, neuroleptics, tetrabenazine, benzamides, sulpiride, sultopride, tiapride, remoxipride, amisulpride, veralipride, levosulpiride, lithium, other antipsychotics, such as, for example prothipendyl, risperidone, clotiapine, mosapramine, zotepine, aripiprazole, or paliperidone.

In another embodiment, suitable active pharmaceutical ingredients can comprise anxiolytic active drug substances, such as, for example: benzodiazepine derivatives, diazepam, chlordiazepoxide, medazepam, oxazepam, potassium clorazepate, lorazepam, adinazolam, bromazepam, clobazam, ketazolam, prazepam, alprazolam, halazepam, pinazepam, camazepam, nordazepam, fludiazepam, ethyl loflazepate, etizolam, clotiazepam, cloxazolam, tofisopam, diphenylmethane derivatives, hydroxyzine, captodiame, carbamates, meprobamate, emylcamate, mebutamate, dibenzo-bicyclooctadiene derivatives, benzoctamine, azaspirodecanedione derivatives, buspirone, other anxiolytics, such as, for example: mephenoxalone, gedocarnil, or etifoxine.

In another embodiment, suitable active pharmaceutical ingredients can comprise hypnotic and sedative active drug substances, such as, for example: barbiturates, pentobarbital, amobarbital, butobarbital, barbital, aprobarbital, secobarbital, talbutal, vinylbital, vinbarbital, cyclobarbital, heptabarbital, reposal, methohexital, hexobarbital, thiopental, ethallobarbital, allobarbital, proxibarbal, aldehydes and derivatives, chloral hydrate, chloralodol, acetylglycinamide chloral hydrate, dichloralphenazone, paraldehyde, benzodiazepine emepronium derivatives, flurazepam, nitrazepam, flunitrazepam, estazolam, triazolam, lormetazepam, temazepam, midazolam, brotizolam, quazepam, loprazolam, doxefazepam, cinolazepam, piperidinedione derivatives, glutethimide, methyprylon, pyrithyldione, benzodiazepine related drugs, zopiclone, zolpidem, zaleplon, ramelteon, other hypnotics and sedatives, such as, for example: methaqualone, clomethiazole, bromisoval, carbromal, scopolamine, propiomazine, triclofos, ethchlorvynol, valerian, hexapropymate, bromides, apronal, valnoctamide, methylpentynol, niaprazine, melatonin, dexmedetomidine, or dipiperonylaminoethanol.

In another embodiment, suitable active pharmaceutical ingredients can comprise antidepressant active drug substances, such as, for example: non-selective monoamine reuptake inhibitors, desipramine, imipramine, imipramine oxide, clomipramine, opipramol, trimipramine, lofepramine, dibenzepin, amitriptyline, nortriptyline, protriptyline, doxepin, iprindole, melitracen, butriptyline, dosulepin, amoxapine, dimetacrine, amineptine, maprotiline, quinupramine, selective serotonin reuptake inhibitors, zimeldine, fluoxetine, citalopram, paroxetine, sertraline, alaproclate, fluvoxamine, etoperidone, escitalopram, monoamine oxidase inhibitors, isocarboxazid, nialamide, phenelzine, tranylcypromine, iproniazide, iproclozide, monoamine oxidase A inhibitors, moclobemide, toloxatone, other antidepressants, such as, for example: oxitriptan, tryptophan, mianserin, nomifensine, trazodone, nefazodone, minaprine, bifemelane, viloxazine, oxaflozane, mirtazapine, medifoxamine, tianeptine, pivagabine, venlafaxine, milnacipran, reboxetine, gepirone, duloxetine, agomelatine, desvenlafaxine, centrally acting sympathomimetics, such as, for example: amfetamine, dexamfetamine, lisdexamfetamine, metamfetamine, methylphenidate, dexmethylphenidate, pemoline, fencamfamin, modafinil, fenozolone, atomoxetine, fenetylline, xanthine derivatives, caffeine, propentofylline, other psychostimulants and nootropics, such as, for example meclofenoxate, pyritinol, piracetam, deanol, fipexide, citicoline, oxiracetam, pirisudanol, linopirdine, nizofenone, aniracetam, acetylcarnitine, idebenone, prolintane, pipradrol, pramiracetam, adrafinil, or vinpocetine.

In another embodiment, suitable active pharmaceutical ingredients can comprise anti-dementia active drug substances, such as, for example: anticholinesterases, tacrine, donepezil, rivastigmine, galantamine, other anti-dementia drugs, memantine, or ginkgo biloba.

In another embodiment, suitable active pharmaceutical ingredients can comprise other nervous system active drug substances, such as, for example: parasympathomimetics, anticholinesterases, neostigmine, pyridostigmine, distigmine, ambenonium, choline esters, carbachol, bethanechol, and other parasympathomimetics, such as, for example, pilocarpine, or choline alfoscerate.

Active drug substances used in addictive disorders, such as, for example: nicotine, bupropion, varenicline, disulfiram, calcium carbimide, acamprosate, naltrexone, buprenorphine, methadone, levacetylmethadol, lofexidine, betahistine, cinnarizine, flunarizine, acetylleucine, gangliosides and ganglioside derivatives, tirilazad, riluzole, xaliproden, hydroxybutyric acid, or amifampridine.

In another embodiment, suitable active pharmaceutical ingredients can comprise opium alkaloids and derivatives, such as, for example: ethylmorphine, hydrocodone, codeine, opium alkaloids with morphine, normethadone, noscapine, pholcodine, dextromethorphan, thebacon, dimemorfan, acetyldihydrocodone, benzonatate, benproperine, clobutinol, isoaminile, pentoxyverine, oxolamine, oxeladin, clofedanol, pipazetate, bibenzonium bromide, butamirate, fedrilate, zipeprol, dibunate, droxypropine, prenoxdiazine, dropropizine, cloperastine, meprotixol, piperidione, tipepidine, morclofone, nepinalone, levodropropizine, or dimethoxanate.

In another embodiment, the active pharmaceutical ingredient may be a substance with abuse potential that presents a safety risk. Such active drug substance may include: 1-(1-phenylcyclohexyl)pyrrolidine, 1-(2-phenylethyl)-4-phenyl-4-acetoxypiperidine, 1-[1-(2-thienyl)-cyclohexylpiperidine, 1-[1-(2-thienyl)cyclohexyl]pyrrolidine, 1-methyl-4-phenyl-4-propionoxy-piperidine, 1-phenylcyclohexylamine, 1-piperidinocyclohexanecarbonitrile, 2,5-dimethoxy-4-ethylamphetamine, 2,5-dimethoxyamphetamine, 2C-B-(4-bromo-2,5-dimethoxy)enethylamine), 2C-D (2,5-dimethoxy-4-methylphenethylamine), 2C-I (4-iodo-2,5-dimethoxyphenethylamine), 2C-T-2 (2,5-dimethoxy-4-ethylthiophenethylamine), 2C-T-4 (2,5-dimethoxy-4-isopropyl thiophenethylamine), 2C-T-7 (2,5-dimethoxy-4-(n)-propylthiophenethylamine), 3,4-methylenedioxymethamphetamine, 3,4,5-trimethoxyamphetamine, 3,4-methylenedioxyamphetamine, 3,4-methylenedioxy-N-ethylamphetamine,3-methylfentanyl,3-methylthiofentanyl, 4-brorno-2,5-dimethoxyamphetamine, 4-bromo-2,5-dimethoxyphenethylamine, 4-methoxyamphetamine, 4-methyl-2,5-dimethoxyamphetamine, 4-methylaminorex (cis isomer), 5-MeO-DIPT (5-methoxy-N,N-dii sopropyltryptamine), 5-MeO-DMT (5-methoxy-N,N-dimethyltryptamine), 5-methoxy-3,4-methylenedioxyamphetamine, acetorphine, acetorphine, acetyl-alpha-methylfentanyl, acetyl-alpha-methylfentanyl, acetyldihydrocodone, acetylmethadol, acetylmethadol, alfentanil, allobarbital, allylprodine, alphacetylmethadol except levo-alphacetylmethadol, alpha-ethyltryptamine, alphameprodine, alphamethadol, alphamethadol, alpha-methylfentanyl, alpha-methylthiofentanyl, alphaprodine, alprazolam, amfepramon, amfetaminil, amineptin, aminorex, amobarbital, amphetamine, dextroamphetamine, amilnitrite (all isomers of the amyl group), anabolic steroids, anileridine, aprobarbital, barbital, barbituric acid derivative, BDB (3,4-methylenedioxyphenyl)-2-butanamine), benzethidin, benzethidine, benzoylecgonine, benzphetamine, benzphetamine, benzylmethylcetone, benzylmorphine, betacetylmethadol, beta-hydroxy-3-methylfentanyl, beta-hydroxyfentanyl, betameprodine, betameprodine, betamethadol, betaprodine, bezitramide, bezitramide, boldenone, brolamfetamine, bromazepam, brotizolam, bufotenine, buprenorphine, butabarbital, butalbital, butobarbital, butorphanol, BZP (A2)(1-benzylpiperazin), camazepam, cannabis, carfentanil, cathaedulis, cathine, cathinone, chloral betaine, chloral hydrate, chlordiazepoxide, chlorhexadol, chlorotestosterone (same as clostebol), chlorphentermine, clobazam, clonazepam, clonitazene, clonitazene, clorazepate, clortermine, clostebol, clotiazepam, cloxazolam, coca leaves, cocaine, codeine, codeine and isoquinoline alkaloid, codeine methylbromide, codeine-N-oxide, codoxime, cyclobarbital (hexemal NFN), cyprenorphine, dehydrochlormethyltestosterone, delorazepam, desomorphine, dexamfetamine, dexfenfluramine, dexmethylphenidate, dextromoramide, dextropropoxyphene, diacetylmorphine, diampromide, diazepam, dichloralphenazone, diethylpropion, diethylthiambutene, diethyltryptamine, difenoxin, dihydrocodone, dihydroetorphine, dihydromorphine, dihydrotestosterone, dimenoxadol, dimepheptanol, dimethylthiambutene, dimethyltryptamine, dioxaphetyl butyrate, diphenoxylate, dipipanone, diprenorphine, dronabinol, drostanolone, drotebanol, ecgonine, estazolam, ethchlorvynol, ethinamate, ethyl loflazepate, ethylestrenol, ethylmethylthiambutene, ethylmorphine, ethylmorphine, eticyclidine, etilamfetamine, etonitazene, etorphine, etoxeridine, etryptamine, fencamfamin, fenethylline, fenetylline, fenfluramine, fenproporex, fentanyl, fludiazepam, flunitrazepam, fluoxymesterone, flurazepam, formebolone, fungi and spores of the species psilocybe semilanceata, furethidine, gamma hydroxybutyric acid, glutethimide, halazepam, haloxazolam, heroine, hydrocodone, hydrocodone & isoquinoline alkaloid, hydromorphinol, hydromorphone, hydroxypethidine, ibogaine, isobutyl nitrite, isomethadone, ketamine, ketazolam, ketobemidone, levamfetamine, levo-alphacetylmethadol, levo-methamphetamine, levomethorphan, levomoramide, levophenacylmorphan, levorphanol, lisdexamfetamine, loprazolam, lorazepam, lormetazepam, lysergic acid, lysergic acid amide, lysergic acid diethylamide, marijuana, mazindol, MBDN (N-methyl-1-(3,4-methylenedioxyphenyl)-2-butanamine), mCPP (1-(3-chlorphenyl)piperazine), mebutamate, meclo qualone, medazepam, mefenorex, MeOPP (1-(4-methoxyphenyl)piperazine), meperidine, meperidine intermediate, meprobamate, mescaline, mesocarb, mesterolone, metamfetamine, metazocine, methadone, methadone intermediate, methamphetamine, methandienone, methandrolone, methandriol, methandrostenolone, methaqualone, methcathinone, methenolone, methohexital, methyldesorphine, methyldihydromorphine, methylphenidate, methylphenobarbital (mephobarbital), methyltestosterone, methyprylone, metopone, mibolerone, midazolam, modafinil, moramide-intermediate, morpheridine, morphine, morphine methylbromide, morphine methylsulfonate, morphine-N-oxide, myrophine, N,N-dimethylamphetamine, nabilone, nalorphine, nandrolone, N-ethyl-1-phenylcyclohexylamine, N-ethyl-3-piperidyl benzilate, N-ethylamphetamine, N-hydroxy-3,4-methylenedioxyamphetamine, nicocodeine, nicocodine, nicodicodine, nicomorphine, nimetazepam, nitrazepam, N-methyl-3-piperidyl benzilate, noracymethadol, norcodeine, nordiazepam, norethandrolone, norlevorphanol, normethadone, normorphine, norpipanone, norpipanone, opium, oxandrolone, oxazepam, oxazolam, oxycodone, oxymesterone, oxymetholone, oxymorphone, para-fluorofentanyl, parahexyl, paraldehyde, pemoline, pentazocine, pentobarbital, petrichloral, peyote, phenadoxone, phenampromide, phenazocine, phencyclidine, phendimetrazine, phenmetrazine, phenobarbital, phenomorphan, phenoperidine, phentermine, phenylacetone, pholcodine, piminodine, pinazepam, pipradrole, piritramide, PMMA (paramethyxymethyl amphetamine), prazepam, proheptazine, properidine, propiram, psilocybine, psilocine, pyrovalerone, quazepam, racemethorphane, racemoramide, racemorphane, remifentanil, *salvia* divinorum, salvinorin A, secobarbital, secobarbital, sibutramine, SPA, stanolone, stanozolol, sufentanil, sulfondiethylmethane, sulfonethylmethane, sulfonmethane, talbutal, temazepam, tenamfetamine, testolactone, testosterone, tetrahydrocannabinols, tetrazepam, TFMPP (1-(3-triflourmethylphenyl)piperazine), thebacon, thebaine, thiamylal, thiofentanyl, thiopental, tiletamine and zolazepam in combination, tilidine, trenbolone, triazolam, trimeperidine, vinbarbital, zaleplon, zipeprol, zolpidem, or zopiclone.

Other suitable examples of active drug substances suitable for use in the pharmaceutical compositions described herein include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodone, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narcine, nicomorphine, norlevorphanol, normethadone, nalorphine, normorphine, norpipanone, opium, oxycodone, oxycodeine, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, thebaine, levo-alphacetylmethadol (LAAM), remifentanil, carfentanyl, ohmefentanyl, MPPP, prodine, PEPAP, levomethorphan, etorphine, lefetamine, loperamide, diphenoxylate, or pethidine.

Other examples of active drug substances suitable for use in the pharmaceutical compositions described herein include anabolic steroids, cannabis, cocaine, or diazepam.

In another embodiment, the active drug substance comprises the therapeutic classes including non-steroidal anti-inflammatory substances or antirheumatic active drug substances.

In other embodiments, the active drug substance comprises analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alfa-adrenergic, serotonin, H3 antagonists used for ADHD or nootropics agents used in addictive disorders.

In other embodiments, the active drug substance comprises therapeutic classes including anaesthetics, centrally acting analgesics, sedative-hypnotics, anxiolytics, appetite suppressants, decongestants, antitussives, antihistamines, antiemetics, antidiarrheals, and drugs used to treat narcolepsy, or attention deficit hyperactivity disorder.

In another embodiment, the active drug substance is associated with abuse syndromes and the active drug substance may, for example, be selected from opioids, CNS depressants, CNS stimulants, cannabinoids, nicotine-like compounds, glutamate antagonists, or N-methyl-D-aspartate (NMDA) antagonists.

In another embodiment, the active drug substance is an analgesic. Examples of analgesics suitable for use in the pharmaceutical compositions described herein include, for example, opioids, natural opium alkaloids, morphine, opium, hydromorphone, nicomorphine, oxycodone, dihydrocodone, diamorphine, tapentadol, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics such as, for example, rimazolium, glafenine, floctafenine, viminol, nefopam, flupirtine, or ziconotide.

In another embodiment, the active drug substance is an opioid. Where an opioid is included as an active drug substance, the opioid may comprise naturally occurring opioids, synthetic opioids, or semisynthetic opioids.

In other embodiment, the active drug substance comprises amfetamine, dexamfetamine, lisdexamfetamine, metamfetamine, methylphenidate, dexmethylphenidate, or combinations thereof.

In another embodiment, the pharmaceutical compositions disclosed herein includes an opioid, the opioid is selected from buprenorphine, codeine, dextromoramide, dihydrocodone, fentanyl, hydrocodone, hydromorphone, morphine, pentazocine, oxycodeine, oxycodone, oxymorphone, norhydrocodone, noroxycodone, morphine-6-glucuronode, tramadol, tapentadol, or dihydromorphine.

Where an opioid is used as an active drug substance, the opioid may be present in any of its crystalline, polymorphous, semi-crystalline, and amorphous or polyamorphous forms. Furthermore, in another embodiment, an opioid used as an active drug substance may be present in one or more forms selected from its crystalline, polymorphous, semi-crystalline, or amorphous or polyamorphous forms.

Some embodiments of the pharmaceutical compositions disclosed herein include an opioid as an active drug substance, the active drug substance is selected from morphine, oxycodone, hydrocodone, hydromorphone, norhydrocodone, oxymorphone, noroxycodone, morphine-6-glucuronode and pharmaceutically acceptable salts thereof, including oxycodone hydrochloride, hydrocodone bitartrate, hydromorphone hydrochloride or morphine sulphate pentahydrate.

In other embodiments, the pharmaceutical compositions as described herein are suitable for use for water soluble as well as slightly soluble or insoluble active drug substances.

In another embodiment, all of the above mentioned active drug substances may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the pharmaceutical compositions described herein may comprise pharmaceutically acceptable salts of any of the above mentioned active drug substances.

In another embodiment, the active pharmaceutical ingredient is hydrocodone or oxycodone or a pharmaceutically acceptable salt form of either hydrocodone or oxycodone.

Pharmaceutically acceptable salts forms are those formed by contacting hydrocodone or oxycodone free base with a suitable acid in a suitable solvent under suitable conditions that will form a form of hydrocodone or oxycodone acid addition salt. Suitable acids include hydrochloric acid, camphorsulfonic acid, hydrobromic acid, sulfuric acid, methanesulfonic acid, formic acid, acetic acid, oxalic acid, succinic acid, tartaric acid, mandelic acid, malic acid, salicylic acid, fumaric acid, lactic acid, citric acid, glutamic acid, and/or aspartic acid.

The term "pharmaceutically acceptable salts" of an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, pharmaceutically acceptable opioid salts can comprise sulphate salts, hydrochloride salts, and bitartrate salts.

In another embodiment, the active pharmaceutical ingredient may be in any of its crystalline, polymorphous, semi-crystalline, amorphous or polyamorphous forms or mixtures thereof.

The concentration of the active drug substance in the pharmaceutical composition for use according to the disclosure depends on the specific active drug substance, the disease to be treated, the condition of the patient, the age, and gender of the patient, etc. The above-mentioned active drug substances may be known active drug substances and a person skilled in the art will be able to find information as to the dosage of each active drug substance and, accordingly, will know how to determine the amount of each active drug substance in the pharmaceutical composition.

The active pharmaceutical ingredient may be a new chemical entity for which the amount of information is limited. In such cases, the dosage has to be evaluated based on available preclinical and/or clinical data.

In one embodiment described herein, the pharmaceutical composition comprises soft capsule shell comprising a matrix comprising an active pharmaceutical ingredient.

In one embodiment described herein, the soft capsule shell has the composition of Table 4, including all possible iterations of the specified ranges that provide 100% for the total weight percentage, including or excluding the optional colorings, flavorings, or excipients.

TABLE 4

Exemplary soft gelatin capsule composition

| Component | Exemplary Component | Weight Percentage (%) |
|---|---|---|
| Film-forming polymer | Gelatin | 20-36 (Gelatin) |
| Plasticizer | Glycerol | 10-30 |
| Solvent | Water | 20-70 |
| Opacifier (optional) | Titanium dioxide | 0.5-1.5 |
| Coloring agent (optional) | Various | 0.05-0.1 |
| TOTAL | | 100% |

Film-former polymers that are useful for creating soft capsules are gelatin, hydroxypropylmethylcellulose (HPMC) or carrageenan (e.g., iota carrageenan and kappa carrageenan). In one aspect of the enteric soft capsule shell described herein, the film-forming polymer is gelatin. In another aspect of the enteric soft capsule shell described herein, the film-forming polymer is carrageenan.

Plasticizers that are useful for creating soft capsules as described herein are glycerol, sorbitol, polyethylene glycols, or combinations thereof. The weight ratio between the film-forming polymer, plasticizer, and solvent is adjusted so that the gel mass is flowable and not too viscous, and can be made into soft capsules using rotary die encapsulation methods.

In one embodiment, the enteric soft capsule shell has the exemplary composition shown in Table 5.

TABLE 5

Exemplary Soft Capsule Shell Composition

| Component | Percent weight (%) |
|---|---|
| Gelatin | 43 |
| Glycerol | 20 |
| Titanium dioxide (optional) | 0.7 |
| Coloring agent (optional) | 0.1 |
| Water | 36.2 |
| TOTAL | 100% |
| Final pH | ~4-7 |
| Ratio total plasticizer to gelatin | 20:43 (0.46:1) |
| Water content in dried soft capsule shell: | 8-15% |

In one embodiment described herein, the soft capsule comprises about 43% of at least one film-forming polymer; about 20% of at least one plasticizer; about 36% water; optionally, about 0.7% titanium dioxide; and optionally, about 0.1% of at least one coloring agent.

In one embodiment described herein, the enteric soft capsule described herein comprises a composition of about 3% to about 10% film forming polymer (e.g., a composition of carrageenan); about 10% to about 30% filler; about 10% to about 30% plasticizer; and about 30% to about 70% solvent.

In one embodiment, the weight percentage range of film-forming polymer of the soft capsule described herein is about 20% to about 45%, including all integers within the specified range. In one aspect, the film-forming polymer weight percentage is about 20%. In one aspect, the film-forming polymer weight percentage is about 25%. In one aspect, the film-forming polymer weight percentage is about 30%. In one aspect, the film-forming polymer weight percentage is about 35%. In one aspect, the film-forming polymer weight percentage is about 38%. In another aspect, the film-forming polymer weight percentage is about 42%. In another aspect, the film-forming polymer weight percentage is about 44%.

In one embodiment, the weight percentage range of plasticizer is about 15% to about 22%, including all iterations of integers with the specified range. In one aspect, the plasticizer weight percentage is about 17%. In another aspect, the plasticizer weight percentage is about 18.5%. In another aspect, the plasticizer weight percentage is about 20%.

In one embodiment, the weight percentage ratio range of plasticizer to film-forming polymer is about 0.33:1 to about 0.56:1, including all iterations of iterations of ratios with the specified range. In one embodiment, the weight percentage ratio range of plasticizer to film-forming polymer is about 0.38:1. In one embodiment, the weight percentage ratio range of plasticizer to film-forming polymer is about 0.42:1. In one embodiment, the weight percentage ratio range of plasticizer to film-forming polymer is about 0.46:1. In one embodiment, the weight percentage ratio range of plasticizer to film-forming polymer is about 0.52:1.

In one aspect, soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing soft capsules comprising the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the soft capsule shell described herein, encapsulates a matrix fill as described herein. In another embodiment described herein, the soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

In another embodiment described herein, the pharmaceutical composition comprises an enteric soft capsule shell comprising a matrix fill comprising an active pharmaceutical ingredient.

Enteric soft capsules are described in International Patent Application Publication No. WO 2004/030658; U.S. Patent Application Publication No. US 2006/0165778; and U.S. Pat. No. 8,685,445, each of which is incorporated by reference herein for such teachings. The enteric soft capsule shell may comprise one or more film forming polymers, one or more enteric acid-insoluble polymers, one or more plasticizers, one or more alkali-neutralizing agents, one or more solvents, optionally one or more colorants, and optionally one or more flavorings or other conventionally accepted pharmaceutical excipients or additives.

Film-former polymers that are useful for creating enteric soft capsules are gelatin, hydroxypropylmethylcellulose (HPMC) or carrageenan (e.g., iota carrageenan and kappa carrageenan). In one aspect of the enteric soft capsule shell described herein, the film-forming polymer is gelatin. In another aspect of the enteric soft capsule shell described herein, the film-forming polymer is carrageenan.

Examples of enteric, acid-insoluble polymers are acrylic and methacrylate acid copolymers, cellulose acetate phthalate (CAP), cellulose acetate butyrate, hydroxypropylmethylcellulose phthalate (HPMCP), algenic acid salts such as sodium or potassium alginate, or shellac. Poly(methacylic acid-co-methyl methacrylate) anionic copolymers based on methacrylic acid and methyl methacrylate are particularly stable and are preferred in some embodiments. Poly(meth)acrylates (methacrylic acid copolymer), available under the trade name EUDRAGIT® (Evonik Industries AG, Essen, Germany), are provided as powder or aqueous dispersions. In one aspect, the methacrylic acid copolymer can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; or other poly(meth)acrylate polymers. In one aspect, the enteric polymer is EUDRAGIT® L 100, a methacrylic acid copolymer, Type A. Acid-insoluble polymer specifications are detailed in the United States Pharmacopoeia and in various monographs.

Plasticizers that are useful for creating enteric soft capsules as described herein are glycerol, sorbitol, polyethylene glycol, citric acid, citric acid esters, such as tri-ethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods.

In one embodiment, enteric soft capsule shell compositions can be made by dissolving the enteric acid-insoluble polymer in an aqueous solution of an alkali neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In one embodiment, the final pH does not exceed 8.5. The volatile alkali neutralizing agent, ammonia is preferred. The film-forming polymer can then be combined with the plasticizer and solvent and then blended with the acid-insoluble gel to make a final homogeneous mix in a heat-controlled vessel and can be degassed by using vacuum. The fugitive ammonia evaporates during degassing. Using the foregoing process, the alkali concentrations do not require an additional step such as heating or neutralizing with acid in order to neutralize the gel mass.

In another embodiment described herein, an enteric soft capsule shell can be made by using an aqueous dispersion of the acid-insoluble polymer by adding alkaline materials such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment, enteric acid-insoluble polymers in the form of salts of the above-mentioned bases or alkalis can be dissolved directly in water and mixed with the plasticizer-wetted, film-forming polymer.

In one embodiment, an enteric soft capsule shell has the composition of Table 6, including all possible iterations of the specified ranges that provide 100% for the total weight percentage, including or excluding the optional, excipients, opacifiers, colorants, and flavorings.

TABLE 6

Exemplary Enteric Soft Capsule Shell Composition

| Component | Exemplary Component | Composition Range (%) |
|---|---|---|
| Film-forming polymer | Gelatin | 20-36 |
| Enteric, acid insoluble polymer | Methacrylic Acid Copolymer | 8-20 |
| Plasticizer | Glycerol, Triethyl citrate | 15-22 |
| Alkali neutralizing agents | NH$_4$OH (30%), NaOH | 1-5 |
| Solvent | Water | 20-40 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |

In one embodiment, an enteric soft capsule shell comprises a composition of about 30% film forming polymer (e.g., gelatin); about 10% enteric, acid insoluble polymer; about 20% plasticizer; about 1% alkali neutralizing agent; and about 37% solvent.

In one embodiment described herein, the enteric soft capsule described herein comprises a composition of about 3% film forming polymer (e.g., a composition of carrageenan); about 10% enteric, acid insoluble polymer; about 10% filler; about 10% plasticizer; about 1% alkali neutralizing agent; about 2% sealant; and about 60% solvent.

In one embodiment, the weight percentage range of total polymer content (i.e., film forming polymer and enteric acid-insoluble polymer) of the enteric soft capsule described herein is about 30% to about 45%, including all integers within the specified range. In another embodiment, the weight percentage range of total polymer content (i.e., film forming polymer and enteric acid-insoluble polymer) of the enteric soft capsule described herein is about 9% to about 35%, including all integers within the specified range. In one aspect, the total polymer weight percentage is about 40%. In another aspect, the total polymer weight percentage is about 42%. In another aspect, the total polymer weight percentage is about 45%. In another aspect, the total polymer weight percentage is about 38%. In another aspect, the total polymer weight percentage is about 12%. In another aspect, the total polymer weight percentage is about 16%.

In one embodiment, the weight percentage range of total plasticizer is about 15% to about 22%, including all iterations of integers with the specified range. In one aspect, the total plasticizer weight percentage is about 19%. In another aspect, the total plasticizer weight percentage is about 17.7%. In another aspect, the total plasticizer weight percentage is about 18.9%. In another aspect, the total plasticizer weight percentage is about 19.3%.

In one embodiment, the alkali neutralizing-agent is ammonia (ammonium hydroxide; 30% w/v) that is added to comprise a weight percentage of about 1 to about 5% of the total enteric soft capsule composition. In one aspect, 30% w/v ammonia is added to comprise a weight percentage of about 2%. In another aspect, 30% w/v ammonia is added to a weight percentage of about 1.7%. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali. In one aspect, practically all of the ammonia is evaporated except for ammonium ions comprising salts with other moieties in the composition.

In one embodiment, the weight ratio range of film forming polymer to enteric acid insoluble polymer (film forming: enteric) is about 25:75 (≈0.33) to about 40:60 (≈0.67) (i.e., ≈0.33-0.67), including all iterations of ratios within the specified range. In one aspect, the ratio of film forming polymer to enteric acid insoluble polymer is about 30:70 (≈0.43). In another aspect, the ratio of film forming polymer to enteric acid insoluble polymer is about 28:72 (≈0.38).

In another embodiment described herein, the weight ratio range of film forming polymer (i.e., total carrageenan composition) to enteric acid insoluble polymer (film forming: enteric) in the enteric soft gel composition is about 3:9 (≈0.3) to about 4:3 (≈1.3) (i.e., ≈0.3-1.3), including all ratios within the specified range. In some aspects, the ratio of film forming polymer to enteric acid insoluble polymer in the gel mass is about 1:3 (≈0.33), about 1:2.5 (≈0.4), about 1:2 (≈0.5), about 1:1.6 (≈0.6), about 1:1.25 (≈0.8), about 1:1 (≈1), about 1.1:1 (≈1.1), about 1.21 (≈1.2), or about 1.3:1 (≈1.3). In one aspect, the ratio of film forming polymer to enteric acid insoluble polymer in the gel mass is about 1:2.5 (≈0.4). In another aspect, the ratio of film forming polymer to enteric acid insoluble polymer is about 1:3 (≈0.3).

In one embodiment, the weight ratio of total plasticizer to film forming polymer is about 20:40 to 21:30 (i.e., ≈0.5-0.7), including all iterations of ratios within the specified range. In one aspect, the weight ratio of total plasticizer to film forming polymer is about 20:40 (≈0.5). In another aspect, the weight ratio of total plasticizer to film forming polymer is about 21:30 (≈0.7). In another aspect, the weight ratio of total plasticizer to film forming polymer is about 19:29 (≈0.65). In another aspect, the weight ratio of total plasticizer to film forming polymer is about 19.3:29.2 (≈0.66).

In one embodiment, the weight ratio of total plasticizer to enteric acid insoluble polymer is about 1:1 to about 2:1 (≈1-2), including all iterations of ratios within the specified range. In one aspect, the weight ratio of total plasticizer to enteric acid insoluble polymer is about 11:10 (≈1.1). In another aspect, the weight ratio of total plasticizer to enteric acid insoluble polymer is about 14:10 (≈1.4). In another aspect, the weight ratio of total plasticizer to enteric acid insoluble polymer is about 17:10 (≈1.7). In another aspect, the weight ratio of total plasticizer to enteric acid insoluble polymer is about 20:10 (≈2). In another aspect, the weight ratio of total plasticizer to enteric acid insoluble polymer is about 19.3:11.2 (≈1.73).

In one embodiment, the weight ratio range of total plasticizer to total polymer (film forming and enteric acid insoluble polymer) is about 18:45 to about 20:40 (i.e., ≈0.40-0.5), including all iterations of ratios within the specified range. In one aspect, the weight ratio range of total plasticizer to total polymer is about 18:45 (≈0.40). In another aspect, the weight ratio range of total plasticizer to total polymer is about 19:40 (≈0.475). In another aspect, the weight ratio range of total plasticizer to total polymer is about 20:40 (≈0.5). In another aspect, the weight ratio range of total plasticizer to total polymer is about 19.3:40.4 (≈0.477).

In one embodiment, the solvent comprises about 20% to about 40% of the enteric soft capsule composition, including all integers within the specified range. In one embodiment, the solvent is water. The quantity of water in the composition varies depending on the quantities of the other ingredients. For example, the quantity of opacifier, colorant, flavoring, or other excipients can change the percentage of water present the composition. In one embodiment, the weight percentage of water is as much as suffices to bring the total weight percentage to 100% (i.e., quantum sufficiat; q.s.). In another embodiment, the water comprises about 20%, about 25%, about 30%, about 35%, or about 40% of the enteric soft capsule composition. In another embodiment, water comprises about 35% to about 40% of the enteric soft capsule composition. In one embodiment, water comprises about 37% of the composition.

In one embodiment, the final moisture (water) content of the enteric soft capsule is from about 8% to about 15%, including all integers within the specified range. In another embodiment, the moisture content is about 8% to about 12%, including all integers within the specified range. In one aspect, the final moisture content is about 8%. In one aspect, the final moisture content is about 9%. In one aspect, the final moisture content is about 10%. In one aspect, the final moisture content is about 11%. In another aspect, the final moisture content is about 12%.

In one embodiment, the enteric soft capsule shell has the exemplary composition shown in Table 7.

TABLE 7

Exemplary Enteric Soft Capsule Shell Composition

| Component | Percent weight |
|---|---|
| Gelatin | 29.2 |
| Methacrylic Acid Copolymer (EUDRAGIT ® L100) | 11.2 |
| Glycerol | 18.0 |
| Triethyl citrate | 1.3 |
| Ammonium hydroxide | 1.7 |

TABLE 7-continued

Exemplary Enteric Soft Capsule Shell Composition

| Component | Percent weight |
|---|---|
| Titanium dioxide | 1.5 |
| Water | 37.1 |
| TOTAL | 100% |
| Final pH | ~4-9 |
| Total polymer % weight (gelatin + enteric) | 40.4% |
| Gelatin % wt of total polymer (gelatin + enteric) | 72.4% |
| Enteric % wt of total polymer (gelatin + enteric) | 27.6% |
| Ratio of Enteric to Gelatin | 11.2:29.2 (0.38) |
| Total plasticizer % weight (glycerol + triethyl citrate) | 19.3% |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15% |

In one embodiment, the enteric soft capsule shell comprises about 30% gelatin; about 10% poly(methyl) acrylate copolymer; about 18% glycerol; about 1% triethyl citrate; about 1.5% ammonia; about 37% water; and about 1.5% titanium dioxide.

One embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

In some embodiments, the enteric soft capsule shell does not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. In some embodiments, the enteric soft capsules made using the compositions described herein remain intact in hydrochloric acid or simulated gastric fluid for at least two hours and the capsules readily release their contents upon shifting the pH of the solution to ca. 6.8, such as that of simulated intestinal fluid. In one aspect, the enteric soft capsule is resistant to dissolution at about pH 1.2 for at least about 2 hours. In another aspect, the enteric soft capsule begins dissolution at pH of about 6.8 within about 10 min.

In another embodiment, the final enteric capsule composition provides films of increased strength without substantially compromising film elasticity. Moreover, films made from the enteric soft capsule compositions as described herein can be sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The same thicknesses, capsule types and sizes as described herein for soft capsules can also be used for enteric soft capsules.

In another embodiment, the capsule is a soft capsule comprising a film-forming polymer that is stable at higher temperatures (e.g., about 50° C. to about 80° C.). An exemplary film-forming polymer is carrageenan (e.g., kappa or iota carrageenan). Exemplary, non-limiting soft capsules comprising carrageenan are described in the International Patent Application Publication No. WO 2003/061633; U.S. Patent Application Publication No. US 2004/0052839; and U.S. Pat. Nos. 6,949,256 and 7,887,838, each of which is incorporated by reference herein for such teachings. In one aspect, soft capsules comprising a film-forming polymer stable at high temperatures allow for matrix fills having a higher viscosity to be encapsulated minimizing the use of additional plasticizers. The increased encapsulation temperature, for example, from about 50° C. to about 80° C. allows for a viscous matrix at a lower temperature to exhibit flowability for encapsulation by the methods described herein (e.g., rotary die encapsulation).

In another embodiment, the capsule shell is a hard capsule shell. In one aspect, the hard capsule shell may comprise the abuse deterrent matrices described herein. Any hard capsule shell, for example hard capsule shells comprising gelatin, HPMC, or pullulan, including hard capsule shells exhibiting enteric properties, maybe used with the abuse deterrent matrix fills described herein. Hard capsule shells are known in the art and are described by Kathpalia et al., *J. Adv. Pharm. Edu. & Res.* 4(2): 165-177 (2014), which is incorporated by reference herein for its specific teachings thereof.

In another embodiment, the capsule shell may be a soft capsule shell that comprises multiple charges. The charges may be spatially separated so that a first portion of the capsule shell has one or more charges and a second portion of the capsule shell has one or more charges. In some embodiments described herein, the ionic charges result from charged polymers included in the capsule shell. Thus, in some aspects, the capsule may comprise a portion that has a positive charge and a second portion that has a negative charge.

In one embodiment, the positive soft capsule shell comprises a type gelatin A; dimethylaminoethyl methacrylate copolymer; glycerol; HCl, water and optionally polyethylene oxide; an opacifier, colorant, flavoring, or other pharmaceutical excipient. Type A gelatins useful for the charged soft capsule shells described herein has approximately 80 millimoles of free carboxyl groups per 100 g of protein with an isoelectric point (PI) of about 7.0-9.0. Exemplary and non-limiting polymers for use in the positive charged soft capsule shells described herein are shown in Table 8.

In one embodiment, the negative soft capsule shell comprises a type gelatin B; methacrylic acid copolymer; glycerol; ammonium hydroxide, HCl, water and optionally polyethylene oxide; an opacifier, colorant, flavoring, or other pharmaceutical excipient. Type B gelatins useful for the charged soft capsule shells described herein has approximately 100-115 millimoles of free carboxyl groups per 100 g of protein with an isoelectric point (PI) of about 4.7-5.2. Exemplary and non-limiting polymers for use in the positive charged soft capsule shells described herein are shown in Table 9.

TABLE 8

Exemplary Polymers Useful for Positive Soft Capsule Shell Compositions

| EX1 | EX2 | EX3 |
|---|---|---|
| Gelatin (Type A) | Gelatin (Type A) | Gelatin (Type A) Iso Elec. Pt. 8.9 (From Nitta) |
| Dimethylaminoethyl Methacrylate Copolymer (EUDRAGIT ® EPO) | Dimethylaminoethyl Methacrylate Copolymer (EUDRAGIT ® EPO) | Dimethylaminoethyl Methacrylate Copolymer (EUDRAGIT ® EPO) |
| Glycerol | Glycerol | Glycerol |
| HCl | HCl | HCl |
| Water | Water | Water |
|  | | Polyethylene oxide |

TABLE 9

Exemplary Polymers Useful for Negative Soft Capsule Shell Compositions

| EX4 | EX5 | EX6 |
|---|---|---|
| Gelatin (Type B) | Gelatin (Type B) | Gelatin (Type B) Iso Elec. Pt. 4 (From Nitta) |
| Methacrylic Acid Copolymer (EUDRAGIT ® L100) | Methacrylic Acid Copolymer (EUDRAGIT ® L100) | Iota-carrageenan |
| Glycerol | Glycerol | Glycerol |
| Ammonium Hydroxide | Ammonium Hydroxide | Water |
| 0.1 N HCl | 0.1 N HCl |  |
| Water | 1% Polyethylene oxide |  |
|  | Water |  |

In another embodiment the multiple charged soft capsule shell may be a dual charged capsule shell. As described herein, the dual charged soft capsule shell may comprise a first portion that is positively charged and a second portion that is negatively charged. The positive portion of the soft capsule shell may be prepared by forming a positive gel mass ribbon composition. Likewise, the negative portion of the soft capsule shell may be prepared by forming a negative gel mass ribbon composition. The two ribbon compositions may then be combined using standard rotary die encapsulation techniques to form a dual charged (positive and negative) total soft capsule shell. This total soft capsule shell may further encapsulate one or more active pharmaceutical ingredients (e.g., drug-resinate) in an abuse deterrent matrix as described herein. Exemplary and non-limiting dual charged soft capsule shell gel mass ribbon compositions are provided in Table 10.

In another embodiment, a soft capsule shell may be further coated with one or more charged film compositions according to Tables 8-10. In one aspect, a charged soft capsule shell comprising the composition of any one of Tables 8-10 may further be coated with an additional film composition according to any one of Tables 8-10.

TABLE 10

Exemplary Dual Charged Soft Capsule Shell Gel Mass Ribbon Compositions

| Components | Positive Percentage (%) | Negative Percentage (%) |
|---|---|---|
| Gelatin | 20-35 | 20-35 |
| Methacrylic Acid Copolymer (EUDRAGIT ® L 100) | — | 5-20 |
| Dimethylaminoethyl Methacrylate Copolymer (EUDRAGIT ® EPO) | 4-22 | — |
| Glycerol | 5-25 | 5-25 |
| Triethyl citrate | | 0.5-3 |
| HCl | 0.5 | |
| Ammonium hydroxide | — | 0.5-5 |
| Titanium dioxide | — | 0.5-5 |
| Water | 30-50 | 30-50 |
| TOTAL | 100 | 100 |

Another embodiment described herein is an oral pharmaceutical composition comprising a solid dosage form such as a powder or a compressed tablet. In one aspect, the composition is a non-layered homogeneous powder suspension. In one aspect, the composition comprises one or more active pharmaceutical ingredients and one or more sequestering agents. In one aspect, the sequestering agent comprise one or more ionizable polymers, including cationic, anionic polymers, or zwitterionic polymers. In one aspect, the sequestering agent is an ion exchange resin. In one aspect the one or more active pharmaceutical ingredients and one or more sequestering agents are not pre-bound (e.g., are not a resinate complex). In one aspect, the composition comprises a powder suspension of the active pharmaceutical ingredients, the sequestering agents, and optionally, one or more pharmaceutically acceptable excipients.

One embodiment described herein is an oral pharmaceutical composition comprising (a) a solid dispersion of an active pharmaceutical ingredient or a salt thereof as described herein; (b) one or more sequestering agents; and (c) one or more pharmaceutically acceptable excipients. In some embodiments, the composition further comprises (d) one or more fillers (e) one or more binders, (f) one or more disintegrants, or (g) one or more lubricants. In one aspect, the filler comprises one or more of lactose, lactose monohydrate, glucose, fructose, sucrose, sorbitol, mannitol, dicalcium phosphate dihydrate, cellulose, ethyl cellulose, methyl cellulose, microcrystalline cellulose, crospovidone, or a combination thereof. In one aspect, the disintegrant comprises one or more of crospovidone, croscarmellose sodium, alginic acid, microcrystalline cellulose, polacrilin potassium, sodium starch glycolate, starch, pregelatinized starch, or a combination thereof. In one aspect, the lubricant comprises one or more of magnesium stearate, calcium stearate, zinc stearate, sodium stearyl fumarate, stearic acid, talc, glyceryl behenate, or a combination thereof. In one aspect, the pharmaceutical composition comprises one or more colorants, flavorings, binders, glidants, coatings, or other pharmaceutically acceptable excipients. In one aspect, the filler comprises microcrystalline cellulose and lactose monohydrate; the disintegrant comprises crospovidone; and the lubricant comprises magnesium stearate.

As described herein, the pharmaceutically acceptable compositions comprise pharmaceutically acceptable excipients, carriers, adjuvants, or vehicles, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of the embodiments described herein. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Another embodiment described herein comprises a pharmaceutical composition comprising an active pharmaceutical ingredient or a salt thereof as described herein, and one or more pharmaceutically acceptable excipients.

Another embodiment described herein comprises a pharmaceutical composition comprising a therapeutically effective amount of an active pharmaceutical ingredient or a salt thereof as described herein, and one or more pharmaceutically acceptable carriers or vehicles.

The compositions described herein may be administered using any amount and any route of administration effective for treating or lessening the severity of pain or non-pain diseases described herein. The exact amount of the active pharmaceutical active ingredient(s) required will vary from subject to subject, depending on the species, age, and general condition of the subject, the severity of the infection, the particular agent, its mode of administration, tolerance of the individual to the active ingredient, and the like. The compositions described herein are preferably formulated in dosage unit form for ease of administration and uniformity of dosage. The expression "dosage unit form" as used herein refers to a physically discrete unit of agent appropriate for the subject to be treated. The total daily usage of the compounds and compositions described herein will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts.

Solid dosage forms for oral administration include capsules, tablets, pills, powders, and granules. In such solid dosage forms, the active compound is mixed with at least one inert, pharmaceutically acceptable excipient including but not limited to: (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

As used herein, a "disintegrant" is an excipient that hydrates a pharmaceutical composition and aids in tablet dispersion. Examples of disintegrants include crospovidone, sodium croscarmellose, alginic acid, microcrystalline cellulose, polacrilin potassium, sodium starch glycolate, starch, pregelatinized starch, or combinations thereof.

As used herein, a "filler" is an excipient that adds bulkiness to a pharmaceutical composition. Examples of fillers include lactose, lactose monohydrate, glucose, fructose, sucrose, sorbitol, mannitol, dicalcium phosphate dihydrate, cellulose, ethyl cellulose, methyl cellulose, microcrystalline cellulose, crospovidone, or a combination thereof.

As used herein, a "binder" is an excipient that imparts a pharmaceutical composition with enhanced cohesion or tensile strength (e.g., hardness). Examples of binders include dibasic calcium phosphate, sucrose, corn (maize) starch, microcrystalline cellulose, and modified cellulose (e.g., hydroxymethyl cellulose).

As used herein, a "lubricant" is an excipient that is added to pharmaceutical compositions that are pressed into tablets. The lubricant aids in compaction of granules into tablets and ejection of a tablet of a pharmaceutical composition from a die press. Examples of lubricants include magnesium stearate, calcium stearate, zinc stearate, sodium stearyl fumarate, stearic acid, talc, glyceryl behenate, or a combination thereof.

As used herein, a "glidant" is an excipient that imparts a pharmaceutical composition with enhanced flow properties. Examples of glidants include colloidal silica or talc.

As used herein, a "surfactant" is an excipient that imparts pharmaceutical compositions with enhanced solubility and/or wetability. Examples of surfactants include sodium lauryl sulfate (SLS), sodium stearyl fumarate (SSF), polyoxyethylene 20 sorbitan mono-oleate (e.g., Tween™), or a combination thereof.

As used herein, a "colorant" is an excipient that imparts a pharmaceutical composition with a desired color. Examples of colorants include commercially available pigments such as FD&C coloring agents, titanium dioxide, iron oxide, or combinations thereof.

As used herein, a "flavoring" is an excipient that imparts a flavor or taste masking property to a pharmaceutical composition. Examples of flavorings include anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin, or combinations thereof.

As used herein a "coating agent" makes the dosage from smoother and easier to swallow, controls the release rate of the active ingredient, and makes the dosage from more resistant to the environment (extending its shelf life), or enhances the dosage form's appearance Examples of coating agents include sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein, or combinations thereof.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Another embodiment described herein is a kit for dispensing the oral pharmaceutical dosage form produced by any of the compositions or the methods described herein comprising: (a) at least one dosage form comprising one or more active pharmaceutical ingredients or salts thereof as described herein; (b) at least one moisture proof dispensing receptacle comprising blister or strip packs, an aluminum blister, a transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally (c) an insert comprising instructions, prescribing information, or warnings for an active pharmaceutical ingredient comprised by the pharmaceutical composition; or (d) directions for administration or any contraindications. In one aspect described herein, the kit is useful for treating pain or a medical condition according to any of the methods described herein.

One embodiment described herein, is a pharmaceutical composition comprising any of the formulations shown in the Tables or Examples described herein. Any of the components of the formulations shown in the Tables or Examples can be increased, decreased, combined, recombined, switched, or removed to provide for a formulation comprising about 100% by weight.

In another embodiment, the abuse deterrent pharmaceutical composition described herein provides a dosage of an active pharmaceutical ingredient described herein for administration to a subject. The dosage form can be administered, for example, to a subject, or a subject in need thereof. In one aspect, the subject is a mammal, or a mammal in need thereof. In one aspect, the subject is a dog. In one aspect, the subject is a human, or human in need thereof. In one aspect, the human or human in need thereof is a medical patient. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (≥18 years of age).

In one embodiment, the dosage may be administered to a human in need of management of moderate to severe chronic pain or neuropathic pain, when a continuous, persistent (around-the-clock) opioid analgesic is needed for an extended period of time.

The dosage form can be administered, for example, 1×, 2×, 3×, 4×, 5×, 6×, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition, including but not limited to, pain.

In one embodiment, the pharmaceutical composition described herein is administered in multiple dosages simultaneously. For example, two or more identical dosages are administered at one time. In another embodiment, two or more different dosages are administered at one time. Such dual or different simultaneous doses can be used to provide an effective amount of the pharmaceutical composition to a subject in need thereof.

In one embodiment, the abuse deterrent oral composition described herein, comprises one or more active pharmaceutical ingredients in an amount of about 1 mg, about 2, mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, or even more. Multiples of any of the forgoing quantities can be dispensed to achieve the therapeutic effect.

In another embodiment, the compositions described herein, comprise one or more active pharmaceutical ingredients in the range of about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, about 240 mg to about 250 mg; about 250 mg to about 500 mg, about 260 mg to about 500 mg, about 270 mg to about 500 mg, about 280 mg to about 500 mg, about 290 mg to about 500 mg, about 300 mg to about 500 mg, about 310 mg to about 500 mg, about 320 mg to about 500 mg, about 330 mg to about 500 mg, about 340 mg to about 500 mg, about 350 mg to about 500 mg, about 360 mg to about 500 mg, about 370 mg to about 500 mg, about 380 mg to about 500 mg, about 390 mg to about 500 mg, about 400 mg to about 500 mg, about 410 mg to about 500 mg, about 420 mg to about 500 mg, about 430 mg to about 500 mg, about 440 mg to about 500 mg, about 450 mg to about 500 mg, about 460 mg to about 500 mg, about 470 mg to about 500 mg, about 480 mg to about 500 mg, or about 490 mg to about 500 mg. Multiples of any of the forgoing quantities can be dispensed to achieve the therapeutic effect.

In one embodiment described herein, the compositions described herein may comprise an active pharmaceutical ingredient load (e.g., a drug load of one or more active pharmaceutical ingredients) of about 1% to about 90%, including each integer within the specified range. In one embodiment, the drug load can comprise about 1%, about 2%, about 2.5%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or even higher. In one aspect, the drug load is about 5%. In one aspect, the drug load is about 10%. In one aspect, the drug load is about 20%. In one aspect, the drug load is about 25%. In one aspect, the drug load is about 30%. In one aspect, the drug load is about 33%. In one aspect, the drug load is about 35%. In one aspect, the drug load is about 40%. In one aspect, the drug load is about 50%. In one aspect, the drug load is about 60%. In one aspect, the drug load is about 17%. In one aspect, the drug load is about 15%. In one aspect, the drug load is about 12%. In one embodiment, the drug load is about 50%.

In one embodiment, the active pharmaceutical ingredient is oxycodone, hydrocodone or codeine, or a salt, ether, ester, variant, or derivative thereof. In one embodiment, the active pharmaceutical ingredient is oxycodone. In another embodiment, the active pharmaceutical ingredient is hydrocodone. See Prescribing Information for OxyContin® ER 04/2014 (Purdue Pharma LP; available at www.purduepharma.com) and Zohydro® ER 01/2015 (Zogenix® Inc.; available at: www.zogenix.com), which are incorporated by reference herein for such teachings.

In another embodiment, the active pharmaceutical ingredient may comprise oxycodone, hydrocodone, or codeine and an additional active pharmaceutical ingredient. In one aspect, the additional active pharmaceutical ingredient prevents opioid abuse when an excess of opioid is used. In another aspect, the additional active pharmaceutical ingredient reduces or prevents opioid induced side effects.

In one embodiment, the abuse deterrent oral composition described herein comprises a dose of hydrocodone. In one aspect, the dose of hydrocodone is about 5 mg. In one aspect, the dose of hydrocodone is about 10 mg. In one aspect, the dose of hydrocodone is about 20 mg. In another aspect, the dose of hydrocodone is about 30 mg. In another aspect, the dose of hydrocodone is about 40 mg. In another aspect, the dose of hydrocodone is about 50 mg. In another aspect, the dose of hydrocodone is about 60 mg. In another aspect, the dose of hydrocodone is about 70 mg. In another aspect, the dose of hydrocodone is about 80 mg. In another aspect, the dose of hydrocodone is about 90 mg. In another aspect, the dose of hydrocodone is about 100 mg. In another aspect, the dose of hydrocodone is about 120 mg. In another aspect, the dose of hydrocodone is about 140 mg. In another aspect, the dose of hydrocodone is about 160 mg. In another aspect, the dose of hydrocodone is about 180 mg. In another aspect, the dose of hydrocodone is about 200 mg.

In one embodiment, the abuse deterrent oral composition described herein comprises a dose of oxycodone. In one aspect, the dose of oxycodone is about 5 mg. In another aspect, the dose of oxycodone is about 10 mg. In another aspect, the dose of oxycodone is about 15 mg. In another aspect, the dose of oxycodone is about 20 mg. In another aspect, the dose of oxycodone is about 30 mg. In another aspect, the dose of oxycodone is about 40 mg. In another aspect, the dose of oxycodone is about 50 mg. In another aspect, the dose of oxycodone is about 60 mg. In another aspect, the dose of oxycodone is about 70 mg. In another aspect, the dose of oxycodone is about 80 mg. In another aspect, the dose of oxycodone is about 100 mg. In another aspect, the dose of oxycodone is about 120 mg. In another aspect, the dose of oxycodone is about 140 mg. In another aspect, the dose of oxycodone is about 160 mg. In another aspect, the dose of oxycodone is about 180 mg. In another aspect, the dose of oxycodone is about 200 mg.

In another embodiment, the total dosage of oxycodone or hydrocodone administered in a 24-hour period is about 20 mg to about 600 mg per 24-hour period. In one aspect, the total dosage of oxycodone or hydrocodone administered in a 24-hour period is about 50 mg to about 250 mg per 24-hour period. The dosage can contain a total amount of oxycodone or hydrocodone effective for treatment, amelioration, prophylaxis, or reducing the onset of or symptoms of pain.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of hydrocodone is 10 mg to about 40 mg. In one aspect, an initial dose of about 10 mg to about 40 mg is suitable for a subject that not tolerant of an opioid. In one aspect, the initial dose is about 10 mg of hydrocodone. In another aspect, the initial dose is about 20 mg of hydrocodone. In another aspect, the initial dose is about 20 mg of hydrocodone. In another aspect, the initial dose is about 30 mg of hydrocodone. In another aspect, the initial dose is about 40 mg of hydrocodone. In another aspect, the dose of hydrocodone may be maintained and given every 8 to 12 hours. In another aspect, the dose of hydrocodone may be increased by about 10 mg to about 20 mg every 8 hrs to 12 hrs until relief of a painful condition or the perception of pain occurs.

In another embodiment, the initial dosage of hydrocodone is 40 mg to about 80 mg. In one aspect, an initial dose of about 40 mg to about 80 mg is suitable for a subject that has an opioid tolerant phenotype. In one aspect, the initial dose is about 40 mg of hydrocodone. In another aspect, the initial dose is about 50 mg of hydrocodone. In another aspect, the initial dose is about 60 mg of hydrocodone. In another aspect, the initial dose is about 70 mg of hydrocodone. In another aspect, the initial dose is about 80 mg of hydrocodone. In another aspect, the dose of hydrocodone may be maintained and given every 8 to 12 hours. In another aspect, the dose of hydrocodone may be increased by about 10 mg to about 20 mg every 8 hrs to 12 hrs until relief of a painful condition or the perception of pain occurs.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of oxycodone is 10 mg to about 40 mg. In one aspect, an initial dose of about 10 mg to about 40 mg is suitable for a subject that not tolerant of an opioid and a dose. In one aspect, the initial dose is about 10 mg of oxycodone. In another aspect, the initial dose is about 20 mg of oxycodone. In another aspect, the initial dose is about 20 mg of oxycodone. In another aspect, the initial dose is about 30 mg of oxycodone. In another aspect, the initial dose is about 40 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until relief of a painful condition or the perception of pain occurs.

In another embodiment, the initial dosage of oxycodone is 40 mg to about 160 mg. In one aspect, an initial dose of about 40 mg to about 80 mg is suitable for a subject that has an opioid tolerant phenotype. In one aspect, the initial dose is about 40 mg of oxycodone. In another aspect, the initial dose is about 50 mg of oxycodone. In another aspect, the initial dose is about 60 mg of oxycodone. In another aspect, the initial dose is about 70 mg of oxycodone. In another aspect, the initial dose is about 80 mg of oxycodone. In another aspect, the initial dose is about 100 mg of oxycodone. In another aspect, the initial dose is about 120 mg of oxycodone. In another aspect, the initial dose is about 140 mg of oxycodone. In another aspect, the initial dose is about 160 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until relief of a painful condition or the perception of pain occurs.

Additional pain that the abuse deterrent pharmaceutical composition described herein may be useful for the treatment of pain stemming from including, but not limited to, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica, or granuloma annulare.

In another embodiment, the abuse deterrent pharmaceutical composition comprising an abuse deterrent composition as described herein reduces the dissolution and extraction of an active pharmaceutical ingredient. Suitable non-limiting examples of extraction methods comprise incubating the abuse deterrent pharmaceutical composition in boiling conditions, in aqueous solutions of alcohol, and in distilled water. These methods may be used in conjunction with additional means of agitating, for example, with paddles, dipping, vigourous shaking, physical manipulations, and the like.

Another embodiment described herein is an abuse deterrent pharmaceutical composition as described herein comprising a therapeutically effective amount of one or more active pharmaceutical ingredients for administration to a subject having pain, exhibiting an in vitro dissolution rate as described herein in any one of FIGS. 3-17.

Another embodiment described herein is a method for orally administering a dosage form of an abuse deterrent pharmaceutical composition comprising an active pharmaceutical ingredient described herein for the treatment, amelioration, prophylaxis, or reducing the onset of or symptoms of pain.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, exhibiting an in vitro dissolution rate as described herein in any one of FIGS. 3-17.

Another embodiment described herein is a method for treating an individual having pain, with a pharmaceutical composition described herein comprising an abuse deterrent composition described herein comprising a dosage of about 10 mg of oxycodone to about 80 mg of oxycodone, wherein subjects administered a single dosage exhibit a mean plasma oxycodone $C_{max}$ of about 10 ng/mL to about 150 ng/mL, including each integer within the specified range. In one aspect, the composition is provided in a dosage form containing a total amount of about 10 mg of oxycodone, wherein subjects administered a single dosage exhibit a mean plasma oxycodone $C_{max}$ of about 10 ng/mL. In another aspect, the composition is provided in a dosage form containing a total amount of about 20 mg of oxycodone, wherein subjects administered a single dosage exhibit a mean plasma oxycodone $C_{max}$ of about 20 ng/mL. In another aspect, the composition is provided in a dosage form containing a total amount of about 40 mg of oxycodone, wherein subjects administered a single dosage exhibit a mean plasma oxycodone $C_{max}$ of about 40 ng/mL. In another aspect, the composition is provided in a dosage form containing a total amount of about 80 mg of oxycodone, wherein subjects administered a single dosage exhibit a mean plasma oxycodone $C_{max}$ of about 100 ng/mL.

Another embodiment described herein is a method for treating an individual having pain, with a pharmaceutical composition described herein comprising an abuse deterrent composition described herein comprising a dosage of about 10 mg of oxycodone to about 80 mg of oxycodone, wherein subjects administered a single dosage exhibit a mean plasma oxycodone $AUC_{0\to\infty}$ of about 100 h·mg/L to about 1000 h·mg/L, including each integer within the specified range. In one aspect, the composition is provided in a dosage form containing a total amount of about 10 mg of oxycodone, wherein subjects administered a single dosage exhibit a mean plasma oxycodone $AUC_{0\to\infty}$ of about 100 h·mg/L. In another aspect, the composition is provided in a dosage form containing a total amount of about 20 mg of oxycodone, wherein subjects administered a single dosage exhibit a mean plasma oxycodone $AUC_{0\to\infty}$ of about 200 h·mg/L. In another aspect, the composition is provided in a dosage form containing a total amount of about 40 mg of oxycodone, wherein subjects administered a single dosage exhibit a mean plasma oxycodone $AUC_{0\to\infty}$ of about 400 h·mg/L. In another aspect, the composition is provided in a dosage form containing a total amount of about 80 mg of oxycodone, wherein subjects administered a single dosage exhibit a mean plasma oxycodone $AUC_{0\to\infty}$ of about 1000 h·mg/L.

Another embodiment described herein is a method for treating an individual having pain, with a pharmaceutical composition described herein comprising an abuse deterrent composition described herein comprising a dosage of about 10 mg of oxycodone to about 80 mg of oxycodone, wherein subjects administered a single dosage exhibits a $T_{max}$ of about 1 hr to about 8 hrs, including each integer within the specified range. In one aspect, the composition is provided in a dosage form containing a total amount of about 10 mg to about 80 mg of oxycodone, wherein subjects administered a single dosage exhibit a $T_{max}$ of about 1 hr, about 1.5 hrs, about 2 hrs, about 2.5 hrs, about 3 hrs, about 3.5 hrs, about 4 hrs, 4.5 hrs, 5 hrs, 5.5 hrs, 6 hrs, 6.5 hrs, 7 hrs, 7.5 hrs, or about 8 hrs.

Another embodiment described herein is a method for treating an individual having pain, with a pharmaceutical composition described herein comprising an abuse deterrent composition described herein comprising a dosage of about 10 mg of hydrocodone to about 80 mg of hydrocodone, wherein subjects administered a single dosage exhibit a mean plasma hydrocodone $C_{max}$ of about 10 ng/mL to about 120 ng/mL, including each integer within the specified range. In one aspect, the composition is provided in a dosage form containing a total amount of about 10 mg of a hydrocodone, wherein subjects administered a single dosage exhibit a mean plasma hydrocodone $C_{max}$ of about 20 ng/mL. In another aspect, the composition is provided in a dosage form containing a total amount of about 20 mg of hydrocodone, wherein subjects administered a single dosage exhibit a mean plasma hydrocodone $C_{max}$ of about 30 ng/mL. In another aspect, the composition is provided in a dosage form containing a total amount of about 30 mg of hydrocodone, wherein subjects administered a single dosage exhibit a mean plasma hydrocodone $C_{max}$ of about 40 ng/mL. In another aspect, the composition is provided in a dosage form containing a total amount of about 40 mg of hydrocodone, wherein subjects administered a single dosage exhibit a mean plasma hydrocodone $C_{max}$ of about 60 ng/mL. In another aspect, the composition is provided in a dosage form containing a total amount of about 80 mg of hydrocodone, wherein subjects administered a single dosage exhibit a mean plasma hydrocodone $C_{max}$ of about 120 ng/mL.

Another embodiment described herein is a method for treating an individual having pain, with a pharmaceutical composition described herein comprising an abuse deterrent composition described herein comprising a dosage of about 10 mg of hydrocodone to about 80 mg of hydrocodone, wherein subjects administered a single dosage exhibit a mean plasma hydrocodone $AUC_{0\to\infty}$ of about 100 h·mg/L to about 1600 h·mg/L, including each integer within the specified range. In one aspect, the composition is provided in a dosage form containing a total amount of about 10 mg of a hydrocodone, wherein subjects administered a single dosage exhibit a mean plasma hydrocodone $AUC_{0\to\infty}$ of about 150 h·mg/L. In another aspect, the composition is provided in a dosage form containing a total amount of about 20 mg of hydrocodone, wherein subjects administered a single dosage exhibit a mean plasma hydrocodone $AUC_{0\to\infty}$ of about 400 h·mg/L. In another aspect, the composition is provided in a dosage form containing a total amount of about 40 mg of hydrocodone, wherein subjects administered a single dosage exhibit a mean plasma hydrocodone $AUC_{0\to\infty}$ of about 850 h·mg/L. In another aspect, the composition is provided in a dosage form containing a total amount of about 80 mg of hydrocodone, wherein subjects administered a single dosage exhibit a mean plasma hydrocodone $AUC_{0\to\infty}$ of about 1600 h·mg/L.

Another embodiment described herein is a method for treating an individual having pain, with a pharmaceutical composition described herein comprising an abuse deterrent composition described herein comprising a dosage of about 10 mg of hydrocodone to about 80 mg of hydrocodone, wherein subjects administered a single dosage exhibits a $T_{max}$ of about 3 hrs to about 8 hrs, including each integer within the specified range. In one aspect, the composition is provided in a dosage form containing a total amount of about 10 mg to about 80 mg of hydrocodone, wherein subjects administered a single dosage exhibit a $T_{max}$ of about 3 hrs, about 4 hrs, about 5 hrs, about 6 hrs, about 7 hrs, or about 8 hrs.

In another embodiment, the pharmaceutical compositions described herein further comprise one or more active pharmaceutical ingredient(s) suitable for treating, ameliorating, or prophylactically treating a bowel dysfunction due to acute or chronic opioid use, often referred to as opioid induced bowel disfunction (OIBD). Symptoms of OIBD typically comprise constipation (e.g., opioid induced constipation; OIC), anorexia, nausea and vomiting, gastro-oesophageal reflux, delayed digestion, abdominal pain, flatulence, bloating, hard stools, incomplete evacuation or straining during bowel movements. Alternative or additional uses for the one or more active pharmaceutical ingredient(s) described herein may be to treat, reduce, inhibit, or prevent additional effects of acute or chronic opioid use including, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Additional advantageous uses of one or more active pharmaceutical ingredient(s) include treatment of opioid-induced immune suppression, inhibition of angiogenesis, inhibition of vascular proliferation, treatment of pain, treatment of inflammatory conditions such as inflammatory bowel syndrome, treatment of infectious diseases and diseases of the musculoskeletal system such as osteoporosis, arthritis, osteitis, periostitis, myopathies, and treatment of autoimmune diseases, terminally ill patients receiving opioid therapy such as an AIDS patient, a cancer patient, a cardiovascular patient; subjects receiving opioid therapy for maintenance of opioid withdrawal. In one aspect, the subject is a subject using an opioid for chronic pain management. In another aspect, the subject is a subject using an acutely using an opioid for temporary pain management. In another aspect, the subject is a terminally ill patient. In another aspect, the subject is a person receiving opioid withdrawal maintenance therapy.

In another embodiment, suitable active pharmaceutical ingredients for treating a symptom or condition of opioid use may comprise a laxative such as lubiprostone, linaclotide, lactulose, and a heavy molecular weight poly ethylene glycol (e.g., PEG 3350; Miralax®; GlycoLax), sorbitol, calcium carbonate, potassium phosphate, magnesium hydroxide, psyllium, glycerin, polycarbophil, or docusate, or a mixture or combination thereof. In some aspects, other suitable pharmaceutical ingredients may comprise a natural therapeutic or nutraceutical comprising barberry, cascara sagrada, flax, or senna or a mixture or combination thereof. In some further aspects, suitable active pharmaceutical ingredients for the treatment, amelioration, or prophylaxis of OIBD or OIC comprise a peripherally acting mu-opioid receptor antagonist (PAMORA). In some aspects, the PAMORA comprises methylnaltrexone, naltrexone, naloxone, naloxegol, or alvimopan, or a mixture or combination thereof.

It is understood that activation of mu-opiod receptors along the gastro intestinal tract are responsible for decreased bowel function and constipation. Thus, without being bound by any theory, PAMORAs are useful for preventing symptoms of OIBD, and specifically OIC, by inhibiting the action of the mu-opioid receptor peripherally along the gastrointestinal tract without inhibiting the mu-opiod receptors of the central nervous system (CNS). Therefore, a combination of an opioid agonist (e.g., oxycodone or hydrocodone) activates the CNS receptors and the co-administration of a PAMORA inhibits the peripheral gut mu-opioid receptors, which are believed to be responsible for the incurrence of OIC.

In one embodiment, the pharmaceutical compositions described herein comprise a dose of an opioid (e.g., oxycodone or hydrocodone) and a dose of a PAMORA. In one aspect, the pharmaceutical compositions described herein comprise a dose of an opioid and a dose of a PAMORA comprising naloxone or a pharmaceutically acceptable salt form thereof. In one aspect, the pharmaceutical compositions described herein comprise a dose of an opioid and a dose of a PAMORA comprising naltrexone or a pharmaceutically acceptable salt form thereof. In another aspect, the pharmaceutical compositions described herein comprise a dose of an opioid and a dose of a PAMORA comprising methylnaltrexone or a pharmaceutically acceptable salt form thereof. In another aspect, the pharmaceutical compositions described herein comprise a dose of an opioid and a dose of a PAMORA comprising naloxegol or a pharmaceutically acceptable salt form thereof.

In one embodiment, the pharmaceutical composition described herein comprises a dose of a PAMORA (e.g., naloxegol, naloxone, methylnaltrexone, or naltrexone) and a dose of an opioid (e.g., hydrocodone or oxycodone). In one aspect, the dose of the PAMORA ranges from about 50 mg to about 600 mg and the dose of the opioid is from about 5 mg to about 150 mg, including every integer within the specified ranges. In another aspect, the dose of the PAMORA ranges from about 50 mg to about 550 mg and the dose of the opioid is from about 5 mg to about 150 mg, including every integer within the specified ranges. In another aspect, the dose of the PAMORA ranges from about 5 mg to about 50 mg and the dose of the opioid is from about 5 mg to about 100 mg, including every integer within the specified ranges.

In another embodiment, the weight percentage ratio range of PAMORA (e.g., naloxegol, naloxone, methylnaltrexone, or naltrexone) to opioid (e.g., hydrocodone or oxycodone) in the pharmaceutical composition described herein ranges from about 15:1 to about 1:18, including each ratio within the specified range. In one aspect, the weight percentage ratio range of PAMORA (e.g., naloxegol, naloxone, methylnaltrexone, or naltrexone) to opioid is from about 13:1 to about 1:1, including each ratio within the specified range. In another aspect, the weight percentage ratio range of PAMORA (e.g., naloxegol, naloxone, methylnaltrexone, or naltrexone) to opioid is from about 1:16 to about 1:1, including each ratio within the specified range. In another aspect, the weight percentage ratio range of PAMORA to opioid is about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, or about 15:1.

In one embodiment, the pharmaceutical composition described herein comprises a dose of naloxone and a dose of an opioid comprising hydrocodone or oxycodone as described herein. In one aspect, the dose of the naloxone ranges from about 2.5 mg to about 100 mg, including each integer within the specified range. In another aspect, the dose of naloxone ranges from about 2.5 mg to about 50 mg, including each integer within the specified range. In another aspect, the dose of naloxone ranges from about 10 mg to about 50 mg, including each integer within the specified range. In another aspect, the dose of naloxone ranges from about 20 mg to about 40 mg, including each integer within the specified range. In another aspect, the dose of naloxone is about 2.5 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In another embodiment, the weight percentage ratio range of naloxone to opioid comprising hydrocodone or oxycodone in the pharmaceutical composition described herein ranges from about 1:10 to about 5:1, including all iterations of ratios within the specified range. In one aspect, the weight percentage ratio range of naloxone to opioid comprising hydrocodone or oxycodone is from about 1:5 to about 1:1, including all iterations of ratios within the specified range. In another aspect, the weight percentage ratio range of naloxone to opioid comprising hydrocodone or oxycodone is from about 1:4 to about 1:2, including all iterations of ratios within the specified range. In another aspect, the weight percentage ratio range of naloxone to opioid comprising hydrocodone or oxycodone is about 1:10, about 1:9, about 1:8, about 1:7, about 1:6, about 1:5, about 1:4, about 1:3, about 1:2, about 1:1, about 2:1, about 3:1, about 4:1, or about 5:1. In another aspect, the weight percentage ratio range of naloxone to opioid comprising hydrocodone or oxycodone is about 1:2.

In another embodiment, the pharmaceutical composition described herein comprises a dose of about 5 mg of naloxone and a dose of about 10 mg of oxycodone. In another embodiment, the pharmaceutical composition described herein comprises a dose of about 10 mg of naloxone and a dose of about 20 mg of oxycodone. In another embodiment, the pharmaceutical composition described herein comprises a dose of about 20 mg of naloxone and a dose of about 40 mg of oxycodone. In another embodiment, the pharmaceutical composition described herein comprises a dose of about 40 mg of naloxone and a dose of about 80 mg of oxycodone. In another embodiment, the pharmaceutical composition described herein comprises a dose of about 80 mg of naloxone and a dose of about 160 mg of oxycodone.

In another embodiment, the pharmaceutical composition described herein comprises a dose of about 5 mg of naloxone and a dose of about 10 mg of hydrocodone. In another embodiment, the pharmaceutical composition described herein comprises a dose of about 10 mg of naloxone and a dose of about 20 mg of hydrocodone. In another embodiment, the pharmaceutical composition described herein comprises a dose of about 20 mg of naloxone and a dose of about 40 mg of hydrocodone. In another embodiment, the pharmaceutical composition described herein comprises a dose of about 40 mg of naloxone and a dose of about 80 mg of hydrocodone. In another embodiment, the pharmaceutical composition described herein comprises a dose of about 80 mg of naloxone and a dose of about 160 mg of hydrocodone.

In another embodiment, the pharmaceutical composition described herein comprises a dose of about 40 mg of oxycodone and a dose of about 20 mg of naloxone. In one aspect, the composition is provided in a dosage form containing a total amount of about 40 mg of oxycodone and about 20 mg of naloxone, wherein subjects administered a single dosage exhibit a mean plasma oxycodone $AUC_{0\to\infty}$ of about 400 h·mg/L to about 600 h·mg/L and a mean plasma naloxone $AUC_{0\to\infty}$ of about 500 h·mg/L to about 600 h·mg/L. In another aspect, the composition is provided in a dosage form containing a total amount of about 40 mg of oxycodone and about 20 mg of naloxone, wherein subjects administered a single dosage exhibit a mean plasma oxycodone $C_{max}$ of about 30 ng/mL to about 50 ng/mL and a mean plasma naloxone $C_{max}$ of about 50 ng/mL to about 70 ng/mL. In another aspect, the composition is provided in a dosage form containing a total amount of about 40 mg of oxycodone and about 20 mg of naloxone, wherein subjects administered a single dosage exhibit an oxycodone $T_{max}$ of about 1 hr to about 5 hrs and a naloxone $T_{max}$ of about 0.5 hr to about 3 hrs.

In one embodiment, the pharmaceutical composition described herein comprises a dose of methylnaltrexone or naltrexone and a dose of an opioid comprising hydrocodone or oxycodone as described herein. In one aspect, the dose of the methylnaltrexone or naltrexone ranges from about 2.5 mg to about 100 mg, including each integer within the specified range. In another aspect, the dose of methylnaltrexone or naltrexone ranges from about 50 mg to about 600 mg, including each integer within the specified range. In another aspect, the dose of methylnaltrexone or naltrexone ranges from about 100 mg to about 600 mg, including each integer within the specified range. In another aspect, the dose of methylnaltrexone or naltrexone ranges from about 300 mg to about 600 mg, including each integer within the specified range. In another aspect, the dose of methylnaltrexone or naltrexone ranges from about 400 mg to about 600 mg, including each integer within the specified range. In another aspect, the dose of methylnaltrexone or naltrexone is about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, or about 550 mg.

In another embodiment, the weight percentage ratio range of methylnaltrexone or naltrexone to opioid comprising hydrocodone or oxycodone in the pharmaceutical composition described herein ranges from about 13:1 to about 1:1, including all iterations of ratios within the specified range. In one aspect, the weight percentage ratio range of methylnaltrexone or naltrexone to opioid comprising hydrocodone or oxycodone is from about 10:1 to about 1:1, including all iterations of ratios within the specified range. In another aspect, the weight percentage ratio range of methylnaltrexone or naltrexone to opioid comprising hydrocodone or oxycodone is from about 5:1 to about 1:1, including all iterations of ratios within the specified range. In another aspect, the weight percentage ratio range of methylnaltrexone or naltrexone to opioid comprising hydrocodone or oxycodone is about 1:1, about 2:1, about 3:1, about 4:1, about 5:1, about 6:1, about 7:1, about 8:1, about 9:1, about 10:1, about 11:1, about 12:1, or about 13:1.

In one embodiment, the pharmaceutical composition described herein comprises a dose of naloxegol and a dose of an opioid comprising hydrocodone or oxycodone as described herein. In one aspect, the dose of the naloxegol ranges from about 2.5 mg to about 100 mg, including each integer within the specified range. In another aspect, the dose of naloxegol ranges from about 2.5 mg to about 50 mg, including each integer within the specified range. In another aspect, the dose of naloxegol ranges from about 10 mg to about 50 mg, including each integer within the specified range. In another aspect, the dose of naloxegol ranges from about 20 mg to about 40 mg, including each integer within the specified range. In another aspect, the dose of naloxegol is about 2.5 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In another embodiment, the weight percentage ratio range of naloxegol to opioid comprising hydrocodone or oxycodone in the pharmaceutical composition described herein ranges from about 1:10 to about 5:1, including all iterations of ratios within the specified range. In one aspect, the weight percentage ratio range of naloxegol to opioid comprising hydrocodone or oxycodone is from about 1:5 to about 1:1, including all iterations of ratios within the specified range. In another aspect, the weight percentage ratio range of naloxegol to opioid comprising hydrocodone or oxycodone is from about 1:4 to about 1:2, including all iterations of ratios within the specified range. In another aspect, the weight percentage ratio range of naloxegol to opioid comprising hydrocodone or oxycodone is about 1:10, about 1:9, about 1:8, about 1:7, about 1:6, about 1:5, about 1:4, about 1:3, about 1:2, about 1:1, about 2:1, about 3:1, about 4:1, or about 5:1. In another aspect, the weight percentage ratio range of naloxegol to opioid comprising hydrocodone or oxycodone is about 1:2.

Another embodiment described herein is a method for treating, retarding the progression of, prophylaxis of, delaying the onset of, ameliorating, or reducing the symptoms of pain comprising the administration of a therapeutically effective amount of one or more abuse deterrent pharmaceutical compositions described herein to a subject with pain, wherein the administration is sufficient to achieve a reduction pain relative to baseline in the subject without substantially inducing one or more side effects including, but not limited to, headache, vertigo, somnolence, nausea, constipation, vomiting, xerostomia, fatigue, pruritus, eructation, heartburn, abdominal discomfort, or loss of appetite.

Another embodiment described herein is a method for treating, retarding the progression of, prophylaxis of, delaying the onset of, ameliorating, or reducing the symptoms of pain comprising the administration of a therapeutically effective amount of one or more abuse deterrent pharmaceutical compositions described herein to a subject with pain, wherein the administration is sufficient to achieve a reduction pain relative to baseline in the subject without substantially inducing one or more side effects including, but not limited to, opioid use, such as, for example, opioid induced bowel dysfunction, opioid induced constipation, gastrointestinal dysfunction (e.g., inhibition of intestinal motility, constipation, GI sphincter constriction), nausea, emesis (vomiting), biliary spasm, colic, dysphoria, pruritus, urinary retention, depression of respiration, papillary constriction, cardiovascular effects, chest wall rigidity and cough suppression, depression of stress response, and immune suppression associated with use of narcotic analgesia, etc, or combinations thereof.

Another embodiment described herein is a method for treating, retarding the progression of, prophylaxis of, delaying the onset of, ameliorating, or reducing the symptoms of, irritable bowel syndrome, colitis, post-operative or postpartum ileus, nausea and/or vomiting, decreased gastric motility and emptying, inhibition of the stomach, and small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, idiopathic constipation, post-operative gastrointestinal dysfunction following abdominal surgery (e.g., colectomy (e.g., right hemicolectomy, left hemicolectomy, transverse hemicolectomy, colectomy takedown, low anterior resection)), and delayed absorption of orally administered medications or nutritive substances comprising the administration of a therapeutically effective amount of one or more abuse deterrent pharmaceutical compositions described herein.

Another embodiment described herein is a method for improving the quality of life of subjects receiving opioids, as well as to reduce complications arising from chronic constipation, such as hemorrhoids, appetite suppression, mucosal breakdown, sepsis, colon cancer risk, and myocardial infarction comprising the administration of a therapeutically effective amount of one or more abuse deterrent pharmaceutical compositions described herein.

In another embodiment, the pharmaceutical composition described herein provides for a dosage form, which comprises an opioid and a PAMORA as described in, which in terms of efficacy, is ranked good or very good by more than 50% of patients, 60%, 70%, 80%, 90% or more of patients. In aspect, the dosage form is provided which comprises an opioid and a PAMORA as described in, which in terms of tolerability, is ranked good or very good by more than 50% of patients, 60%, 70%, 80%, 90% or more of patients.

In another embodiment, the pharmaceutical composition described herein provides for a dosage form, which comprises an opioid and a PAMORA as described in, which provides a reduction of days with laxative intake by at least 10%, 20%, 30%, 40%, 50%, 60%, 70%, 80%, or even 90%. In one aspect, the dosage form completely reduces the need for laxative to be taken independently.

In some embodiments, bowel function is assessed by observing parameters that are associated with bowel function. In particular, bowel function may be determined based on parameters selected from ease or difficulty of defecation, feeling of incomplete bowel evacuation, and/or personal judgment of patient regarding constipation. Other parameters which may be observed alternatively or in addition in order to assess the bowel function of a patient include among other things stool frequency, stool consistency, cramping, and painful laxation. Bowel function may be assessed by measuring parameters, which are associated with bowel function using numerical analog scales (NAS) for these parameters because this may provide more accurate results. This approach is particularly advantageous when assessing the bowel function in patients receiving treatment with analgesics, because analgesic efficacy of drugs is usually assessed using a numeric analog scale.

In some embodiments, a pharmaceutical composition is provided comprising an opioid and PAMORA as described herein to provide an improvement of the bowel function characterized by an improvement of the mean bowel function score of at least 5, at least about 8, at least about 10 or at least about 15 after administration at steady state or of a single dose to human patients or healthy human subjects, wherein the mean bowel function score is measured with a numerical analog scale ranging from 0 to 100.

In one embodiment, the bowel function is assessed by the bowel function index (BFI), which is measured in patients. The mean bowel function score may be determined by a method for assessing bowel function in a patient comprising the steps of: providing the patient with a numeric analog scale for at least one parameter, which parameter is associated with bowel function; causing the patient to indicate on the numeric analog scale the amount and/or intensity of the parameter being experienced; and observing the amount and/or intensity of the at least one parameter indicated on the numeric analog scale in order to assess bowel function. In one aspect the patient indicates the amount and/or intensity of parameter being experienced during the last days or weeks, e.g. during the last 1, 2, 3, 4, 5, 6, 7, 10, or 14 days. In another aspect, the numerical analog scale on which the patient indicates his/her subjective experience of the observed parameter may have any size or form and may range from 0 or any other number to any number, such as from 0 to 10 or from 0 to 50 or from 0 to 300 or from 1 to 10.

In another embodiment, if more than one parameter is observed, a mean bowel function may be obtained in form of a numerical value. This numerical value is the mean of the parameters observed, e.g., the three numeric analog scale values for ease or difficulty of defecation, feeling of incomplete bowel evacuation and judgment of constipation. The parameters, which are measures of bowel function or which are associated with bowel function, may comprise opioid induced bowel dysfunctions (OIBD or OIC) as described herein.

In another embodiment, bowel function may be determined based on the following parameters: ease or difficulty of defecation, for example during the last 7 days according to the patient assessment, wherein 0 corresponds to no difficulties and 100 corresponds to severe difficulties; feeling of incomplete bowel evacuation, for example during the last 7 days according to the patient assessment, wherein 0 corresponds to no feeling of incomplete bowel evacuation and 100 corresponds to very strong feeling of incomplete bowel evacuation; personal judgment of patient regarding constipation, for example during the last 7 days, wherein 0 corresponds to no constipation at all and 100 corresponds to very heavy constipation.

In another embodiment, bowel function may be assessed with analogs scales as described in U.S. Pat. No. 6,258,042 and International Patent Application Publication No. WO 2003/073937, which may be adapted to devices or analog scales as described above as would be understood by one of ordinary skill in the art. The disclosures of these two references are hereby incorporated by reference for such teachings.

In another embodiment, the pharmaceutical compositions described herein further comprise one or more active pharmaceutical ingredient(s), which prevent drug abuse by inhibiting the action or effects of an opioid. In one aspect, the pharmaceutical composition comprises an opioid (e.g., hydrocodone or oxycodone) and one or more abuse deterrent aversive agents. The abuse deterrent aversive agent may be any one of a laxative such as lubiprostone, linaclotide, lactulose, and a heavy molecular weight poly ethylene glycol (e.g., PEG 3350; Miralax®; GlycoLax), sorbitol, calcium carbonate, potassium phosphate, magnesium hydroxide, psyllium, glycerin, polycarbophil, or docusate, or a mixture or combination thereof. Further abuse deterrent aversive agents may comprise methylnaltrexone, naltrexone, naloxone, naloxegol, or alvimopan, or a mixture or combination thereof. The aversive effect of the abuse deterrent aversive agent may include any unpleasant side effect comprising inducing opioid withdrawl symptoms, diarrhea, nausea, reduced euphoria or a mixture or combination thereof.

In another embodiment, the abuse deterrent pharmaceutical composition described herein is contained and dispensed from a tamper evident packaging. The term "tamper evident" or "tamper resistant" refers to a packaging of any kind that readily displays or allows for an individual to observe any physical interference or manipulation of the packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain appropriate instructions for prescribing, instructions for use, contraindications, warnings, or other appropriate information.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof

EXAMPLES

Example 1

Figure 2:
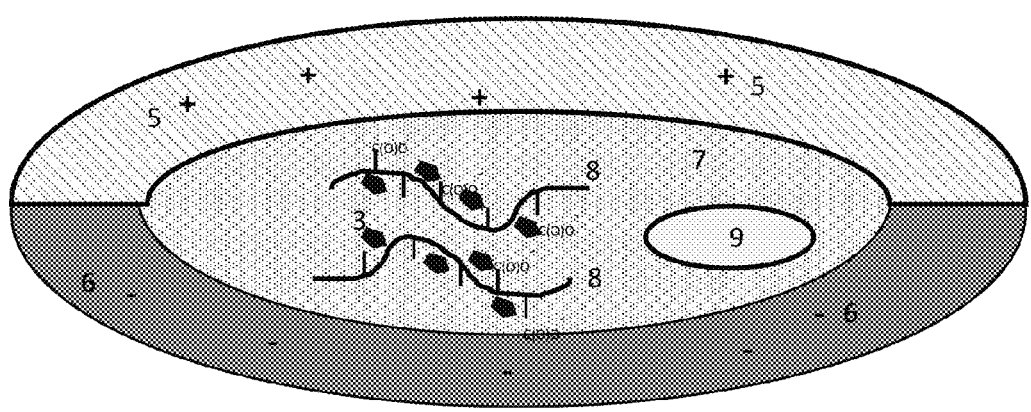
FIG. 2. Illustration of an exemplary anti-overingestion pharmaceutical composition.

Pharmaceutical compositions as described herein for preventing the over ingestion of active pharmaceutical ingredients are illustrated in FIGS. 1 and 2.

FIG. 1 represents the anti-over ingestion properties of the pharmaceutical compositions described herein. As shown, when one capsule (2) is ingested into the stomach (1) a controlled release (e.g., an immediate release) of all of the one or more active pharmaceutical ingredients (3) occurs. However, when multiple of the capsules (2) are ingested into the stomach (1), a clumping of the capsules (4) occurs, which inhibits the release of the one or more active pharmaceutical ingredients (3), effectively preventing over ingestion of the active pharmaceutical ingredient.

FIG. 2 is a pharmaceutical composition contemplated herein. In one embodiment described herein, the pharmaceutical composition may be a soft or hard capsule shell containing one or more multiple ionic polymers (5; 6) encapsulating one or more active pharmaceutical ingredients (3). In another embodiment described herein, the soft or hard capsule shell may not have any ionic polymers. As shown, a positive polymer (5) may be used in at least a portion of the soft capsule shell and a negative polymer (6) may be used in at least a portion of the soft capsule shell in those compositions containing multiple ionic polymers. The active pharmaceutical ingredient (3) (e.g., an abuse prone drug; oxycodone) may further be in a polyelectrolyte complex. In some aspects described herein, this polyelectrolyte complex is a cation or anion exchange complex, which further inhibits the release of the active pharmaceutical ingredient (3) when multiple dosage forms are dissolved in proximity of each other. The cation or anion exchange complex may comprise a positive cation or a negative anion exchanger. An exemplary positive cation exchanger polymer with carboxylic acid groups (8) is shown.

The pharmaceutical composition described herein may further comprise an abuse deterrent matrix (7), which prevents the crushing, grating, grinding, cutting, solvating, or dissolving of one or more active pharmaceutical ingredients. An additional means (9) for obtaining gastroretentive properties to the pharmaceutical composition may be included in the matrix fill or alternatively in the capsule shell (not illustrated). Exemplary and non-limiting means for gastroretentive properties known in the art may comprise one or more of an effervescent gas generating system, a colloidal gel barrier, porous beads, a microporous membrane, or the inclusion of one or more low-density excipients.

Example 2

Weak and strong cation exchange resins and a bound surrogate drug (dextromethorphan) were evaluated for use in an abuse deterrent composition. Biochemically similar opioids contemplated herein will demonstrate similar behaviors and release kinetics. The first resin used was strongly acidic and is based on polystyrene sulfonate (Amberlite™ IRP69)

and a weakly acidic resin that is based on carboxylic acid functional groups (Amberlite™ IRP88). Drug-resinates were prepared according to the following process: a solution of drug in deionized water was mixed with an ion-exchange resin. Typically, a 1:1 ratio of resin to drug was used. The resinate complex was then separated from the remaining solution by filtration or centrifugation and the resulting resinate was washed several times with DI water and dried in a vacuum. Several batches of resinates of dextromethorphan with Amberlite™ IRP88 or Amberlite™ IRP69 were prepared and encapsulated in a hard capsule.

The in vitro drug release from drug-resinates was assessed in simulated gastrointestinal fluid mediums and in medias having different pH values. The in vitro drug release from drug-resinates at pH: 1.5, 4.8 and 7.4 was assessed using the USP basket method (APP I) at 100 rpm in 900 mL of media. The drug release profile with either a drug load of 41 mg from Amberlite™ IRP69 and Amberlite™ IRP88 is shown in FIGS. 3 and 4, respectively.

Figure 3:
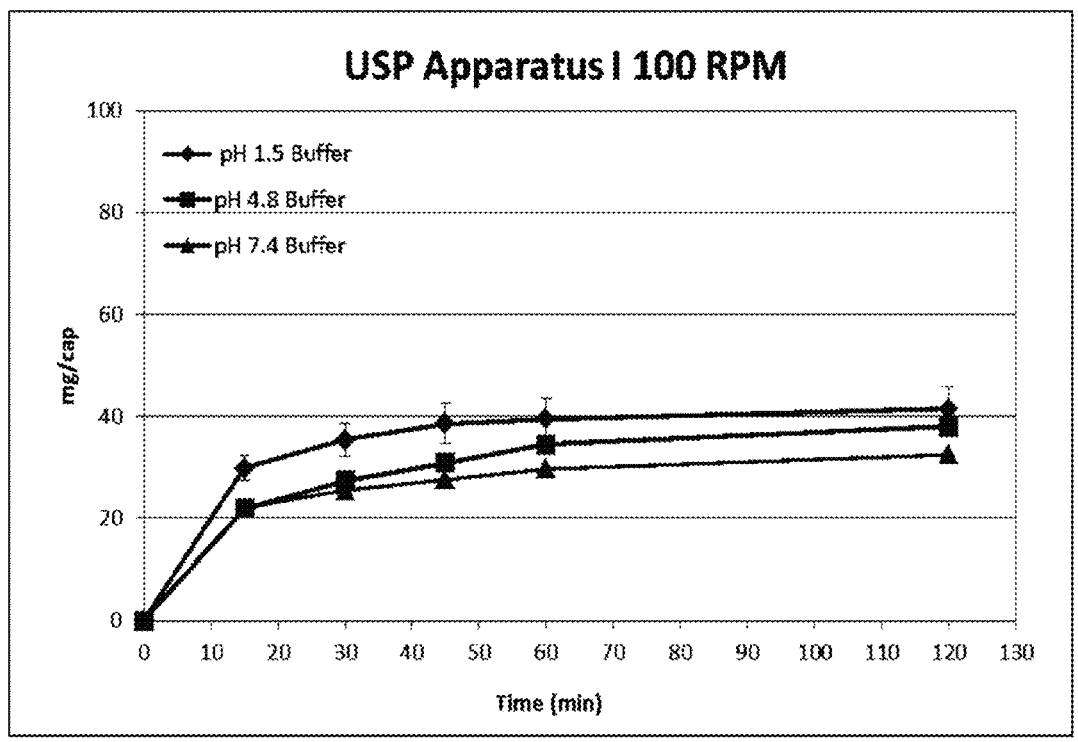
FIG. 3. In vitro drug release of an Amberlite™ IRP69-dextromethorphan drug resinate at pH 1.5, pH 4.8, and pH 7.4 buffers USP Apparatus I.
Figure 4:
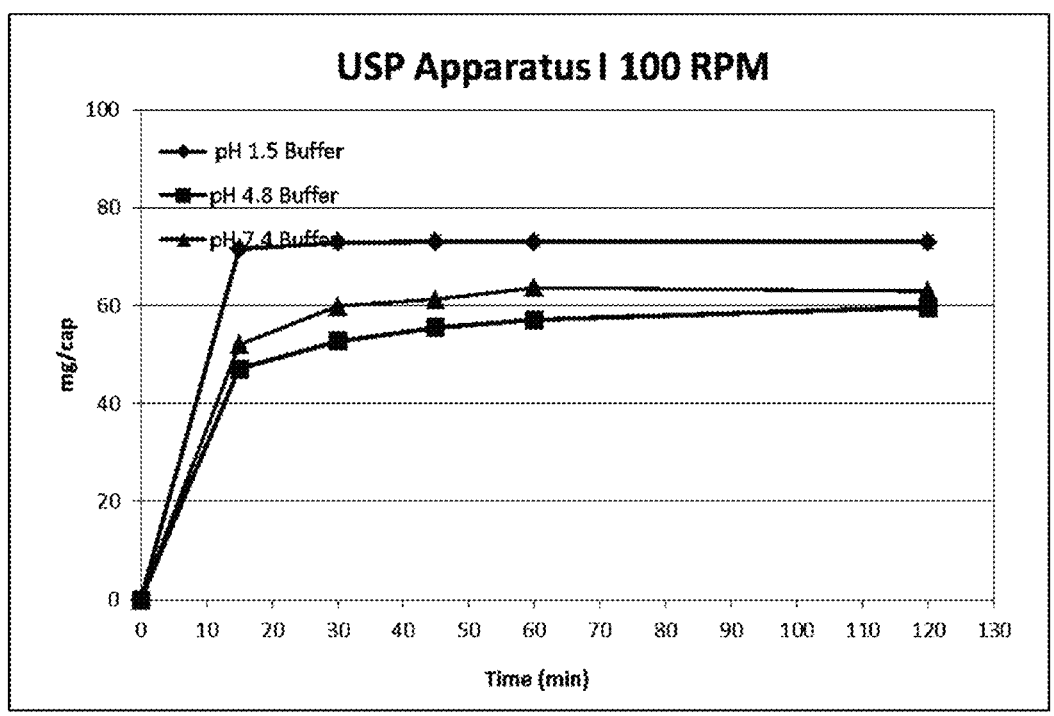
FIG. 4. In vitro drug release of an Amberlite™ IRP88-dextromethorphan drug resinate at pH 1.5, pH 4.8, and pH 7.4 buffers using USP Apparatus I.
Figure 5:
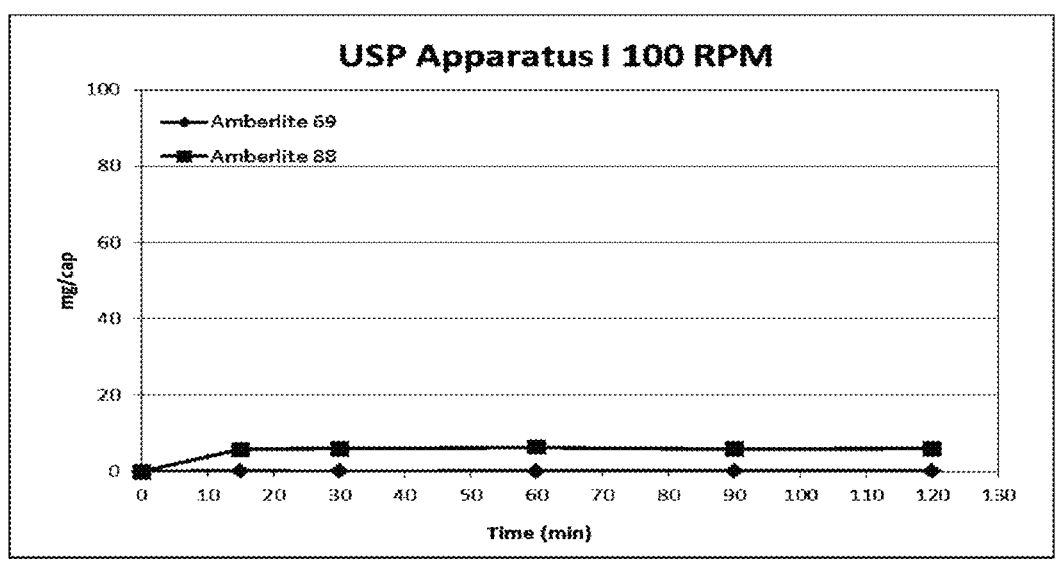
FIG. 5. In vitro drug release of an Amberlite™ IRP88 or Amberlite™ IRP69-dextromethorphan drug resinate in distilled water using USP Apparatus I.
Figure 6:
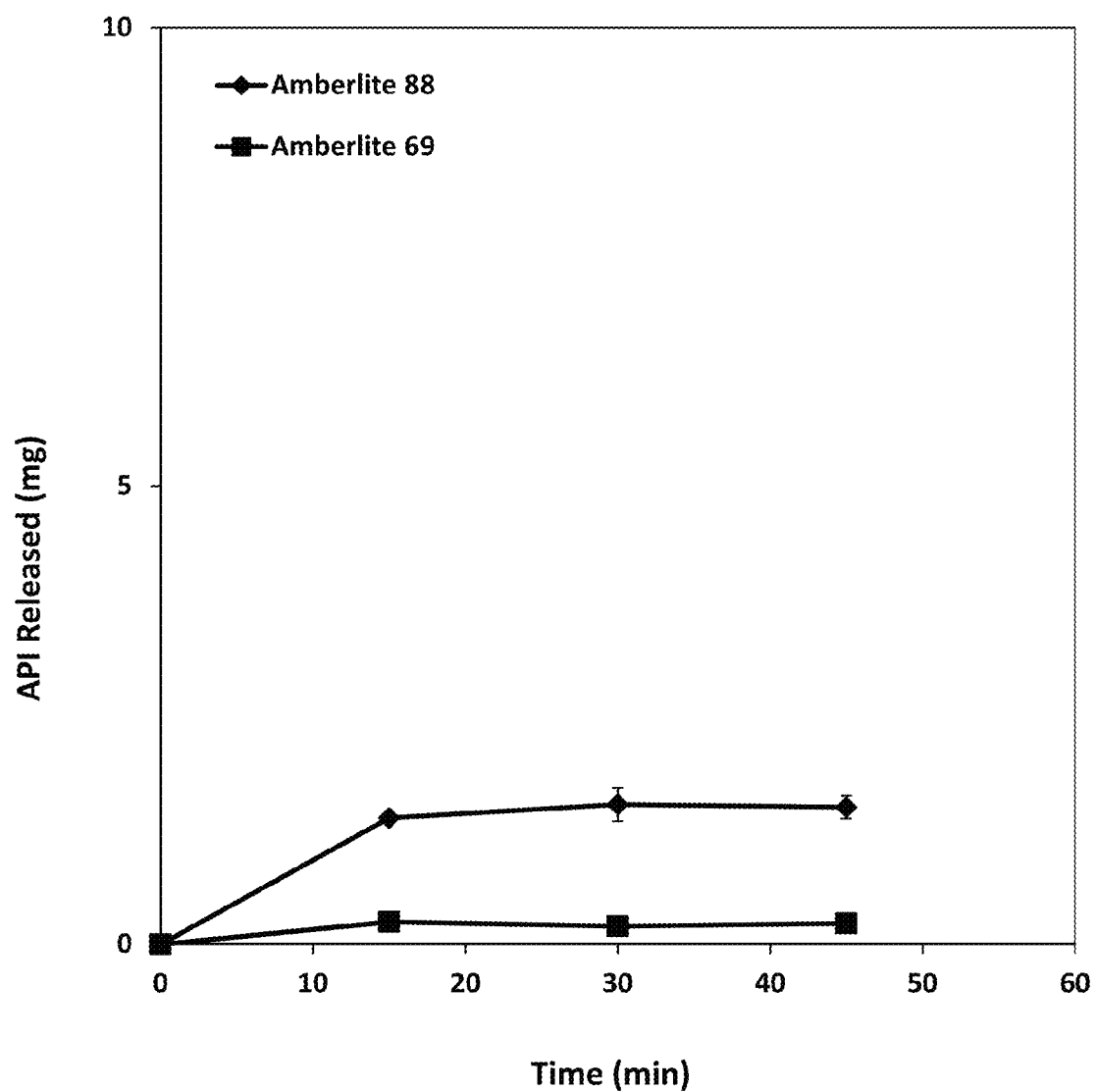
FIG. 6. In vitro drug release of an Amberlite™ IRP88 or Amberlite™ IRP69-dextromethorphan drug resinate in boiling distilled water.
Figure 7:
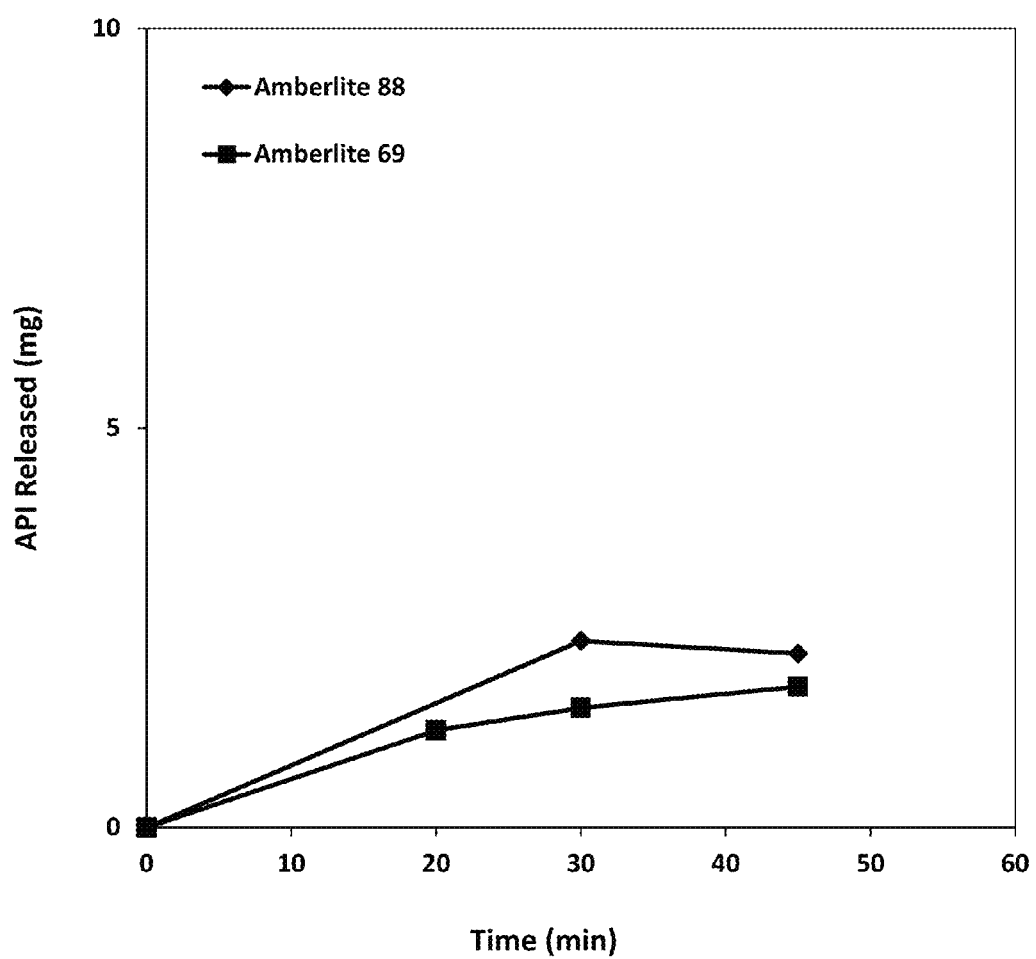
FIG. 7. In vitro drug release of an Amberlite™ IRP88 or Amberlite™ IRP69-dextromethorphan drug resinate in boiling distilled water.

The in vitro drug release from drug-resinate was assessed in DI water to demonstrate that the observed drug release from FIGS. 3 and 4 is resulting from the exchange of bound drug ions by ions normally present in body fluids. This test was carried out using the basket method (APP I) at 100 rpm in 900 mL with a dextromethorphan Amberlite™ IRP69 or Amberlite™ IRP88 resinate as shown in FIG. 5. The drug release in DI water is negligible suggesting that drug release occurs only in the presence of ions in the media. Drug release in boiling DI water and in boiling tap water was also negligible as shown in FIGS. 6 and 7.

Figure 8:
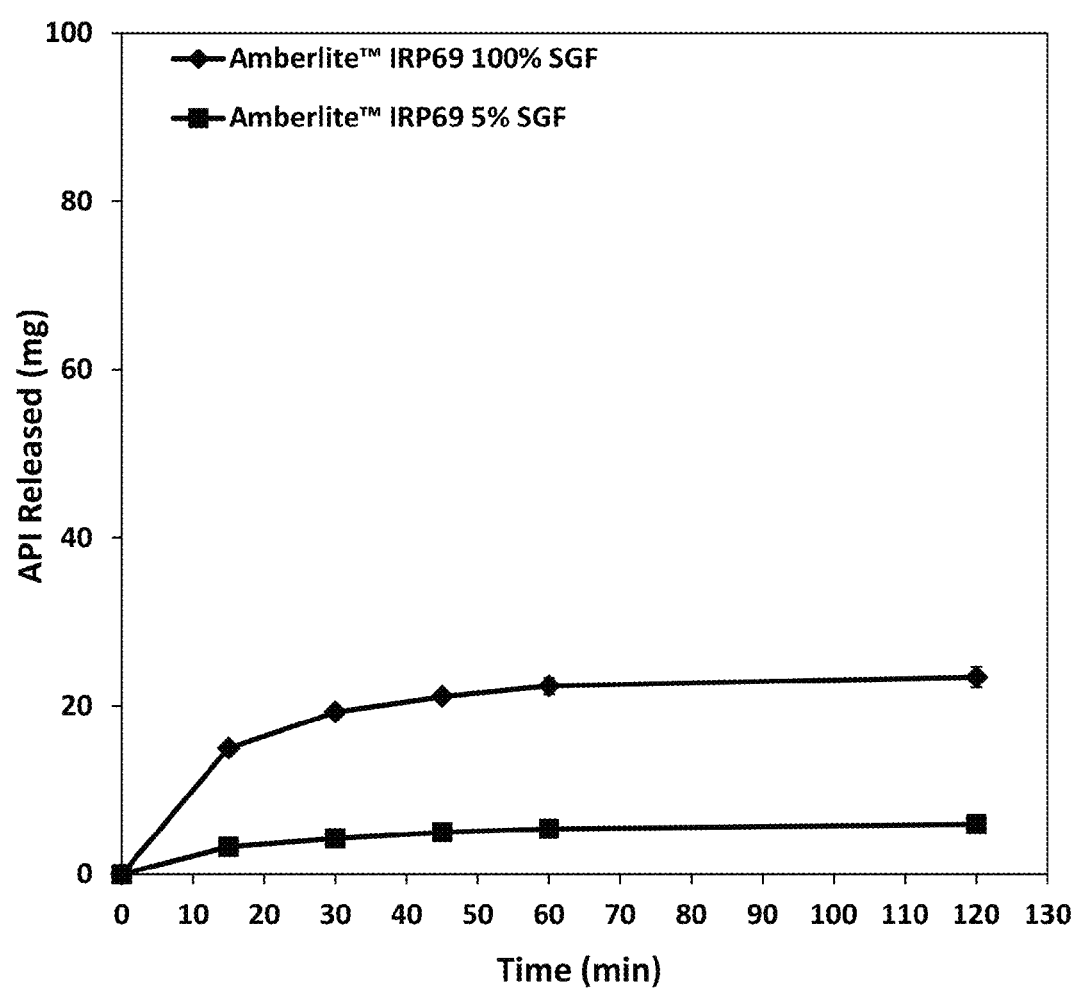
FIG. 8. In vitro drug release of an Amberlite™ IRP69-dextromethorphan drug resinate in simulated gastric fluid, pH 1.2 using USP Apparatus I.
Figure 9:
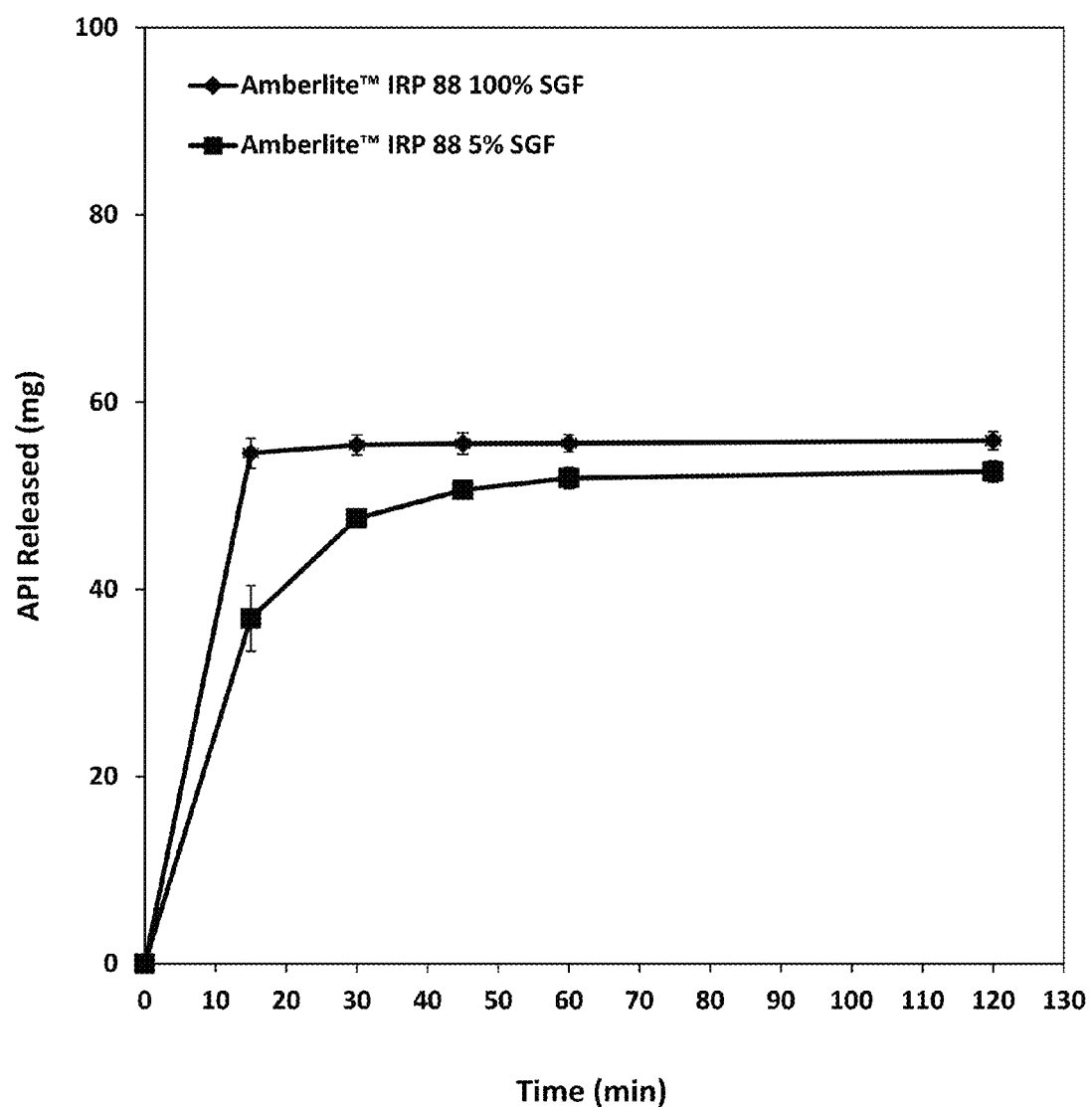
FIG. 9. In vitro drug release of an Amberlite™ IRP88-dextromethorphan drug resinate in simulated gastric fluid, pH 1.2 using USP Apparatus I.

Dissolution experiments for 200 mg dextromethorphan Amberlite™ IRP69 or Amberlite™ IRP88 resinates were also performed in simulated gastric fluid without pepsin. A stock solution was made with 2 g of NaCl in 7 mL of HCl and DI water to make 1000 mL of SGF at pH 1.2. The release profiles of dextromethorphan from two-piece hard shell capsules containing 200 mg of the dextromethorphan-resinate complexes are shown in FIGS. 8 and 9. These data show a pronounced effect of ion concentration on the release of dextromethorphan from Amberlite™ IRP69 (FIG. 8), while there is almost no difference in release between 100% SGF and 5% SGF from the weaker Amberlite™ IRP88 (FIG. 9).

Figure 10:
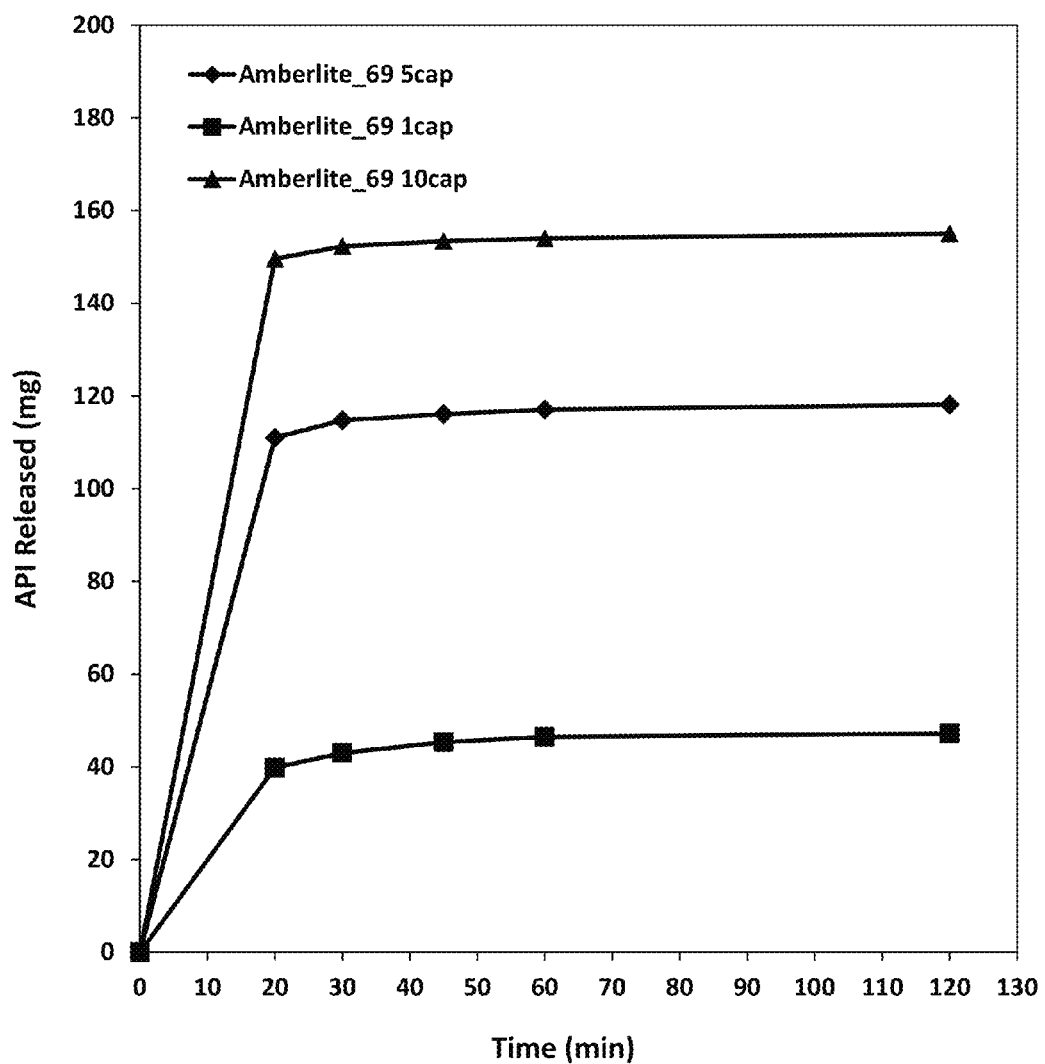
FIG. 10. In vitro drug release of an Amberlite™ IRP69-dextromethorphan drug resinate when either 1, 5, or 10 capsules were dissolved together in 0.1 N HCl using USP Apparatus II.

Overingestion or taking of more than the prescribed amount of pharmaceuticals is a common method of abuse. To test the anti-over ingestion properties of the pharmaceutical composition, multiple capsules were combined in a single reaction vessel and percentage of API released was measured. The Amberlite™ IRP69 composition was tested based upon its demonstrated ion-specific release profile. The in vitro dissolutions studies of dextromethorphan from Amberlite™ IRP69 from multiple capsules (1, 5, and 10) were carried out in 0.1 HCl with each 200 mg capsule containing 40 mg of the drug. As shown in FIG. 10, the amount of the drug released from 1 capsule was about 40 mg. Surprisingly, however, the amount of drug release was significantly lower than expected for multiple capsules dissolved simultaneously; 5 capsules released only 120 mg (theoretical amount should be about 200 mg) and 10 capsules released about 150 mg (theoretical amount should be about 400 mg). This result suggests that there is a ceiling effect for the dissolution of multiple capsules at once and suggests an alternative mechanism for preventing the overingestion of abuse prone active agents (e.g., oxycodone).

Figure 11:
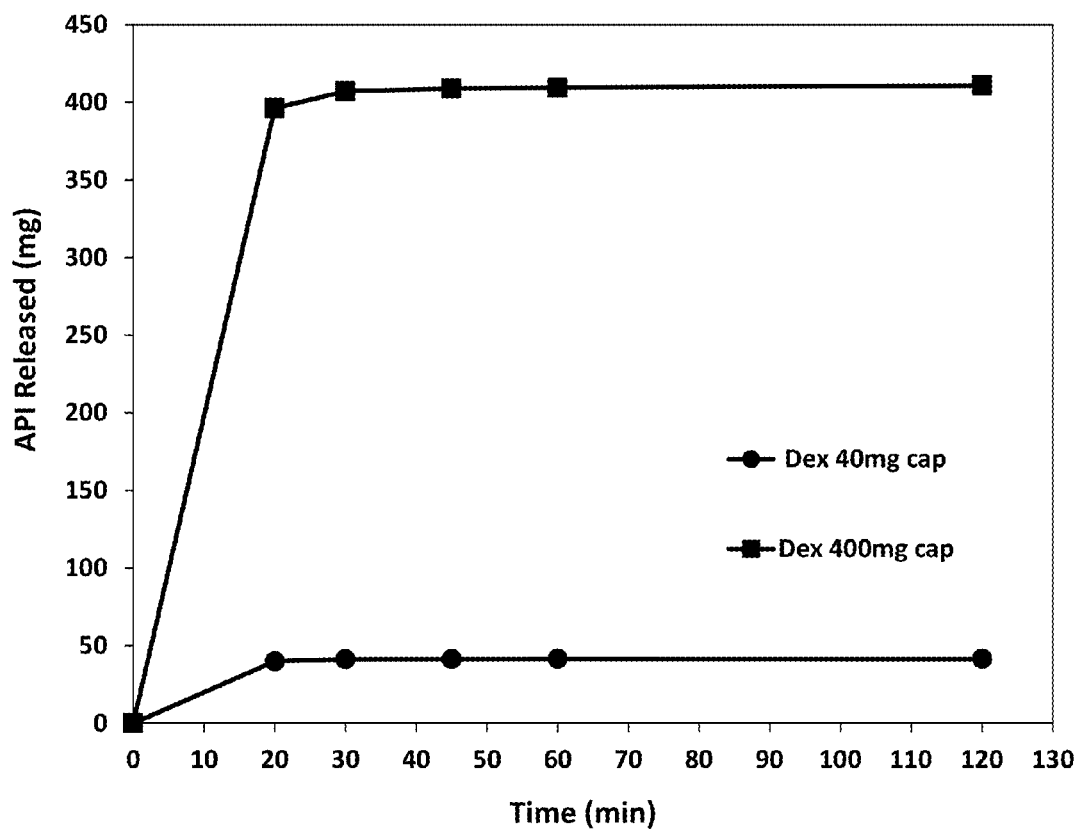
FIG. 11. In vitro drug release of dextromethorphan from control hard capsule shells (without resinate) when either 1 or 10 capsules were dissolved together in 0.1 N HCl using USP Apparatus II.

An additional experiment was performed to support the concept that the ceiling effect was not caused by solubility/sink limitation, but rather by retention by sequestering. As shown in FIG. 11, a single capsule without resin having 40 mg of dextromethorphan or 10 capsules without resin comprising a total amount of 400 mg of dextromethorphan had a dose proportional release. This result suggests that the observed ceiling effect is not restricted by any solubility or sink limitation, but rather imparted by the presence of a sequestering effect of the resin.

Figure 12:
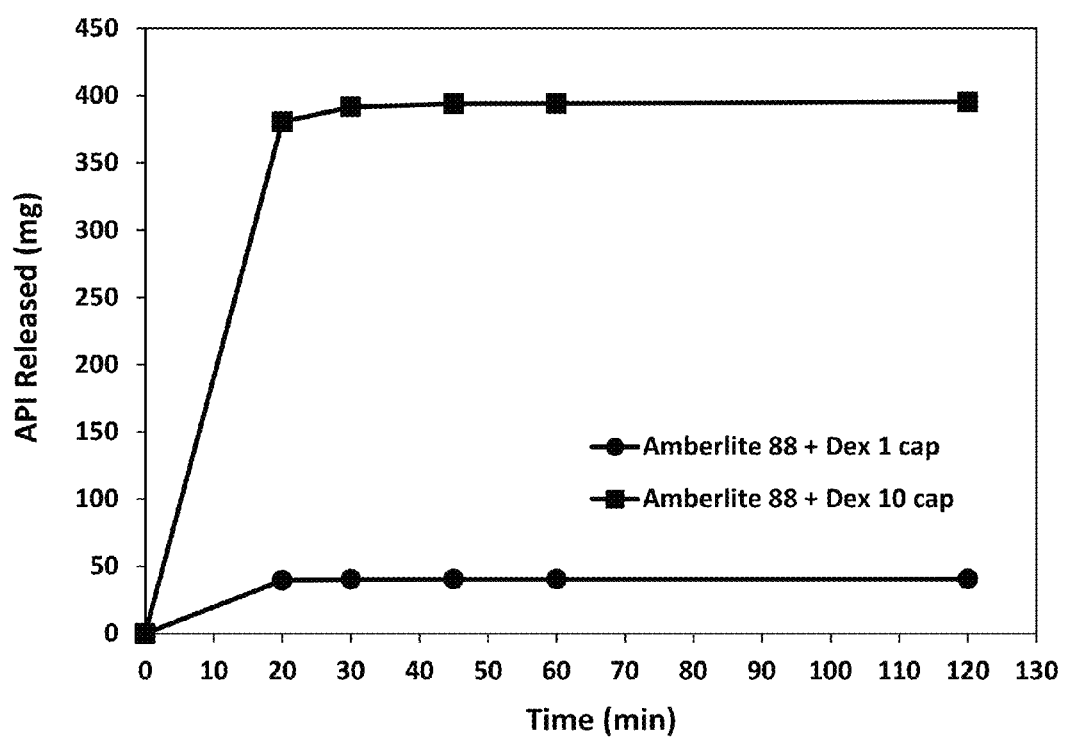
FIG. 12. In vitro drug release of an Amberlite™ IRP88-dextromethorphan drug physical blend when either 1 or 10 capsules were dissolved together in 0.1 N HCl using USP Apparatus II.
Figure 13:
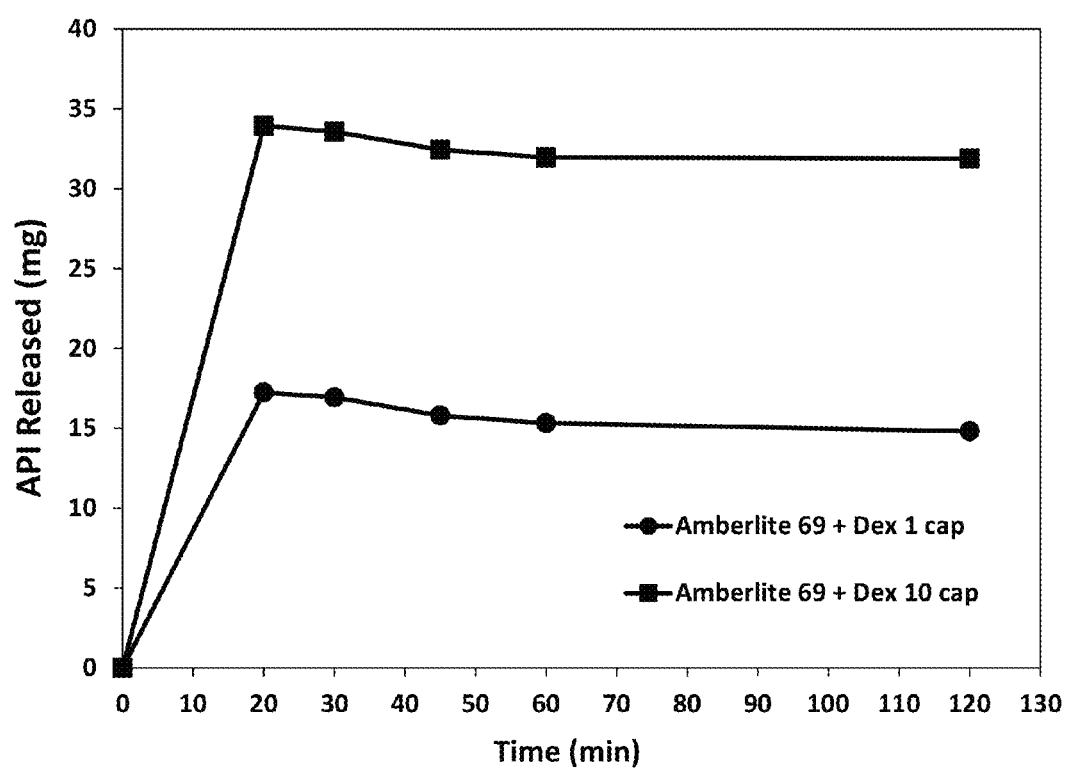
FIG. 13. In vitro drug release of an Amberlite™ IRP69-dextromethorphan drug physical blend when either 1 or 10 capsules were dissolved together in 0.1 N HCl using USP Apparatus II.

Next, the possibility to gain the same sequestering effect using physical blend of drug with resin instead of drug resinate complex was explored. The results presented in FIGS. 12 and 13 show that the release of dextromethorphan in the presence of Amberlite™ IRP69 is significantly lower compared to those obtained in the presence of Amberlite™ IRP88. This effect is more pronounced for 10 capsules containing 10-fold dose of Amberlite™ IRP69 in the same vessel as compared to 1 capsule per vessel. These findings are consistent with the results obtained with the dextromethorphan-Amberlite™ IRP69-resinate results.

Figure 14:
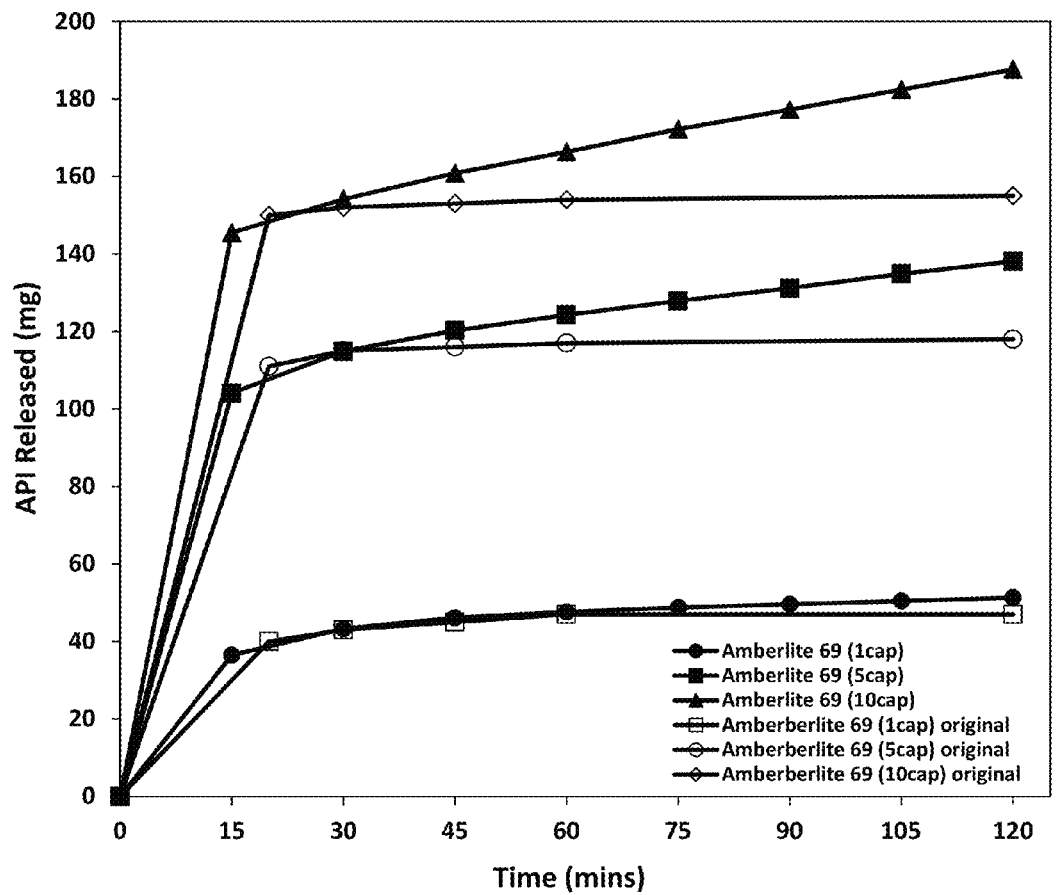
FIG. 14. In vitro drug release of an Amberlite™ IRP69- or Amberlite™ IRP88-dextromethorphan drug resinate when either 1, 5 or 10 capsules were dissolved together in 0.1 N HCl using USP Apparatus II with media renewal every 15 minutes.

The dissolution of hard capsules having a dextromethorphan-Amberlite™ IRP69-resinate and percent release of dextromethorphan was measured with media replacement every 15 minutes for 1, 5, and 10 capsules. As shown in FIG. 14, the percent release for 1, 5, and 10 capsules is very similar with and without media replacement with a small percent release delta at 120 minutes ($\Delta_{120}$) (Table 11).

TABLE 11

Delta between dextromethorphan-Amberlite ™ IRP69-resinate with/without media replacement

| No. Capsules | $\Delta_{120}$ (mg) |
| --- | --- |
| 1 | 4.3 |
| 15 | 20.1 |
| 10 | 33 |

Example 3

Next, the release of dextromethorphan from a drug-resinate or drug-physical blend complexes in abuse deterrent matrices were prepared and tested. These matrices were tested in the in vitro-in vivo relationship (IVIVR) dissolution method as shown in Table 12.

TABLE 12

In Vitro-In Vivo Relationship Testing Parameters

| Apparatus | USP Apparatus III |
| --- | --- |
| Agitation rate | 30 dips per minute (DPM) |
| Temperature | 37.0 ± 0.5° C. |
| Media volume | 250 mL |
| Media | 2 hours FaSSGF; 10 hours FaSSIF |
| Pull volume | 2 mL |
| Profiled sampling times | 1, 2, 4, 8, and 12 hours |

An abuse deterrent composition as shown in Table 13 was prepared by the following method. First, the specified amount of PEG 400 and Methocel™ A4M was dispensed in a beaker and let it hydrated for about an hour. Next the specified amount of soybean oil was heated to about 140° C. and the specified amount of Ethocel™ (20 cP) was added and mixed until a clear solution was obtained. The oil/Ethocel™ (20 cP) mixture was cooled to about 90° C. and the specified amount of carnauba wax and yellow bees wax was added and mixed until dissolved and the resulting solution was cooled to room temperature. The PEG 400 and Methocel™ A4M mixture was then added to the oil and wax mixture to obtain a uniform mix. This mixture was then homogenized for approximately 5 minutes until a smooth final fill mixture was obtained. A total of 4 g of dextromethorphan/Amberlite™ IRP88 resinate was added to 20 g of composition as shown in Table 13.

TABLE 13

Exemplary Abuse Deterrent Controlled Release Composition

| Components | Mass (mg/capsule) | Percentage (%) |
|---|---|---|
| Soybean Oil | 546 | 65 |
| Ethocel ™ (4cP) | 14 | 1.7 |
| Carnauba Wax | 17.5 | 2.0 |
| Bee's Wax | 17.5 | 2.0 |
| Methocel ™ A4M | 52.5 | 6.3 |
| Polyethylene Glycol 400 | 52.5 | 6.3 |
| Dextromethorphan/resinate | 140 | 16.7 |
| TOTAL | 840 | 100 |

Example 4

Figure 15:
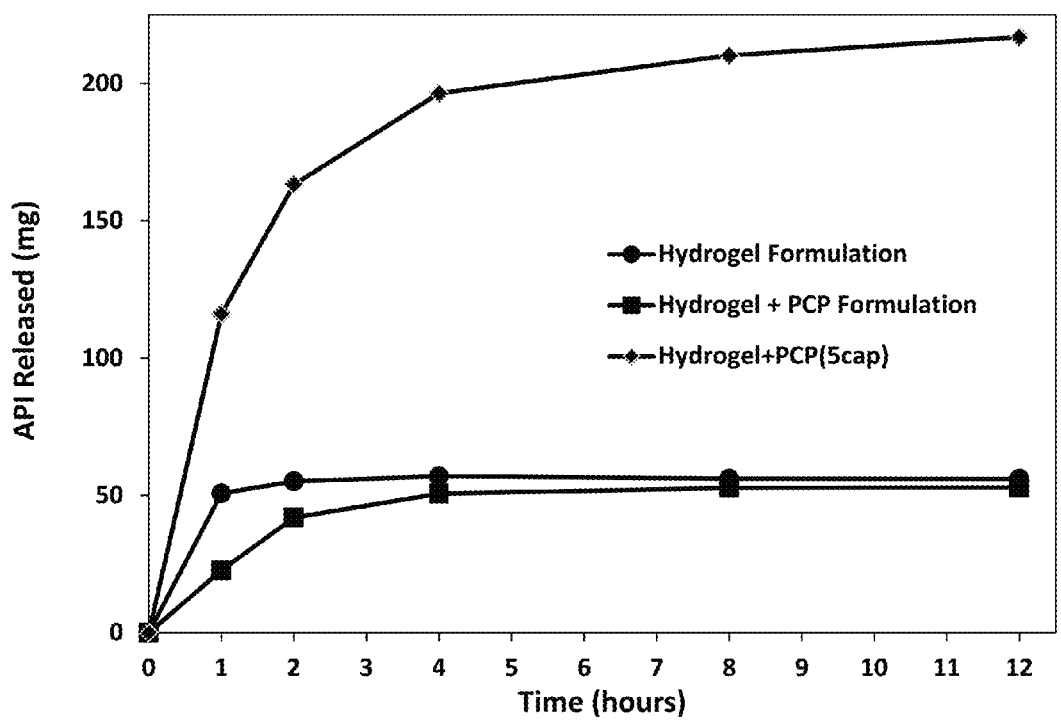
FIG. 15. In vitro drug release of Amberlite™ IRP88-dextromethorphan drug resinates in a hydrogel abuse deterrent composition according to the composition of Table 14 (–PCP) and Table 16 (+PCP) when either 1 or 5 capsules were dissolved together according to the parameters of Table 12.

Several abuse deterrent hydrogel formulations based on an abuse deterrent composition with a dextromethorphan/resinate complex were developed as shown in Tables 14-17. These compositions were then filled in a hard shell capsule for further dissolution testing using the dissolution apparatus III with the parameters shown in Table 12. The composition shown in Table 14 was supplemented with the adhesive polymer 5% polycarbophil (composition of Table 16) and about 50 mg dextromethorphan was complexed with about 50 mg of Amberlite™ IRP88 (1:1 ratio) as a resinate and tested by the same parameters. As shown in FIG. 15, a modest decrease in drug release was observed after 5 capsules were dissolved together in matrices containing PCP; the theoretical release is about 250 mg and 217 mg release was actually observed.

Figure 16:
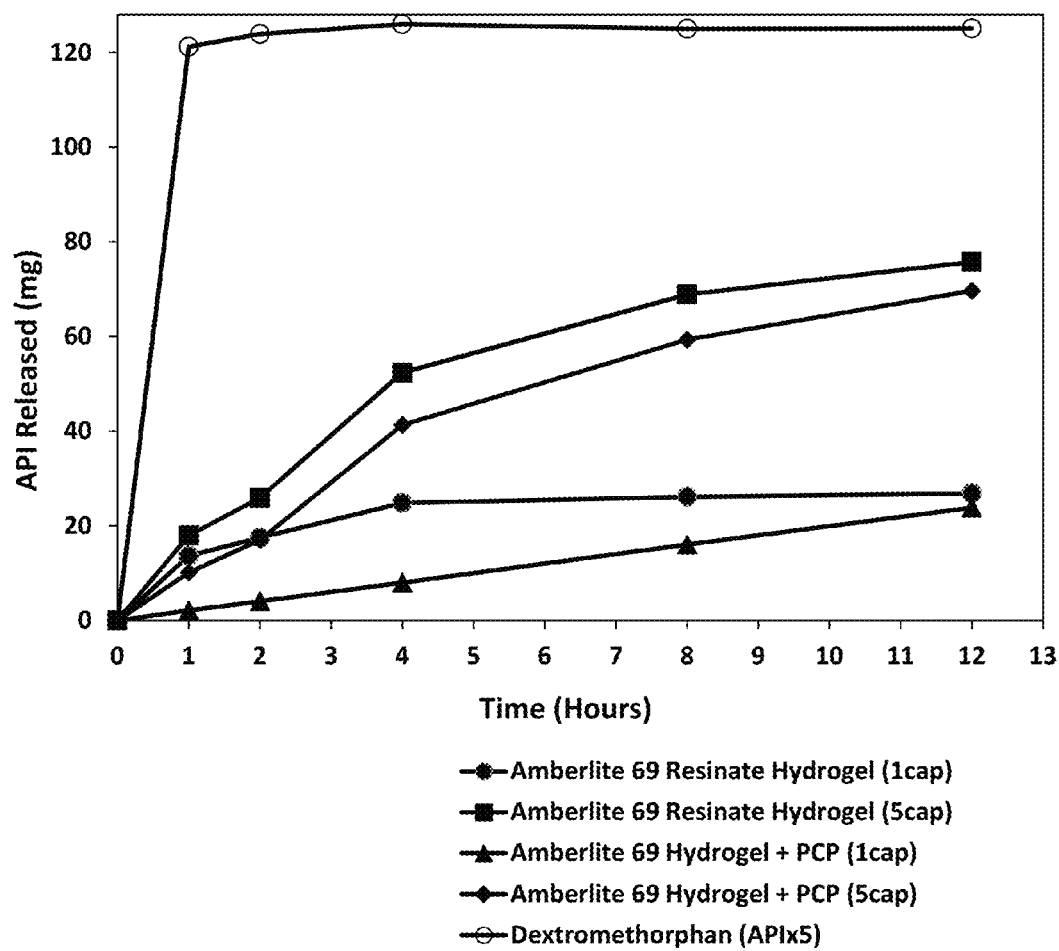
FIG. 16. In vitro drug release of Amberlite™ IRP69-dextromethorphan drug resinates in a hydrogel abuse deterrent composition according to the composition of Table 14 (–PCP) and Table 16 (+PCP) when either 1 or 5 capsules were dissolved together according to the parameters of Table 12.

The release of dextromethorphan from the composition according to Table 14 comprising 75 mg of Amberlite™ IRP69 and 25 mg of dextromethorphan in a resinate was tested. The addition of Polycarbophil according to the composition of Table 16 was added as an adhesive polymer to the Amberlite™ IRP69-dextromethorphan resinate to determine if the addition of polycarbophil promotes additional over ingestion ceiling effects in these compositions. As shown in FIG. 16, the dissolution of 1 capsule resulted in about 25 mg of dissolved dextromethorphan and the dissolution of 5 capsules resulted in the dissolution of 70-76 mg of dextromethorphan. There was a modest decrease in drug release with the addition of polycarbophil.

Figure 17:
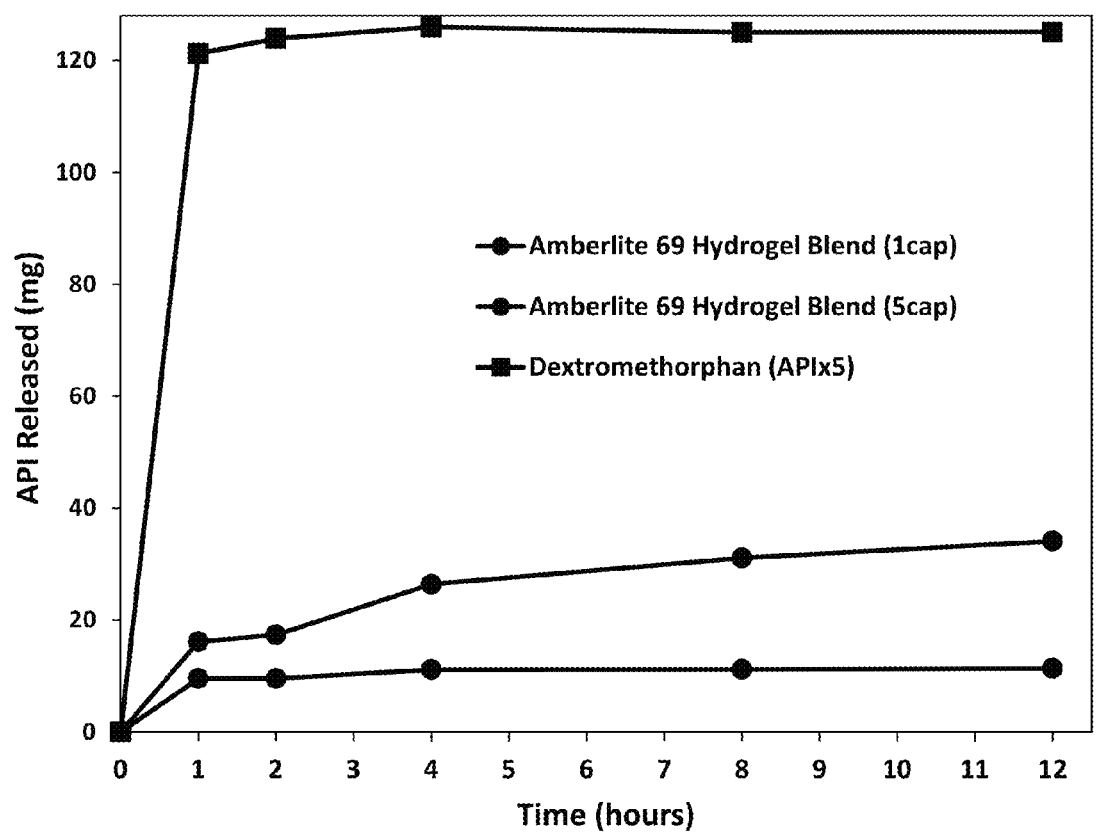
FIG. 17. In vitro drug release of Amberlite™ IRP69-dextromethorphan drug physical blend in a hydrogel abuse deterrent composition according to the composition of Table 14 when either 1 or 5 capsules were dissolved together or when 5 control dextromethorphan API-only containing compositions were dissolved according to the parameters of Table 12.

Next, the Amberlite™ IRP69-dextromethorphan blends with 25 mg of dextromethorphan and 75 mg of Amberlite™ IRP69 were tested. As shown in FIG. 17, these physical blends demonstrated a markedly decreased release rate for both 1 capsule and 5 capsules compared to the resinate blends shown in FIG. 16.

TABLE 14

Exemplary Abuse Deterrent Controlled Release Composition

| Components | Mass (mg/capsule) | Percentage (%) |
|---|---|---|
| Polyethylene Glycol 400 | 662.5 | 66.3 |
| Polyethylene Glycol 1000 | 92.5 | 9.3 |
| PVP K90 | 12.5 | 1.3 |
| Carbopol ® 974P | 12.5 | 1.3 |

TABLE 14-continued

Exemplary Abuse Deterrent Controlled Release Composition

| Components | Mass (mg/capsule) | Percentage (%) |
|---|---|---|
| HPMC K100M | 120 | 12 |
| Dextromethorphan/resinate | 100 | 10 |
| TOTAL | 1000 | 100 |

TABLE 15

Exemplary Abuse Deterrent Controlled Release Composition

| Components | Mass (mg/capsule) | Percentage (%) |
|---|---|---|
| Polyethylene Glycol 400 | 463 | 60.2 |
| Polyethylene Glycol 1000 | 64.8 | 8.4 |
| PVP K90 | 8.8 | 1.1 |
| Carbopol ® 974P | 8.8 | 1.1 |
| HPMC K100M | 84 | 10.9 |
| Dextromethorphan/resinate | 140 | 18.2 |
| TOTAL | 770 | 100 |

TABLE 16

Exemplary Abuse Deterrent Controlled Release Composition

| Components | Mass (mg/capsule) | Percentage (%) |
|---|---|---|
| Polyethylene Glycol 400 | 629 | 62.95 |
| Polyethylene Glycol 1000 | 88 | 8.8 |
| PVP K90 | 12 | 1.2 |
| Carbopol ® 974P | 12 | 1.2 |
| HPMC K100M | 114 | 11.4 |
| Polycarbophil | 50 | 5 |
| Dextromethorphan/resinate | 95 | 9.5 |
| TOTAL | 1050 | 100 |

TABLE 17

Exemplary Abuse Deterrent Controlled Release Composition

| Components | Mass (mg/capsule) | Percentage (%) |
|---|---|---|
| Polyethylene Glycol 400 | 461.7 | 57 |
| Polyethylene Glycol 1000 | 64.8 | 8 |
| PVP K90 | 9.7 | 1.2 |
| Carbopol ® 974P | 9.7 | 1.2 |
| HPMC K100M | 84.2 | 10.4 |
| Polycarbophil | 40.5 | 5 |
| Dextromethorphan/resinate | 140.1 | 17.3 |
| TOTAL | 810 | 100 |

Example 5

Exemplary soft capsules shells for encapsulating an abuse deterrent composition described herein, which in some aspects function to further limit the over ingestion of abuse prone drugs were designed. These soft capsule shells prevent over ingestion by promoting clumping of the one or more dosage forms, which limits drug dissolution out of the matrices described herein. These soft capsules have multiple charged ionic polymers that may be either integrated within the capsule gel mass or coated on a formed soft capsule. As described below, a soft gelatin capsule was generated and approximately half of the soft capsule shell was coated with a coating composition that comprises a negative polymer and the other half was coated with a coating composition that comprises a positive polymer as shown in Table 18.

TABLE 18

Exemplary Dual Charged Soft Capsule Shell Coatings

| Components | Positive Coating Percentage (%) | Negative Coating Percentage (%) |
|---|---|---|
| Gelatin | 26 | 29.2 |
| Methacrylic Acid Copolymer (EUDRAGIT ® L 100) | — | 11.2 |
| Dimethylaminoethyl Methacrylate Copolymer (EUDRAGIT ® EPO) | 12 | — |
| Glycerol | 16.5 | 18 |
| Triethyl citrate | 1.3 | |
| HCl | 0.5 | |
| Ammonium hydroxide | — | 1.7 |
| Titanium dioxide | — | 1.5 |
| Water | 44.2 | 37.1 |
| TOTAL | 100 | 100 |

Example 6

An exemplary anti-overingestion formulation was prepared by combining a 1:4 mass ratio of dry hydrocodone bitartrate and dry sodium polystyrene sulfonate IRP69 resin (e.g., Amberlite™ IRP69) and blending to form a powder suspension (Table 19). The resulting powder was filled into size 4 hard shell capsules to provide a dosage form comprising 5 mg hydrocodone bitartrate. This formulation provides an immediate release non-resin bound pharmaceutical composition.

TABLE 19

Anti-Overingestion Formulation

| Component | Mass (mg) | Weight Percent (%) |
|---|---|---|
| Hydrocodone Bitartrate | 5 | 20% |
| Sodium polystyrene sulfonate IRP69* | 20 | 80% |
| TOTAL | 25 mg | 100% |
| API: Resin Ratio | 1:4 | |

*AMBERLITE ™ IRP69 USP, sulfonated copolymer of stryene and divinylbenzene, pharmaceutical grade strong cation exchange resin; size 4 hard capsule A control composition comprising only the active pharmaceutical ingredient was also prepared (Table 20). Each hard capsule dosage form provides 5 mg of hydrocodone bitartrate.

TABLE 20

Anti-Overingestion Control

| Component | Mass (mg) | Weight Percent (%) |
|---|---|---|
| Hydrocodone Bitartrate | 5 | 100% |
| TOTAL | 5 mg | 100% |

Size 4 hard capsule

Example 7

Analytical analyses were performed on the composition shown in Table 19 and a control composition lacking the sodium polystyrene sulfonate IRP69 shown in Table 20.

TABLE 21

Analytical Analysis of Anti-Overingestion Formulation

| Test/Methods | Acceptable limits | Results |
|---|---|---|
| Test Sample (Table 19) hydrocodone bitartrate immediate release capsules with sodium polystyrene sulfonate IRP69, 5 mg API | | |
| Physical Description | Two pice hard shell capsule, no printing; tan powder | Pass |
| Identification (HPLC; PD16-275) | Retention time of sample is between 0.98 and 1.02 relative to average retention time of standard hydrocodone bitartrate | Pass |
| Assay (PD16-275) | Report results | 99.9% |
| Control Sample (Table 20) hydrocodone bitartrate immediate release capsules, 5 mg API | | |
| Physical Description | Two pice hard shell capsule, no printing; white powder | Pass |
| Identification (HPLC; PD16-275) | Retention time of sample is between 0.98 and 1.02 relative to average retention time of standard hydrocodone bitartrate | Pass |
| Assay (PD16-275) | Report results | 99.9% |

Example 8

Pharmacokinetic Crossover Study of Two Orally Administered Hydrocodone Formulations in Beagle Dogs A pharmacokinetic study was conducted using the formulations shown in Table 19 comprising 5 mg hydrocodone bitartrate and 20 mg of Amberlite™ IRP69. Control samples contained 5 mg hydrocodone bitartrate (no resin; Table 20).

A total of six male beagle dogs were assigned to the study. The same animals were used for each phase, with a minimum 3-day washout period between dosing in each phase. For each phase, all animals were fasted for at least eight hours prior to dosing and through the first four hours of blood sample collection, (food was returned 30 minutes following collection of the last blood sample at the 4-hour collection interval). The total fasting time did not exceed 24 hours.

For each phase, one animal per group (Groups 1-6) received an oral capsule dose of the appropriate Test formulation or Control formulation as outlined in Tables 22-23. Animals were dosed in a latin-square design, with each animal receiving each of six treatments once in a rotating fashion, as outlined below. For each dose, at approximately 30 minutes (±5 minutes) prior to test article administration, each animal received 25 mg of naltrexone (one half of a 50 mg tablet) to block the opioid effects of the test article. In addition, naloxone (0.02-0.04 mg/kg, IV) was available as a rescue medication, if opiate overdose effects (e.g., respiratory depression) were noted following test article administration.

Blood samples, 0.5 mL/sample, were collected in K2EDTA vacutainers from the jugular vein at the following times: predose (0) and 0.25, 0.5, 0.75, 1, 1.25, 1.5, 2, 3, 4, 6, 8, 10, 12 and 14-hours postdose. All blood samples were placed on wet ice following collection until centrifuging and plasma was isolated. Plasma samples were analyzed for the concentration of test article over the applicable range (e.g., 1 ng/mL to 1,000 ng/mL) using a HPLC mass spectrometry (HPLC MS/MS) method.

All animals were observed at least twice a day for morbidity, mortality, injury, and availability of food and water. Any animals in poor health were identified for further monitoring and possible euthanasia. For each dose, body weights were measured and recorded on the day of dosing or the day prior to dosing. A detailed clinical examination for each animal was performed pretest and relevant observations were recorded.

A model independent method was used to determine $C_{max}$, $T_{max}$ and AUC values for the test article from concentration-time data in the Test species. Based on the data, appropriate parameters were estimated including: $C_{max}$/Dose, $AUC_{Tlast}$, $AUC_{0-\tau}$, AUC/Dose, and Control Ratio (at each dose level tested)=$AUC_{Test}/AUC_{control}$.

Results are shown in Tables 24-25.

TABLE 22

Study Design Parameters

| Groups | Treatment | Number | Dose Route | Dose Level (mg/animal) | Dose Amount (capsule/animal) | Collection Interval |
|---|---|---|---|---|---|---|
| 1-6 | Test Hydrocodone-Resin or Hydrocodone Control | 1 ♂ animal/group | Oral Capsule* | 5, 25, or 50 mg as specified | 1, 5, or 10 capsules as specified | Blood† |

*All animals were pretreated with a single oral tablet 25 mg dose of naltrexone prior to test article administration in each phase. All capsules had 5 mg hydrocodone bitartrate per capsule.
†Blood samples were collected predose (0) and at 0.25, 0.5, 0.75, 1, 1.25, 1.5, 2, 3, 4, 6, 8, 10, 12 and 14- hours postdose.

TABLE 23

Dosing Protocol (male beagle dogs)
Treatment

| | Phase 1 | | Phase 2 | | Phase 3 | | Phase 4 | | Phase 5 | | Phase 6 | |
|---|---|---|---|---|---|---|---|---|---|---|---|---|
| Grp | Dose (mg) | Qant.# | Dose (mg) | Qant.# | Dose (mg) | Qant.# | Dose (mg) | Qant.# | Dose (mg) | Qant.# | Dose (mg) | Qant.# |
| 1 | 5 T$^a$ | 1 | 25 T | 5 | 50 T | 10 | 5 C | 1 | 25 C | 5 | 50 C | 10 |
| 2 | 25 T | 5 | 50 T | 10 | 5 C | 1 | 25 C | 5 | 50 C | 10 | 5 T | 1 |
| 3 | 50 T | 10 | 5 T | 1 | 25 C | 5 | 50 C | 10 | 5 T | 1 | 25 T | 5 |
| 4 | 50 C$^b$ | 1 | 25 C | 5 | 50 C | 10 | 5 T | 1 | 25 T | 5 | 50 T | 10 |
| 5 | 25 C | 5 | 50 C | 10 | 5 T | 1 | 25 T | 5 | 50 T | 10 | 5 C | 1 |
| 6 | 50 C | 10 | 5 C | 1 | 25 T | 5 | 50 T | 10 | 5 C | 1 | 25 C | 5 |

$^a$T = Test dosage form containing 20 mg Amberlite™ IRP69 resin and 5 mg of hydrocodone bitartrate per capsule.
$^b$C = Control dosage form containing 5 mg of hydrocodone bitartrate per capsule.
Number of capsules administered per animal; all capsules contain 5 mg of hydrocodone bitartrate per capsule.

Table 24 shows the average hydrocodone plasma concentration as a function of time for the Test and Control compositions at 5 mg, 25 mg, and 50 mg doses. These data are plotted in FIG. 18.

TABLE 24

Average Plasma Hydrocodone Concentrations for Test and Control Doses in Male Dogs

| Time | Test | | | Control | | |
|---|---|---|---|---|---|---|
| (h) | 5 mg | 25 mg | 50 mg | 5 mg | 25 mg | 50 mg |
| 0.0 | 0.5 | 0.0 | 0.4 | 0.3 | 0.4 | 0.7 |
| 0.25 | 1.2 | 2.4 | 1.6 | 5.6 | 11.6 | 34.4 |
| 0.5 | 2.9 | 14.0 | 17.1 | 11.8 | 88.2 | 152.6 |
| 0.75 | 5.9 | 57.7 | 39.8 | 23.6 | 91.5 | 174.1 |
| 1.0 | 12.2 | 58.3 | 68.7 | 17.7 | 99.1 | 150.7 |
| 1.25 | 13.1 | 95.2 | 93.0 | 26.6 | 106.9 | 175.9 |
| 1.5 | 18.6 | 98.6 | 145.1 | 23.4 | 90.4 | 187.3 |
| 2.0 | 20.8 | 77.7 | 150.0 | 19.7 | 72.2 | 162.0 |
| 3.0 | 12.1 | 47.2 | 91.0 | 10.1 | 38.9 | 77.4 |
| 4.0 | 5.7 | 25.7 | 60.0 | 5.6 | 24.6 | 48.6 |
| 6.0 | 1.7 | 10.9 | 24.8 | 1.8 | 7.4 | 14.2 |
| 8.0 | 0.8 | 5.4 | 11.9 | 0.8 | 3.0 | 7.6 |
| 10.0 | 0.6 | 3.3 | 7.7 | 0.2 | 1.8 | 4.1 |
| 12.0 | 0.4 | 2.3 | 6.3 | 0.5 | 1.3 | 3.2 |
| 14.0 | 0.6 | 1.6 | 5.4 | 0.3 | 0.6 | 2.2 |

TABLE 25

Pharmacokinetic Parameters Following a Single Oral Administration of 5, 25, or 50 mg Hydrocodone and Resin (T) or Hydrocodone Control (C) to Male Beagle Dogs

| Treatmt | Stat | $C_{max}$ (ng/mL) | $C_{max}$/dose (ng/mL/mg) | $T_{max}$ (hr)[a] | $T_{last}$ (hr)[a] | $AUC_{Tlast}$ (hr·ng/mL) | $AUC_{0-14hr}$ (hr·ng/mL) | $AUC_{0-14hr}$/Dose (hr*ng/mL/mg) | Test:Control Ratio[b] |
|---|---|---|---|---|---|---|---|---|---|
| 5 mg T | N | 6 | 6 | 6 | 6 | 6 | 6 | 6 | 6 |
|  | Mean | 26.3 | 5.25 | NA | 6 | 57.1 | 59.6 | 11.9 | 0.953 |
|  | SD | 6.53 | 1.31 | (1-2) | (4-14) | 19.7 | 18.5 | 3.69 | 0.567 |
|  | CV% | 24.9 | 24.9 | NA | NA | 34.6 | 30.9 | 30.9 | 59.5 |
| 25 mg T | N | 6 | 6 | 6 | 6 | 6 | 6 | 6 | 6 |
|  | Mean | 105 | 4.21 | NA | NA | 282 | 283 | 11.3 | 1.01 |
|  | SD | 29.4 | 1.18 | (0.75-1.5) | (10-14) | 67.7 | 67.7 | 2.71 | 0.313 |
|  | CV% | 27.9 | 27.9 | NA | NA | 24.0 | 23.9 | 23.9 | 31.1 |
| 50 mg T | N | 6 | 6 | 6 | 6 | 6 | 6 | 6 | 5 |
|  | Mean | 178 | 3.57 | 1.5 | 14 | 510 | 510 | 10.2 | 0.834 |
|  | SD | 71.5 | 1.43 | (1-2) | (14-14) | 182 | 182 | 3.63 | 0.168 |
|  | CV% | 40.1 | 40.1 | NA | NA | 35.7 | 35.7 | 35.7 | 20.1 |
| 5 mg C | N | 6 | 6 | 6 | 6 | 6 | 6 | 6 | NA |
|  | Mean | 36.2 | 7.24 | NA | 6 | 68.5 | 70.3 | 14.1 | NA |
|  | SD | 14.0 | 2.81 | (0.75-2) | (4-14) | 20.3 | 19.7 | 3.95 | NA |
|  | CV% | 38.8 | 38.8 | NA | NA | 29.7 | 28.1 | 28.1 | NA |
| 25 mg C | N | 6 | 6 | 6 | 6 | 6 | 6 | 6 | NA |
|  | Mean | 150 | 6.01 | 1 | NA | 290 | 291 | 11.6 | NA |
|  | SD | 41.1 | 1.64 | (0.5-2) | (8-14) | 58.3 | 57.6 | 2.31 | NA |
|  | CV% | 27.3 | 27.3 | NA | NA | 20.1 | 19.8 | 19.8 | NA |
| 50 mgC | N | 5 | 5 | 5 | 5 | 5 | 5 | 5 | NA |
|  | Mean | 300 | 6.00 | 1.5 | 14 | 591 | 592 | 11.8 | NA |
|  | SD | 163 | 3.26 | (0.5-2) | (12-14) | 111 | 110 | 2.20 | NA |
|  | CV% | 54.4 | 54.4 | NA | NA | 18.7 | 18.6 | 18.6 | NA |

NA: Not applicable.
[a]Median (minimum-maximum), median value only reported if actual collection interval.
[b]Test: Control Ratio = $AUC_{0-14hr}$ Test/$AUC_{0-14hr}$ Control.

Figure 18:
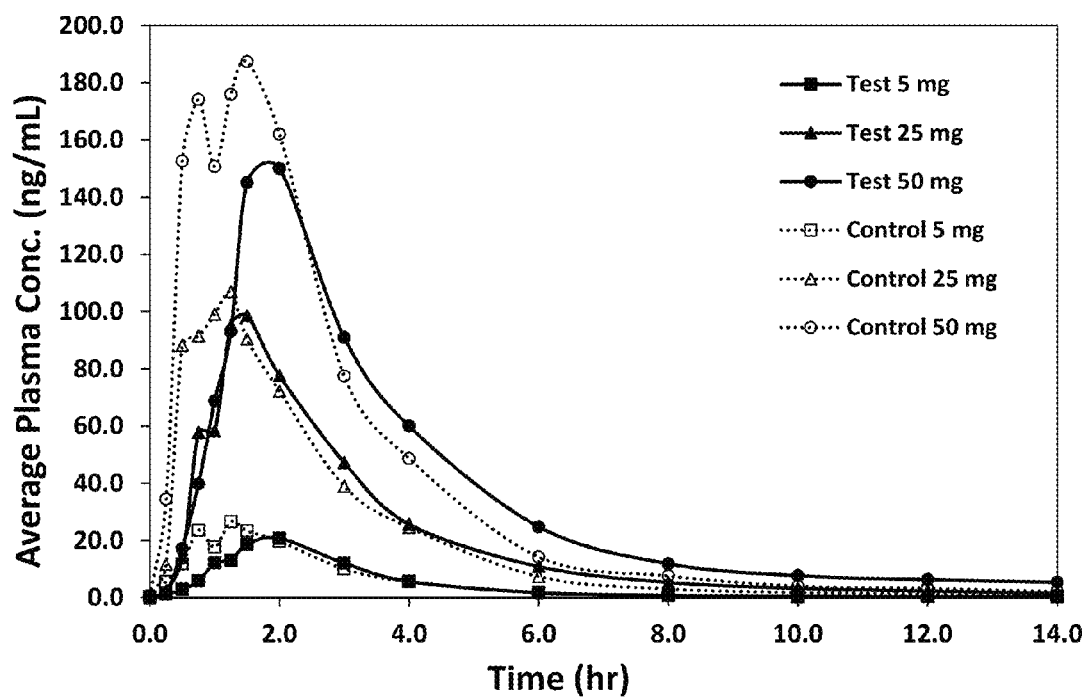
FIG. 18. Pharmacokinetic results from hydrocodone formulations in male dogs. Average plasma concentration of hydrocodone as a function of time for the Test and Control dosage forms at shown in Tables 19-20.
Figure 19:
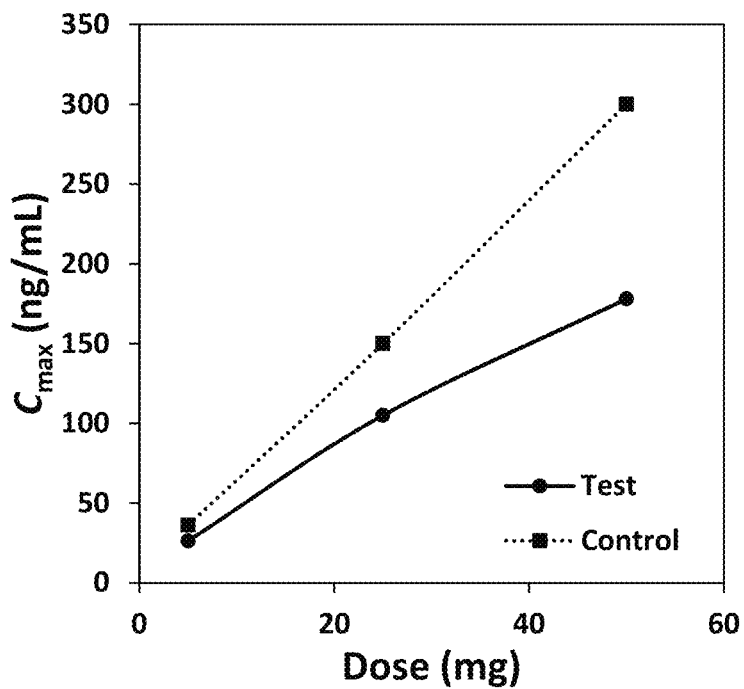
FIG. 19. Pharmacokinetic results from hydrocodone formulations in male dogs. (A) $C_{max}$ versus dose for 5 mg, 25 mg, and 50 mg doses. (B) $C_{max}$/dose for the same data in A.
Figure 19:
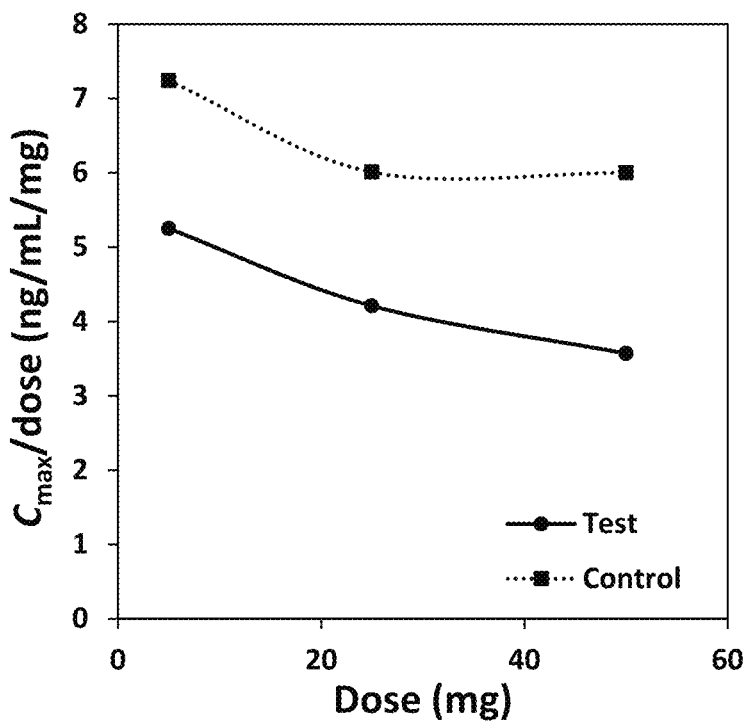
Figure 20:
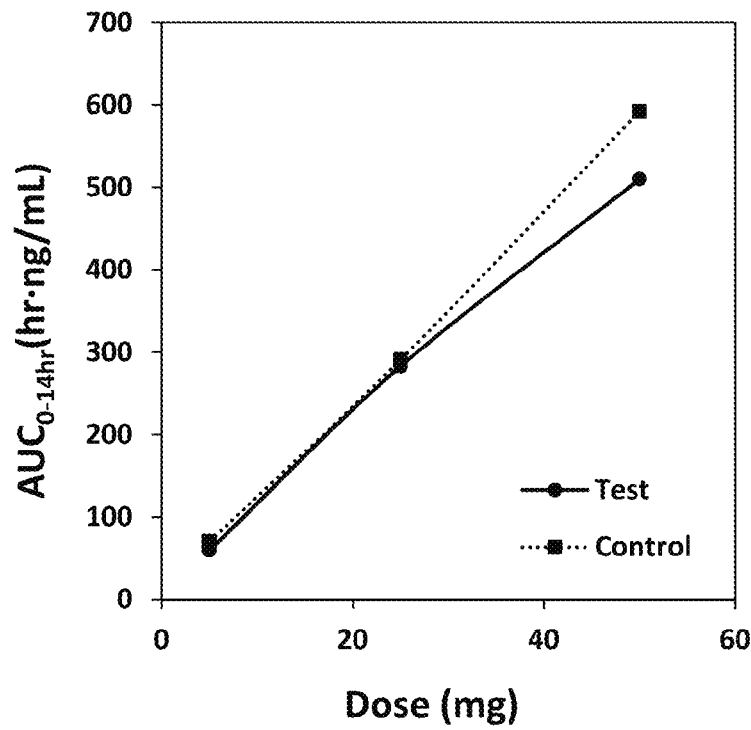
FIG. 20. Pharmacokinetic results from hydrocodone formulations in male dogs. (A) $AUC_{0-14hr}$ versus dose for 5 mg, 25 mg, and 50 mg doses. (B) $AUC_{0-14\ hr}$/dose for the same data in A.
Figure 20:
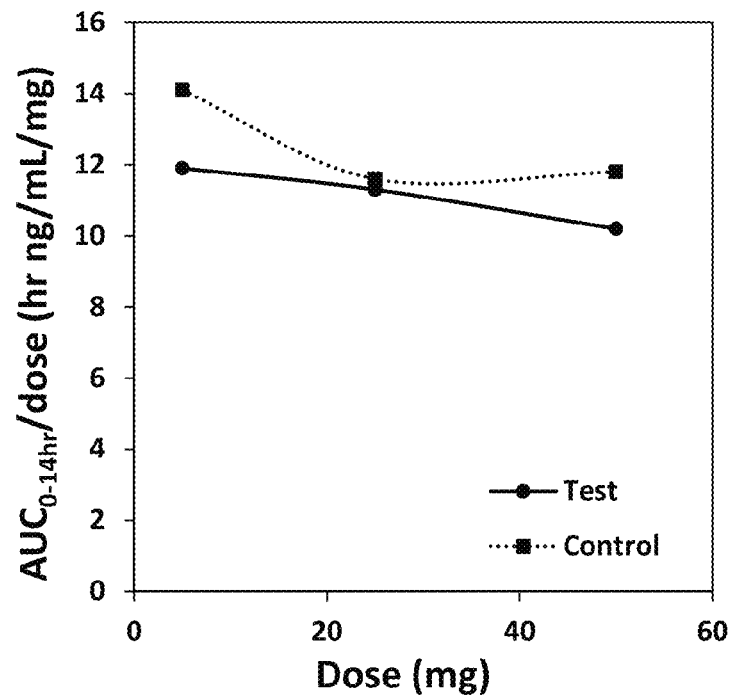

Results are shown in FIGS. 18-19.

TABLE 26

Individual Pharmacokinetic Parameters Following a Single Oral Administration of 5, 25, or 50 mg Hydrocodone and Resin (T) or Hydrocodone Control (C) to Male Beagle Dogs

| Treat. | Gender | Subject | $C_{max}$ (ng/mL) | $C_{max}$/dose (ng/mL/mg) | $T_{max}$ (hr)[a] | $T_{last}$ (hr) | $AUC_{last}$ (hr·ng/mL) | $AUC_{0-14hr}$ (hr·ng/mL) | $AUC_{0-14hr}$/Dose (hr*ng/mL/mg)[a] | Test:Control Ratio[a] |
|---|---|---|---|---|---|---|---|---|---|---|
| 5 mg T | ♂ | 101 | 18.5 | 3.70 | 2 | 6 | 40.1 | 41.8 | 8.36 | 0.658 |
|  | ♂ | 102 | 37.4 | 7.48 | 1 | 8 | 62.7 | 64.1 | 12.8 | 1.18 |
|  | ♂ | 103 | 27.0 | 5.40 | 1.5 | 14 | 91.2 | 91.2 | 18.2 | 2.00 |
|  | ♂ | 104 | 22.8 | 4.56 | 1 | 6 | 60.3 | 62.1 | 12.4 | 0.627 |
| 25 mg T | ♂ | 105 | 28.8 | 5.76 | 2 | 4 | 51.6 | 58.0 | 11.6 | 0.747 |
|  | ♂ | 106 | 23.1 | 4.62 | 2 | 4 | 36.5 | 40.7 | 8.13 | 0.494 |
|  | ♂ | 101 | 107 | 4.28 | 1.5 | 12 | 279 | 281 | 11.2 | 0.787 |
|  | ♂ | 102 | 108 | 4.32 | 0.75 | 12 | 294 | 295 | 11.8 | 1.09 |
| 50 mg T | ♂ | 103 | 91.0 | 3.64 | 1 | 14 | 264 | 264 | 10.6 | 1.29 |
|  | ♂ | 104 | 145 | 5.80 | 1.5 | 14 | 399 | 399 | 16.0 | 1.43 |
|  | ♂ | 105 | 122 | 4.88 | 1.25 | 10 | 269 | 270 | 10.8 | 0.763 |
|  | ♂ | 106 | 57.9 | 2.32 | 1.5 | 14 | 189 | 189 | 7.56 | 0.673 |
| 5 mg C | ♂ | 101 | 23.5 | 4.70 | 2 | 6 | 62.2 | 63.5 | 12.7 | 0.783 |
|  | ♂ | 102 | 43.2 | 8.64 | 1.25 | 4 | 49.6 | 54.1 | 10.8 | 0.895 |
|  | ♂ | 103 | 24.5 | 4.90 | 1.5 | 6 | 44.3 | 45.5 | 9.10 | 0.673 |
|  | ♂ | 104 | 33.1 | 6.62 | 1 | 8 | 97.6 | 99.0 | 19.8 | 1.10 |
| 25 mg C | ♂ | 105 | 60.9 | 12.2 | 0.75 | 4 | 75.0 | 77.6 | 15.5 | NA |
|  | ♂ | 106 | 32.0 | 6.40 | 0.75 | 14 | 82.4 | 82.4 | 16.5 | 0.723 |
|  | ♂ | 101 | 168 | 6.72 | 0.5 | 14 | 357 | 357 | 14.3 | 0.658 |
|  | ♂ | 102 | 85.0 | 3.40 | 2 | 12 | 267 | 270 | 10.8 | 1.18 |
| 50 mg C | ♂ | 103 | 124 | 4.96 | 1.25 | 8 | 202 | 204 | 8.17 | 2.00 |
|  | ♂ | 104 | 203 | 8.12 | 0.5 | 8 | 277 | 279 | 11.1 | 0.627 |
|  | ♂ | 105 | 152 | 6.08 | 1.5 | 10 | 353 | 354 | 14.2 | 0.747 |
|  | ♂ | 106 | 170 | 6.80 | 0.75 | 14 | 281 | 281 | 11.3 | 0.494 |

NA: Not applicable.
[a] Test: Control Ratio = $AUC_{0-14hr}$ Test/$AUC_{0-14hr}$ Control Table 27 shows the difference (absolute value) and percentage difference for $C_{max}$ and $AUC_{0-14hr}$ between the Test and Control data shown in Table 24.

TABLE 27

Differences between Test and Control Pharmacokinetic Parameters at Each Dose

| Dose | $C_{max}$ Test | $C_{max}$ Control | Difference | % Difference |
|---|---|---|---|---|
| 5 mg | 26.3 | 36.2 | 9.9 | 31.7% |
| 25 mg | 105 | 150 | 45 | 35.3% |
| 50 mg | 178 | 300 | 122 | 51.1% |

| Dose | $AUC_{0-14}$ Test | $AUC_{0-14}$ Control | Difference | % Difference |
|---|---|---|---|---|
| 5 mg | 59.6 | 70.3 | 10.7 | 16.5% |
| 25 mg | 283 | 291 | 8 | 2.8% |
| 50 mg | 510 | 592 | 82 | 14.9% |

What is claimed is:

1. An oral pharmaceutical composition comprising an immediately releasing dry admixture of an opioid agonist or a salt thereof and one or more strong cation exchange resins at a mass ratio of about 1:2 to about 1:8 and optionally, one or more pharmaceutically acceptable excipients,
    wherein less than about 1% of the opioid agonist is bound to the strong cation exchange resin prior to solvation; and
    after solvation of two more doses of the composition simultaneously or successively over about a 4-hour period, the strong cation exchange resin adsorbs about 15% to about 70% by mass of the opioid agonist and impedes its absorption into a subject's systemic circulation, lowering $C_{max}$ for the opioid agonist by about 30% to about 50% as compared to an equivalent dose of the opioid agonist lacking a strong cation exchange resin.

2. The composition of claim 1, wherein subjects administered the composition exhibit one or more of the following pharmacokinetic parameters:
    (a) a delayed $T_{max}$ for the opioid agonist as compared to an equivalent opioid agonist dose lacking a strong cation exchange resin;
    (b) a lower plasma AUC for the opioid agonist as compared to an equivalent opioid agonist dose lacking a strong cation exchange resin;
    (c) an extended absorption time for the opioid agonist as compared to an equivalent opioid agonist dose lacking a strong cation exchange resin; or
    (d) an extended clearance time for the opioid agonist as compared to an equivalent opioid agonist dose lacking a strong cation exchange resin.

3. The composition of claim 1, wherein the mass ratio of opioid agonist to strong cation exchange resin is about 1:4.

4. The composition of claim 1, wherein the opioid agonist comprises hydrocodone.

5. The composition of claim 1, wherein the strong cation exchange resin comprises polystyrene sulfonate or a salt thereof.

6. The composition of claim 1, wherein the composition comprises:
    about 10% to about 30% by mass of hydrocodone; and
    about 70% to 90% by mass of a strong cation exchange resin.

7. The composition of claim 1, wherein the composition comprises:
    about 20% by mass of hydrocodone; and
    about 80% by mass of a strong cation exchange resin.

8. The composition of claim 1, wherein the composition comprises:
    about 20% by mass of hydrocodone bitartrate; and
    about 80% by mass of polystyrene sulfonate or a salt thereof.

9. The composition of claim 1, wherein the composition comprises a dry powder.

10. The composition of claim 1, wherein the composition exhibits an in vitro disintegration or dissolution rate comprising about 50% disintegration or dissolution after about 1 minute to about 15 minutes in simulated gastric fluid comprising 34.2 mM NaCl and 0.1 N HCl, pH 1.2 using the USP basket method.

11. The composition of claim 1, wherein subjects administered the composition exhibit a plasma AUC for the opioid agonist of about 15% lower as compared to an equivalent opioid agonist dose lacking a strong cation exchange resin.

12. The composition of claim 1, wherein the opioid agonist comprises hydrocodone bitartrate.

13. An oral pharmaceutical composition comprising an immediately releasing dry admixture of hydrocodone or a salt thereof and polystyrene sulfonate or a salt thereof in a mass ratio of about 1:2 to about 1:8, and optionally, one or more pharmaceutically acceptable excipients,
    wherein less than about 1% of the hydrocodone is bound to the polystyrene sulfonate prior to solvation, and
    after solvation of two more doses of the composition simultaneously or successively over about a 4-hour period, the polystyrene sulfonate adsorbs about 15% to about 70% by mass of the hydrocodone and impedes its absorption into a subject's systemic circulation, lowering $C_{max}$ for the opioid agonist by about 30% to about 50% as compared to an equivalent dose of the opioid agonist lacking polystyrene sulfonate.

14. The composition of claim 13, wherein subjects administered the composition exhibit one or more of the following pharmacokinetic parameters:
    (a) a delayed $T_{max}$ for hydrocodone as compared to an equivalent hydrocodone dose lacking polystyrene sulfonate;
    (b) a lower plasma AUC for hydrocodone as compared to equivalent hydrocodone dose lacking polystyrene sulfonate;
    (c) an extended absorption time for hydrocodone as compared to an equivalent hydrocodone dose lacking polystyrene sulfonate; or
    (d) an extended clearance time for hydrocodone as compared to an equivalent hydrocodone dose lacking polystyrene sulfonate.

15. The composition of claim 13, wherein the mass ratio of hydrocodone to polystyrene sulfonate is about 1:4.

16. The composition of claim 13, wherein the composition exhibits an in vitro disintegration or dissolution rate comprising about 50% disintegration or dissolution after about 1 minute to about 15 minutes in simulated gastric fluid comprising 34.2 mM NaCl and 0.1 N HCl, pH 1.2, using the USP basket method.

17. The composition of claim 13, wherein subjects administered the composition exhibit a plasma AUC for hydrocodone of about 15% lower as compared to an equivalent opioid agonist dose lacking polystyrene sulfonate.

18. The composition of claim 13, wherein the hydrocodone comprises hydrocodone bitartrate.

19. A dosage form comprising the composition of claim 13 comprising a dry powder.

20. A method for treating pain while mitigating the risk of overingestion, the method comprising administering to a subject in need thereof the composition of claim 13.

* * * * *